US011123454B2

(12) United States Patent
Jiang et al.

(10) Patent No.: US 11,123,454 B2
(45) Date of Patent: Sep. 21, 2021

(54) BIODEGRADABLE, THERMALLY RESPONSIVE INJECTABLE HYDROGEL FOR TREATMENT OF ISCHEMIC CARDIOMYOPATHY

(71) Applicant: University of Pittsburgh—Of the Commonwealth System of Higher Education, Pittsburgh, PA (US)

(72) Inventors: Hongbin Jiang, Export, PA (US); William R. Wagner, Gibsonia, PA (US); Tomo Yoshizumi, Pittsburgh, PA (US); Yang Zhu, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/794,796

(22) Filed: Feb. 19, 2020

(65) Prior Publication Data
US 2020/0222583 A1 Jul. 16, 2020

Related U.S. Application Data

(62) Division of application No. 15/304,016, filed as application No. PCT/US2015/025728 on Apr. 14, 2015, now Pat. No. 10,589,002.

(60) Provisional application No. 61/979,244, filed on Apr. 14, 2014.

(51) Int. Cl.
| A61K 47/32 | (2006.01) |
| C08G 63/91 | (2006.01) |
| C08F 8/00 | (2006.01) |
| C08F 212/00 | (2006.01) |
| A61L 27/16 | (2006.01) |
| A61K 9/00 | (2006.01) |
| A61L 27/52 | (2006.01) |
| A61L 27/54 | (2006.01) |
| C08F 220/54 | (2006.01) |
| A61K 47/30 | (2006.01) |

(52) U.S. Cl.
CPC ............ *A61L 27/16* (2013.01); *A61K 9/0019* (2013.01); *A61K 9/0024* (2013.01); *A61L 27/52* (2013.01); *A61L 27/54* (2013.01); *C08F 220/54* (2013.01); *A61K 47/30* (2013.01); *A61L 2300/414* (2013.01); *A61L 2400/06* (2013.01); *A61L 2430/20* (2013.01)

(58) Field of Classification Search
CPC .............................. C08F 220/54; A61L 27/16
See application file for complete search history.

(56) References Cited

U.S. PATENT DOCUMENTS

| 5,763,548 A | 6/1998 | Matyjaszewski et al. |
| 5,789,487 A | 8/1998 | Matyjaszewski et al. |
| 5,807,937 A | 9/1998 | Matyjaszewski et al. |
| 6,541,580 B1 | 4/2003 | Matyjaszewski et al. |
| 7,678,869 B2 | 3/2010 | Matyjaszewski et al. |
| 8,461,132 B2 | 6/2013 | Cohen et al. |
| 2003/0120028 A1 | 6/2003 | Lin et al. |
| 2005/0154376 A1 | 7/2005 | Riviere et al. |
| 2008/0096975 A1 | 4/2008 | Guan et al. |
| 2010/0203141 A1 | 8/2010 | Yarin et al. |
| 2011/0117195 A1 | 5/2011 | Hsieh et al. |
| 2012/0156176 A1 | 6/2012 | Fujimoto et al. |
| 2015/0209473 A1 | 7/2015 | Michal et al. |

FOREIGN PATENT DOCUMENTS

| CN | 101574514 A | 11/2009 |
| CN | 101618235 A | 1/2010 |
| EP | 1072617 A1 | 1/2001 |
| EP | 2109469 A2 | 10/2009 |
| WO | 02087481 A1 | 11/2002 |
| WO | 2004014969 A1 | 2/2004 |
| WO | 2008045904 A2 | 4/2008 |
| WO | 2010127254 A2 | 11/2010 |
| WO | 2012164101 A1 | 12/2012 |

OTHER PUBLICATIONS

Anderson et al.; "Foreign Body Reaction to Biomaterials"; Semin Immunol; 2008; pp. 86-100; vol. 20:2.
Antheunis et al.; "Autocatalytic Equation Describing the Change in Molecular Weight during Hydrolytic Degradation of Aliphatic Polyesters"; Biomacromolecules; 2010; pp. 1118-1124; vol. 11.
Aoki et al.; "Angiogenesis induced by hepatocyte growth factor in non-infarcted myocardium and infarcted myocardium: up-regulation of essential transcription factor for angiogenesis, ets"; Gene Therapy; 2000; pp. 417-427; vol. 7.
Appell; "Collagen Injection Therapy for Urinary Incontinence"; The Craft of Urologic Surgery; 1994; pp. 177-182; vol. 21:1; Urologic Clinics of North America.
Ara et al.; "Effect of blending calcium compounds on hydrolytic degradation of poly(DL-lactic acid-co-glycolic acid)"; Biomaterials; 2002; pp. 2479-2483; vol. 23.
Bae et al.; "N-Isopropylacrylamide Copolymers (Drug Delivery)"; Polymeric Materials Encyclopedia F-G; pp. 3492-3497; vol. 4.
Batista et al.; "Partial Left Ventriculectomy to Treat End-Stage Heart Disease"; Ann Thorac Surg; 1997; pp. 634-638; vol. 64.

(Continued)

*Primary Examiner* — Shobha Kantamneni
(74) *Attorney, Agent, or Firm* — The Webb Law Firm

(57) ABSTRACT

Provided are novel biocompatible copolymers, compositions comprising the copolymers, and methods of using the copolymers. The copolymers are non-toxic and typically have an LCST below 37° C. Compositions comprising the copolymers can be used for wound treatment, as a cellular growth matrix or niche and for injection into cardiac tissue to repair and mechanically support damaged tissue. The copolymers comprise numerous ester linkages so that the copolymers are erodeable in situ. Degradation products of the copolymers are soluble and non-toxic. The copolymers can be amine-reactive so that they can conjugate with proteins, such as collagen. Active ingredients, such as drugs, can be incorporated into compositions comprising the copolymers.

6 Claims, 30 Drawing Sheets

(56) References Cited

OTHER PUBLICATIONS

Brandl et al.; "Rational design of hydrogels for tissue engineering: Impact of physical factors on cell behavior"; Biomaterials; 2007; pp. 134-146; vol. 28.

Brazel et al.; "Synthesis and Characterization of Thermo- and Chemomechanically Responsive Poly(N-isopropylacrylamide-co-methacrylic acid) Hydrogels"; Macromolecules; 1995; pp. 8016-8020; vol. 28.

Bromberg et al.; "Temperature-responsive gels and thermogelling polymer matrices for protein and peptide delivery"; Advanced Drug Delivery Reviews; 1998; pp. 197-221; vol. 31.

Chaudhry et al.; "Passive Epicardial Containment Prevents Ventricular Remodeling in Heart Failure"; Ann Thorac Surg; 2000; pp. 1275-1280; vol. 70.

Christman et al.; "Fibrin Glue Alone and Skeletal Myoblasts in a Fibrin Scaffold Preserve Cardiac Function after Myocardial Infarction"; Tissue Engineering; 2004; pp. 403-409; vol. 10:3/4.

Cloyd et al.; "Material properties in unconfined compression of human nucleus pulposus, injectable hyaluronic acid-based hydrogels and tissue engineering scaffolds"; Eur Spine J; 2007; pp. 1892-1898; vol. 16.

Cui et al.; "A New Hydrolysis-Dependent Thermosensitive Polymer for an Injectable, Degradable Drug Delivery System"; Biomacromolecules; 2007; pp. 1280-1286; vol. 8:4.

Cui et al.; "Manipulating Degradation Time in a N-isopropylacrylamide-Based Co-polymer with Hydrolysis-Dependent LCST"; Journal of Biomaterials Science; 2010; pp. 913-926; vol. 21.

Davis et al.; "Injectable Self-Assembling Peptide Nanofibers Create Intramyocardial Microenvironments for Endothelial Cells"; Circulation; 2005; pp. 442-450; vol. 111:4.

Davis et al.; "Local myocardial insulin-like growth factor 1 (IGF-1) delivery with biotinylated peptide nanofibers improves cell therapy for myocardial infarction"; PNAS; 2006; pp. 8155-8160; vol. 103:21.

Defail et al.; "Controlled release of bioactive doxorubicin from microspheres embedded within gelatin scaffolds"; J Biomed Mater Res; 2006; pp. 954-962; vol. 79A.

Dickey et al.; "Eutectic Gallium-Indium (EGaIn): A Liquid Metal Alloy for the Formation of Stable Structures in Vlicrochannels at Room Temperature"; Adv. Funct. Mater; 2008; pp. 1097-1104; vol. 18.

Dor et al.; "Efficacy of Endoventricular Patch Plasty in Large Postinfarction Akinetic Scar and Severe Left Ventricular Dysfunction: Comparison With a Series of Large Dyskinetic Scars"; J Thorac Cardiovasc Surg; 1998; pp. 50-59; vol. 116.

Druecke et al.; "Modulation of scar tissue formation using different dermal regeneration templates in the treatment of experimental full-thickness wounds"; Wound Rep Reg; 2004; pp. 518-527; vol. 12:5.

Dubois et al.; "Self-Assembling Peptide Nanofibers and Skeletal Myoblast Transplantation in Infarcted Myocardium"; Journal of Biomedical Materials Research Part B: Applied Biomaterials; pp. 222-228.

Feil et al.; "Effect of Comonomer Hydrophilicity and Ionization on the Lower Critical Solution Temperature of N-Isopropylacrylamide"; Macromolecules; 1993; pp. 2496-2500; vol. 26.

Freyman et al.; "A quantitative, randomized study evaluating three methods of mesenchymal stem cell delivery following myocardial infarction"; European Heart Journal; 2006; pp. 1114-1122; vol. 27.

Fu et al.; "Visual Evidence of Acidic Environment Within Degrading Poly(lactic-co-glycolic acid) (PLGA) Microspheres"; Pharmaceutical Research; 2000; pp. 100-106; vol. 17:1.

Fujimoto et al.; "An Elastic, Biodegradable Cardiac Patch Induces Contractile Smooth Muscle and Improves Cardiac Remodeling and Function in Subacute Myocardial Infarction"; J Am Coll Cardiol; 2007; pp. 2292-2300; vol. 49:23.

Fujimoto et al.; "In Vivo Evaluation of a Porous, Elastic, Biodegradable Patch for Reconstructive Cardiac Procedures"; Ann Thorac Surg; 2007; pp. 648-654; vol. 83:2.

Fujimoto et al.; "Synthesis, characterization and therapeutic efficacy of a biodegradable, thermoresponsive hydrogel designed for application in chronic infarcted myocardium"; Biomaterials; 2009; pp. 4357-4368; vol. 30:26.

Galperin et al; "A Degradable, Thermo-sensitive Poly(N-isopropyl acrylamide)—Based Scaffold with Controlled Porosity for Tissue Engineering Applications"; Biomacromolecules; 2010; pp. 2583-2592; vol. 11:10.

Ghoniem et al.; "The Evolving Role of Submucosal Injectables for Treating Internal Sphincteric Deficieny"; Urologic Nursing; 1998; pp. 125-128; vol. 18:2.

Gil et al.; "Stimuli-reponsive polymers and their bioconjugates"; Prog. Polym. Sci.; 2004; pp. 1173-1222; vol. 29.

Gnecchi et al.; "Evidence supporting paracrine hypothesis for Akt-modified mesenchymal stem cell-mediated cardiac protection and functional improvement"; The FASEB Journal; 2006; pp. 661-669; vol. 20:6.

Goldstein et al.; "Ventricular Remodeling; Mechanism and Prevention"; Cardiology Clinics; 1998; pp. 623-632; vol. 16:4.

Gong et al.; "Biodegradable in situ gel-forming controlled drug delivery system based on thermosensitive PCL-PEG-PCL hydrogel. Part 2: Sol-gel-sol transition and drug delivery behavior"; Acta Biomaterialia; 2009; pp. 3358-3370; vol. 5.

Gong et al.; "Synthesis and characterization of PEG-PCL-PEG thermosensitive hydrogel"; International Journal of Pharmaceutics; 2009; pp. 89-99; vol. 365.

Guan et al.; "Protein-Reactive, Thermoresponsive Copolymers with High Flexibility and Biodegradability"; Biomacromolecules; 2008; pp. 1283-1292; vol. 9:4.

Hao et al.; "Angiogenic effects of sequential release of VEGF-A165 and PDGF-BB with alginate hydrogels after myocardial infarction"; Cardiovascular Research; 2007; pp. 178-185; vol. 75.

Hayakawa et al.; "Inhibition of Granulation Tissue Cell Apoptosis During the Subacute Stage of Myocardial Infarction Improves Cardiac Remodeling and Dysfunction at the Chronic Stage"; Circulation; 2003; pp. 104-109; vol. 108.

He et al.; "In situ gelling stimuli-sensitive block copolymer hydrogels for drug delivery"; Journal of Controlled Release; 2008; pp. 189-207; vol. 127.

Healy et al.; "Designing Biomaterials to Direct Biological Responses"; Annals NY Academy of Science; 1999; pp. 24-35; vol. 875.

Holloway et al.; "Modulating hydrogel crosslink density and degradation to control bone morphogenetic protein delivery and in vivo bone formation"; Journal of Controlled Release; pp. 63-70; vol. 191.

Holmes et al.; "Structure and Mechanics of Healing Myocardial Infarcts"; Annu. Rev. Biomed. Eng.; 2005; pp. 223-253; vol. 7.

Hsieh et al; "Controlled delivery of PDGF-BB for myocardial protection using injectable self-assembling peptide nanotibers"; The Journal of Clinical Investigation; 2006; pp. 237-248; vol. 116:1.

Huang et al.; "Injectable Biopolymers Enhance Angiogenesis after Myocardial Infarction"; Tissue Engineering; 2005; pp. 1860-1866; vol. 11:11/12.

Iwakura et al.; "Intramyocardial sustained delivery of basic fibroblast growth factor improves angiogenesis and ventricular function in a rat infarct model"; Heart Vessels; 2003; pp. 93-99; vol. 18.

Jeong et al.; "Thermosensitive sol-gel reversible hydrogels"; Advanced Drug Delivery Reviews; 2002; pp. 37-51; vol. 54.

Jiang et al.; "Injection of a novel synthetic hydrogel preserves left ventricle function after myocardial infarction"; J Biomed Mater Res Part A.; 2009; pp. 472-477.

Joo et al.; "Reverse thermogelling biodegradable polymer aqueous solutions"; J Mater Chem; 2009; pp. 5891-5905; vol. 19.

Kanemitsu et al.; "Insulin-like Growth Factor-1 Enhances the Efficacy of Myoblast Transplantation With Its Multiple Functions in the Chronic Myocardial Infarction Rat Model"; J Heart Lung Transplant; 2006; pp. 1253-1262; vol. 25.

Kawaguchi et al.; "Left Ventricular Volume Reduction Surgery: The 4th International Registry Report 2004"; J Card Surg; 2005; pp. S5-S11; vol. 20.

Kim et al.; "Synthesis and Characterization of Injectable Poly(N-isopropylacrylamide-co-acrylic acid) Hydrogels with Proteolytically Degradable Cross-Links"; Biomacromolecules; 2003; pp. 1214-1223; vol. 4.

(56) References Cited

OTHER PUBLICATIONS

Kim et al.; "Synthetic MMP-13 degradable ECMs based on poly(N-isopropylacrylamide-co-acrylic acid) semi-interpenetrating polymer networks. I. Degradation and cell migration"; J Biomed Mater Res Part A; 2005; pp. 73-88; vol. 75.
Kirschner et al.; "Hydrogels in Healthcare: From Static to Dynamic Material Microenvironments"; Acta Mater; 2013; pp. 931-944; vol. 61:3.
Klouda et al.; "Thermoresponsive hydrogels in biomedical applications—a review"; Eur J Pharm Biopharm; 2008; pp. 34-45; vol. 68:1.
Kloxin et al.; "Photodegradable hydrogels for dynamic tuning of physical and chemical properties"; Science; 2009; pp. 59-63; vol. 324:5923.
Kobsa et al.; "Bioengineering Approaches to Controlled Protein Delivery"; Pediatric Research; 2008; pp. 513-519; vol. 63:5.
Kumashiro et al.; "Dextran Hydrogels Containing Poly(N-isopropylacrylamide) as Grafts and Cross-Linkers Exhibiting Enzymatic Regulation in a Specific Temperature Range"; Macromol. Rapid Commun.; 2004; pp. 867-872; vol. 25.
Landa et al.; "Effect of Injectable Alginate Implant on Cardiac Remodeling and Function After Recent and Old Infarcts in Rat"; Circulation; 2008; pp. 1388-1396; vol. 117.
Lee et al.; "Copolymers of N-isopropylacrylamide, HEMA-lactate and acrylic acid with time-dependent lower critical solution temperature as a bioresorbable carrier"; Polym Int; 2005; pp. 418-422; vol. 54:7.
Lee et al.; "In situ-Gelling, Erodible N-Isopropylacrylamide Copolymers"; Macromol Biosci.; 2005; pp. 629-635; vol. 5:7.
Li et al.; "Injectable, Highly Flexible, and Thermosensitive Hydrogels Capable of Delivering Superoxide Dismutase"; Biomacromolecules; 2009; pp. 3306-3316; vol. 10.
Loh et al.; "Hydrolytic degradation and protein release studies of thermogelling polyurethane copolymers consisting of poly[(R)-3-hydroxybutyrate], poly(ethylene glycol), and poly(propylene glycol)"; Biomaterials; 2007; pp. 4113-4123; vol. 28.
Lu et al.; "Functional Improvement of Infarcted Heart by Co-Injection of Embryonic Stem Cells with Temperature-Responsive Chitosan Hydrogel"; Tissue Engineering: Part A; 2009; pp. 1437-1447; vol. 15:6.
Lu et al.; "In vitro degradation of thin poly(DL-lactic-co-glycolic acid) films"; J. Biomed. Mater. Res.; 1999; pp. 236-244; vol. 46.
Ma et al.; "A thermally responsive injectable hydrogel incorporating methacrylate-polylactide for hydrolytic lability"; Biomacromolecules; 2010; pp. 1873-1881; vol. 11:7.
Magovern; "Experimental and Clinical Studies with the Paracor Cardiac Restraint Device"; Semin Thorac Cardiovasc Surg; 2005; pp. 364-368; vol. 17.
Matsubayashi et al.; "Improved Left Ventricular Aneurysm Repair With Bioengineered Vascular Smooth Muscle Grafts"; Circulation; 2003; pp. II-219-II-225; vol. 108.
Matsusaki et al.; "Novel Functional Biodegradable Polymer IV: pH-Sensitive Controlled Release of Fibroblast Growth Factor-2 from a Poly(gamma-glutamic acid)-Sulfonate Matrix for Tissue Engineering"; Biomacromolecules; 2005; pp. 3351-3356; vol. 6.
Middleton et al.; "Synthetic biodegradable polymers as orthopedic devices"; Biomaterials; 2000; pp. 2335-2346; vol. 21.
Moon et al.; "Temperature-responsive compounds as in situ gelling biomedical materials"; Chem. Soc. Rev.; 2012; pp. 4860-4883; vol. 41.
Mukherjee et al., "Target Myocardial Microinjections of a Biocomposite Material Reduces Infarct Expansion in Pigs"; Ann Thorac Surg; 2008; pp. 1268-1276; vol. 86:4.
Nair et al.; "Biodegradable polymers as biomaterials"; Prog. Polym. Sci.; 2007; pp. 762-798; vol. 32.
Nelson et al.; "Intramyocardial Biomaterial Injection Therapy in the Treatment of Heart Failure: Materials, Outcomes and Challenges"; Acta Biomater; 2011; pp. 1-15; vol. 7:1.

Nishio et al.; "Decade of Histological Follow-Up for a Fully Biodegradable Poly-I-lactic Acid Coronary Stent (Igaki-Tamai Stent) in Humans: Are Bioresorbable Scaffolds the Answer?"; Circulation; 2014; pp. 534-535; vol. 129.
Oshima et al.; "Differential Myocardial Infarct Repair with Muscle Stem Cells Compared to Myoblasts"; Molecular Therapy; 2005; pp. 1130-1141; vol. 12:6.
Ota et al.; "Minimally Invasive Epicardial Injections Using a Novel Semiautonomous Robotic Device"; Circulation; 2008; pp. S115-S120; vol. 118.
Overstreet et al.; "Bioresponsive Copolymers of Poly(N-isopropylacrylamide) with Enzyme-Dependent Lower critical Solution Temperatures"; Biomacromolecules; 2010; pp. 1154-1159; vol. 11.
Park et al.; "Biodegradable Thermogels"; Accounts of Chemical Research; 2012; pp. 424-433; vol. 45:3.
Patronik et al.; "A Miniature Mobile Robot for Navigation and Positioning on the Beating Heart"; IEEE Transactions on Robotics; Oct. 2009; pp. 1109-1124; vol. 25:5.
Patterson et al.; "Enhanced proteolytic degradation of molecularly engineered PEG hydrogels in response to MMP-1 and MMP-2"; Biomaterials; 2010; pp. 7836-7845; vol. 31.
Peppas et al.; "Hydrogels in pharmaceutical formulations"; European Journal of Pharmaceutics and Biopharmaceutics; 2000; pp. 27-46; vol. 50.
Peppas et al.; "Stimuli-sensitive protein delivery systems"; J. Drug Del. Sci. Tech.; 2006; pp. 11-18; vol. 16:1.
Post et al.; "Therapeutic angiogenesis in cardiology using protein formulations"; Cardiovascular Research; 2001; pp. 522-531; vol. 49.
Potta et al.; "Controlling the degradation rate of thermoresponsive photo-cross-linked poly(organophosphazene) hydrogels with compositions of depsipeptide and PEG chain lengths"; Polymer Degradation and Stability; 2011; pp. 1261-1270; vol. 96.
Qiu et al.; "Environment-sensitive hydrogels for drug delivery"; Advanced Drug Delivery Reviews; 2001; pp. 321-339; vol. 53.
Qui et al.; "PEG-based hydrogels with tunable degradation characteristics to control delivery of marrow stromal cells for tendon overuse injuries"; Acta Biomaterialia; 2011; pp. 959-966; vol. 7.
Rane et al.; "Biomaterials for the Treatment of Myocardial Infarction"; Journal of the American College of Cardiology; 2011; pp. 2615-2629; vol. 58:25.
Rane et al.; "Increased Infarct Wall Thickness by a Bio-Inert Material is Insufficient to Prevent Negative Left Ventricular Remodeling after Myocardial Infarction"; PLoS One; 2011; pp. 1-8; vol. 6:6.
Ray et al.; "Isolation of vascular smooth muscle cells from a single murine aorta"; Methods in Cell Science; 2002; pp. 185-188; vol. 23.
Ruel-Gariepy et al.; "In situ-forming hydrogels—review of temperature-sensitive systems"; European Journal of Pharmaceutics and Biopharmaceutics; 2004; pp. 409-426; vol. 58.
Rzaev et al.; "Functional copolymers of N-isopropylacrylamide for bioengineering applications"; Prog Polym Sci; 2007; pp. 534-595; vol. 32.
Sacchi et al.; "Long-lasting fibrin matrices ensure stable and functional angiogenesis by highly tunable, sustained delivery of recombinant VEGF164"; PNAS; 2014; pp. 6952-6957; vol. 111:19.
Safaei Nikouei et al.; "Characterization of the thermo- and pH-responsive assembly of triblock copolymers based on poly(ethylene glycol) and functionalized poly(E-caprolactone)"; Acta Biomaterialia; 2011; pp. 3708-3718; vol. 7.
Sakakibara et al.; "Toward surgical angiogenesis using slow-released basic fibroblast growth factor"; European Journal of Cardiothoracic Surgery; 2003; pp. 105-112; vol. 24.
Segal et al.; "Stroke as a complication of cardiac catheterization: Risk factors and clinical features"; Neurology; 2001; pp. 975-977; vol. 56.
Seif-Naraghi et al.; "Safety and efficacy of an injectable extracellular matrix hydrogel for treating myocardial infarction"; Sci Transl Med; 2013; pp. 1-20; vol. 5.

(56) References Cited

OTHER PUBLICATIONS

Shao et al.; "Effects of Intramyocardial Administration of Slow-Release Basic Fibroblast Growth Factor on Angiogenesis and Ventricular Remodeling in a Rat Infarct Model"; Circ J; 2006; pp. 471-477; vol. 70.

Siepmann et al.; "How Autocatalysis Accelerates Drug Release from PLGA-Based Microparticles: A Quantitative Treatment"; Biomacromolecules; 2005; pp. 2312-2319; vol. 6.

Singh et al.; "Controlled release of recombinant insulin-like growth factor from a novel formulation of polylactide-co-glycolide microparticles"; Journal of Controlled Release; 2001; pp. 21-28; vol. 70.

Siparsky et al.; "Hydrolysis of Polylactic Acid (PLA) and Polycaprolactone (PCL) in Aqueous Acetonitrile Solutions: Autocatalysis"; Journal of Environmental Polymer Degradation; 1998; pp. 31-41; vol. 6:1.

Sjoback et al.; "Absorption and fluorescence properties of fluorescein"; Spectrochimica Acta Part A; 1995; pp. L7-L21; vol. 51.

Slaughter et al.; "Hydrogels in Regenerative Medicine"; Adv Mater; 2009; pp. 3307-3329; vol. 21.

Staiger et al.; "Magnesium and its alloys as orthopedic biomaterials: A review"; Biomaterials; 2006; pp. 1728-1734; vol. 27.

Stile et al.; "Synthesis and Characterization of Injectable Poly(N-isoprpylacrlamide)-Based Hydrogels That Support Tissue Formation in Vitro"; Macromolecules; 1999; pp. 7370-7379; vol. 32.

Suleiman et al.; "Apoptosis and the cardiac action of insulin-like growth factor I"; Pharmacology & Therapeutics; 2007; pp. 278-294; vol. 114.

Tabata et al.; "In vitro sorption and desorption of basic fibroblast growth factor from biodegradable hydrogels"; Biomaterials; pp. 1781-1789; vol. 19.

Takehara et al.; "Controlled Delivery of Basic Fibroblast Growth Factor Promotes Human Cardiosphere-Derived Cell Engraftment to Enhance Cardiac Repair for Chronic Myocardial Infarction"; J Am Coll Cardiol; 2008; pp. 1858-1865; vol. 52:23.

Tian et al.; "Physically Cross-Linked Alkylacrylamide Hydrogels: Phase Behavior and Microstructure"; Macromolecules; 2004; pp. 9994-10000; vol. 37.

Tous et al.; "Injectable Acellular Hydrogels for Cardiac Repair"; J of Cardiovasc. Trans. Res.; 2011; pp. 528-542; vol. 4.

Tsur-Gang et al.; "The effects of peptide-based modification of alginate on left ventricular remodeling and function after myocardial infarction"; Biomaterials; 2009; pp. 189-195; vol. 30.

Vakkalanka et al.; "Swelling behavior of temperature- and pH-sensitive block terpolymers for drug delivery"; Polymer Bulletin; 1996; pp. 221-225; vol. 36.

Vernengo et al.; "Evaluation of Novel Injectable Hydrogels for Nucleus Pulposus Replacement"; J Biomed Mater Res Part B: Appl Biomater; 2008; pp. 64-69; vol. 84B.

Versypt et al.; "Mathematical Modeling of Drug Delivery from Autocatalytically Degradable PLGA Microspheres—A Review"; J Control Release; 2013; pp. 29-37; vol. 165:1.

Vihola et al.; "Cytotoxicity of thermosensitive polymers poly(N-isopropylacrylamide), poly(N-vinylcaprolactam), and amphiphilically modified poly(N-vinylcaprolactam)"; Biomaterials; 2005; pp. 3055-3064; vol. 26.

Volklein et al.; "Modelling of a microelectromechanical thermoelectric cooler"; Sensors and Actuators; 1999; pp. 95-101; vol. 75.

Wall et al.; "Theoretical Impact of the Injection of Material Into the Myocardium: A Finite Element Model Simulation"; Circulation; 2006; pp. 2627-2635; vol. 114.

Wang et al.; "Injectable, rapid gelling and highly flexible hydrogel composites as growth factor and cell carriers"; Acta Biomaterialia; 2010; pp. 1978-1991; vol. 6.

Wang et al.; "Novel thermosensitive hydrogel injection inhibits post-infarct ventricle remodelling"; European Journal of Heart Failure; 2009; pp. 14-19; vol. 11.

Wang et al.; "Synthesis, characterization and surface modification of low moduli poly(ether carbonate urethane) ureas for soft tissue engineering"; Acta Biomaterialia; 2009; pp. 2901-2912; vol. 5.

Witte; "The history of biodegradable magnesium implants: A review"; Acta Biomaterialia; 2010; pp. 1680-1692; vol. 6.

Wu et al.; "Effects of porosity and pore size on in vitro degradation of three-dimensional porous poly (D, L-lactide-co-glycolide) scaffolds for tissue engineering"; J Biomed Mater Res; 2005; pp. 767-777; vol. 75A.

Wu et al.; "Toward the Development of Partially Biodegradable and Injectable Thermoresponsive Hydrogels for Potential Biomedical Applications"; ACS Applied Materials & Interfaces; 2009; pp. 319-327; vol. 1:2.

Yamashita et al.; "Reperfusion-Activated Akt Kinase Prevents Apoptosis in Transgenic Mouse Hearts Overexpressing Insulin-Like Growth Factor-1"; Circ Res; 2001; pp. 609-614; vol. 88.

Yu et al.; "Injectable block copolymer hydrogels for sustained release of a PEGylated drug"; International Journal of Pharmaceutics; 2008; pp. 95-106; vol. 348.

Yu et al.; "Restoration of left ventricular geometry and improvement of left ventricular function in a rodent model of chronic ischemic cardiomyopathy"; The Journal of Thoracic and Cardiovascular Surgery; 2009; pp. 180-187; vol. 137.

Yu et al.; "The effect of injected RGD modified alginate on angiogenesis and left ventricular function in a chronic rat infarct model"; Biomaterials; 2009; pp. 751-756; vol. 30.

Zhang et al.; "Effects of metal salts on poly (DL-lactide-co-glycolide) polymer hydrolysis"; Journal of Biomedical Materials Research; 1997; pp. 531-538; vol. 34.

Zhang et al.; "Synthesis and Characterization of pH- and Temperature-Sensitive Poly (methacrylic acid)/Poly(N-isopropylacrylamide) Interpenetrating Polymeric Networks"; Macromolecules; 2000; pp. 102-107; vol. 33.

Zolnik et al.; "Effect of acidic pH on PLGA microsphere degradation and release"; Journal of Controlled Release; 2007; pp. 338-344; vol. 122.

A

B

BIODEGRADABLE, THERMALLY RESPONSIVE INJECTABLE HYDROGEL FOR TREATMENT OF ISCHEMIC CARDIOMYOPATHY

This application is a Divisional of U.S. patent application Ser. No. 15/304,016, filed Oct. 13, 2016, which is the United States national phase of International Patent Application No. PCT/US2015/025728, filed Apr. 14, 2015, which claims the benefit of U.S. Provisional Patent Application No. 61/979,244, filed Apr. 14, 2014, each of which is incorporated herein by reference in its entirety.

NOTICE OF GOVERNMENT SUPPORT

This invention was made with government support under Grant No. HL105911 awarded by the National Institutes of Health. The government has certain rights in the invention.

BACKGROUND

A thermoresponsive, biodegradable elastomeric material is described herein, along with methods of making the material and uses for the material, particularly uses of the material in repairing defects in heart muscle.

Injectable thermally responsive hydrogels with a lower critical solution temperature (LCST) below body temperature represent promising biomaterials for a variety of biomedical applications, including regional tissue mechanical support as well as drug and cell delivery applications. Generally, the LCST-based phase transition occurs upon warming in situ as a result of entropically-driven dehydration of polymer components, leading to polymer collapse. Various naturally derived and synthetic polymers exhibiting this behavior have been utilized. Natural polymers include elastin-like peptides and polysaccharides derivatives, while notable synthetic polymers include those based on poly(n-isopropyl acrylamide) (pNIPAAm), and amphiphilic block copolymers, often containing poly(ethylene glycol). The structure of pNIPAAm, containing both hydrophilic amide bonds and hydrophobic isopropyl groups, leads to a sharp phase transition at the LCST. Studies suggest that the average number of hydrating water molecules per NIPAAm group falls from 11 to ~2 upon the hydrophobic collapse above the LCST (32° C.)

pNIPAAm based polymers have been extensively studied as injectable biomaterials for tissue regeneration and drug delivery, yet pNIPAAm itself is a non-biodegradable polymer with a constant LCST of approximately 32° C., which prevents ready clearance from the body at physiologic temperature. This limitation of pNIPAAm has provided the motivation for developing biodegradable NIPAAm-based polymers by conjugating the pNIPAAm with natural biodegradable segments such as MMP-susceptible peptide, gelatin, collagen, hyaluronic acid and dextran. However, these may be only partially bioabsorbable since sufficiently long pNIPAAm segments would remain non-soluble following removal of the natural segments.

Copolymers formed from NIPAAm and monomers with degradable side chains comprise another category of NIPAAm-based bioabsorbable, thermally responsive hydrogels. Hydrolytic removal of hydrophobic side chains increases the hydrophilicity of the copolymer, raising the LCST above body temperature and making the polymer backbone soluble. Due to the relative simplicity of the synthetic process, the most investigated biodegradable monomers have been HEMA-based monomers, such as 2-hydroxyethyl methacrylate-polylactide (HEMA-PLA), 2-hydroxyethyl methacrylate-polycaprolactone (HEMA-PCL) and 2-hydroxyethyl methacrylate-polytrimethylene carbonate (HEMA-PTMC). However, the backbone remnant following hydrolysis, HEMA, presents hydroxyethyl side groups (—$CH_2CH_2$—OH), which have a relatively limited effect on remnant polymer hydrophilicity. In previous studies, such hydrogels have been found to be either partially bioabsorbable or completely bioabsorbable, but have required the inclusion of considerably hydrophilic monomers such as acrylic acid (AAc) in the hydrogel synthesis.

Progressive remodeling of the left ventricular (LV) architecture occurs after myocardial infarction (MI). While initially required for maintenance of cardiac output, this response ultimately leads to LV dysfunction and heart failure in the absence of a recurrent ischemic event. Even with current optimal therapy, mortality in end-stage-heart-failure amounts to 20-50% per year. Heart transplantation is applied as the last therapeutic option for patients with terminal heart-failure, but requests for organ transplantation far outstrip the number of donor organs. Therefore, new therapeutic strategies are urgently needed in order to ameliorate both patient prognosis and quality of life.

Following MI, dilatation of the LV cavity has the effect of increasing LV wall tension, which triggers further dilatation of the LV cavity, and progression down a spiral of adverse cardiac remodeling towards the advanced stages of cardiac failure. To restore wall tension, the endoventricular circular patch plasty technique (the Dor procedure) and partial left ventriculectomy (the Batista procedure) have been clinically implemented for severe cardiac dilation and dysfunction many years after an infarction. Employing a similar strategy to limit the remodeling pathway at an earlier stage, epicardial restraint therapies, such as the Acorn Cardiac Support Device, and the Paracor device have been investigated. However, these both apply materials that are non-biodegradable and result in a permanent foreign body encapsulating the epicardium.

Using biodegradable and elastic polyester urethane urea, we recently reported that cardiac patch implantation onto a chronic myocardial infarct prevented further cardiac dilatation and improved contraction, while altering LV wall thickness and compliance. Supported by a finite element model simulation, another concept in locally treating the failing cardiac wall was proposed where a bulking material is injected into the infarcted left ventricular wall to positively alter cardiac mechanics and result in a potentially beneficial reduction of elevated stresses in the infarcted wall. In this numerical model the local systolic fiber stress distribution was determined in an infarcted LV wall injected with a mechanically passive material. The simulation showed that injection of a volume 4.5% that of the total LV wall volume and with a stiffness (elastic modulus) 20% of the natural LV tissue into the infarct border zone could decrease the fiber stress in the border zone of the infarct by 20% compared to a control simulation in which there was no injection. The mechanical simulation also showed that this attenuation effect on LV wall stress increased with the injection volume and the modulus of the injected material.

Thermally responsive hydrogels are particularly attractive materials for injection therapy following MI since it is possible to inject the necessary fluid volumes from a syringe maintained below body temperature. Upon injection and warming hydrogel mechanical properties are increased, the "holding" of the material at the injection site is facilitated and the mechanical benefit of the injected volume on the cardiac wall is increased.

However, despite the advantages of thermally responsive hydrogels known to date, many such gels are too robust, specifically in terms of a prolonged time period of hydrolysis and absorption by native tissue. If hydrolysis does not occur sufficiently rapidly, infiltration by native cells can be slowed, which in turn slows the rate of formation of new tissue at the site of injury.

Accordingly, a need exists, and a substantial challenge remains in the art for versatile biocompatible polymer compounds that can serve as cell growth substrates, for drug delivery purposes and generally for use in patients, for example for cardiac remodeling, where the degradation/hydrolysis time of such compounds can be precisely controlled, and where the polymer compounds and their degradation products exhibit desirable physical properties.

SUMMARY

Provided herein are compositions comprising thermoresponsive and biodegradable elastomeric materials; namely copolymers and compositions and structures, such as hydrogels, comprising the copolymers and methods of use of those compositions, including a method of treating a myocardial defect, such as an infarct. The copolymers remain fluid below physiological temperature (e.g., 37° C. for humans) or at or below room temperature (e.g., 25° C.), solidify (into a hydrogel) at physiological temperature, and degrade and dissolve at physiological conditions in a time-dependent manner, which is important for removal of the hydrogel after an applied surgical or medical procedure.

According to one embodiment, the copolymer comprises N-isopropylacrylamide (NIPAAm) residues (a residue is the remainder of a monomer incorporated into a polymer), hydroxyethyl methacrylate (HEMA) residues, the polyester macromer methacrylate-polylactide (MAPLA) macromer residues, and methacrylic acid (MAA) monomers. Alternately, the copolymer comprises NIPAAm residues, acrylic acid (AAc) residues, the polyester macromer hydroxyethyl methacrylate-poly(trimethylene carbonate) (HEMA-PTMC) macromer residues, and MAA monomers. Alternatives for NIPAAm residues include N-alkyl acrylamide residues in which the alkyl is one of methyl, ethyl, propyl, isopropyl and cyclopropyl. Alternatives for HEMA include (hydroxyl ($C_1$-$C_3$)alkyl)methacrylate and other methacrylate substituents that can modulate the LCST of the polymer. Although the size of the copolymers can vary, in one example, the copolymer has an $M_n$ of between 20 kD and 35 kD. In another example, the copolymer has a polydispersity index (PDI, $M_w/M_n$) of between 1 and 2.

According to another embodiment, the copolymer comprises NIPAAm residues, N-vinylpyrrolidone monomers (VP), and MAPLA macromer residues, or NIPAAm residues, N-vinylpyrrolidone monomers (VP), and hydroxyethyl methacrylate-poly(trimethylene carbonate) (HEMA-PTMC) macromer residues. Alternately, the copolymer comprises NIPAAm residues, VP monomers, and the polyester macromer hydroxyethyl methacrylate-poly(trimethylene carbonate) (HEMA-PTMC) macromer residues. Alternatives for NIPAAm residues in this embodiment include N-alkyl acrylamide residues in which the alkyl is one of methyl, ethyl, propyl, isopropyl and cyclopropyl. Alternatives for HEMA include (hydroxyl ($C_1$-$C_3$)alkyl)methacrylate and other methacrylate substituents that can modulate the LCST of the polymer. Although the size of the copolymers can vary, in one example, the copolymer has a $M_n$ of between 20 kD and 35 k D. In another example, the copolymer has a polydispersity index (PDI, $M_w/M_n$) of between 1 and 2.

In each copolymer, the ratio of the constituents of the polyester macromer may be varied. For example and without limitation, where the polyester macromer is a poly (trimethylene carbonate (TMC)-containing macromer), comprising hydroxyethyl methacrylate residues and varying numbers of trimethylene carbonate units/residues. In another embodiment, the polyester macromer is a methacrylate-polylactide macromer comprising methacrylate residues and varying numbers of lactide residues. Each component contributes to the desired physical properties of the hydrogel to enable an injectable material for delivering drugs or chemicals, encapsulating and transplanting cells, and injecting into empty cavities for wounds or tissue repair.

An optional amine-reactive component may be included in the copolymer as described above. The amine-reactive group can be a succinimide group, an oxysuccinimide group or an isocyanate group, such as is produced by incorporation of N-hydroxysuccinimide methacrylate (MANHS) or N-acryloxy succinimide (NAS) monomers into the copolymer. The amine-reactive groups bind to amine-containing compounds including biomolecules such as collagen and/or other bioactive or biocompatible materials or factors. Varying amounts of the amine-reactive component may be used, depending on the desired density of amine-reactive groups, while maintaining desirable physical and degradation properties of the resultant copolymer.

The composition of each component in the hydrogel determines the lower critical solution temperature (LCST) of the hydrogel. At a temperature less than the LCST, the hydrogel flows easily and can be injected into the desired shape. When the temperature is increased above the LCST, the hydrogel solidifies and retains its shape. Once solidified, the hydrogel is highly flexible and relatively strong at physiological temperature. For complete removal of the copolymer, the copolymer includes hydrolytically-cleavable bonds that results in soluble, non-toxic by-products, which results in dissolution of the degraded hydrogel and clearance of the degraded components.

In one embodiment, the copolymer has a lower critical solution temperature below 37° C., for example 36° C. or lower, 35° C. or lower, 34° C. or lower, or, in another embodiment between 10° C. and 34° C., including increments and sub-ranges therebetween, and in another embodiment, less than 20° C. According to one embodiment, the copolymer has a lower critical solution temperature above 37° C. after its ester bonds are hydrolyzed.

The polymer comprises a polyester macromer, for example and without limitation, a polyester macromer comprising methacrylate-polylactide residues. In one embodiment, the ratio of methacrylate and lactide residues in the polyester macromer is from 1:2 (methacrylate:lactide) to 1:8, in another, from 1:1 to 1:10, such as 1:1, 1:2, 1:3, 1:4, 1:5, 1:6, 1:7, 1:8, 1:9, and 1:10. In another non-limiting example, the polyester macromer comprises hydroxyethyl methacrylate and trimethylene carbonate residues. In one embodiment, the ratio of hydroxyethyl methacrylate and trimethylene carbonate residues in the polyester macromer ranges from 1:1 to 1:10, 1:2 to 1:5 or any increment within those ranges, including 1:1, 1:2, 1:3, 1:4, 1:4.2, 1:5, 1:6, 1:7, 1:8, 1:9, and 1:10. Amine-containing biomolecules or other compounds, such as proteins, carbohydrates, glycoproteins, etc. can be conjugated to the copolymer through an amine-reactive group, when incorporated into the copolymer. In certain embodiments, collagen, gelatin are suitable compounds, for instance and without limitation, between 1% wt and 10% wt collagen.

A composition comprising the copolymer described herein also may comprise an aqueous solvent, for example and without limitation, water, saline and phosphate-buffered saline. The composition also can include an active agent, such as, without limitation, one or more of an antiseptic, an antibiotic, an analgesic, an anesthetic, a chemotherapeutic agent, a clotting agent, an anti-inflammatory agent, a metabolite, a cytokine, a chemoattractant, a hormone, a steroid, a protein and a nucleic acid. In one embodiment, where the composition comprises a clotting agent, one example of a clotting agent is desmopressin. In another embodiment, for use (e.g.) in repair of cardiac tissue, the active agents are one or both of bFGF and IGF-1. A biological material, such as a cell or a virus particle may also be incorporated into the composition.

A method is provided of making a thermosensitive copolymer, for example and without limitation, a co-polymer described herein, the method comprising co-polymerizing NIPAAm, HEMA, MAPLA, and MAA monomers to make a copolymer. In another embodiment, the method comprises co-polymerizing NIPAAm, VP, and MAPLA to make a copolymer. In another embodiment, the method comprises co-polymerizing NIPAAm, AAc, HEMAPTMC, and MAA monomers. The monomers can be co-polymerized by any useful polymerization method, for example and without limitation by radical polymerization methods, such as free-radical polymerization or living polymerization methods, such as atom transfer radical polymerization (ATRP).

A method of treating a muscle defect, such as a myocardial defect, such as an infarct or traumatic injury, is provided. The method comprises injecting a composition comprising a copolymer having an LCST of less than 37° C., comprising N-alkyl acrylamide residues in which the alkyl is one of methyl, ethyl, propyl, isopropyl and cyclopropyl; hydroxyethylmethacrylate (HEMA) residues; methacrylate-polyactide (MAPLA) macromer residues; and methacrylic acid (MAA) residues into the area of (within, in contact with or in tissue surrounding) a myocardial defect, or a defect of any muscle tissue. In another embodiment, the method comprises injecting a composition comprising a copolymer having an LCST of less than 37° C., comprising N-alkyl acrylamide residues in which the alkyl is one of methyl, ethyl, propyl, isopropyl and cyclopropyl; N-vinylpyrrolidone monomers (VP); and methacrylate-polyactide (MAPLA) macromer residues into the area of (within, in contact with or in tissue surrounding) a myocardial defect, or a defect of any muscle tissue. The injection of either of the above general class of copolymers may take place from 1 day to 21 days after infarction (inclusive of values between those provided here). In an embodiment, the injection of the composition occurs between 7 and 14 days (inclusive of values between those provided here) following infarction, so as to maximize functional outcome through tissue remodeling while allowing time for the patient to recover from the insult.

According to another embodiment a method of growing cells is provided, comprising introducing cells into any copolymer composition described herein to produce a cell construct and incubating the cell construct under conditions suitable for growth of the cells. The composition can comprise cell growth media to facilitate cell growth within the composition. The cell construct can be administered to a patient (placed in a patient's body at a desired location), such as a human patient. In another embodiment, the composition is administered to a patient without cells, but so that the patient's cells migrate into the composition. The composition can be administered by an injection into the desired site, such as cardiac tissue within the patient.

For example, the composition may be injected in or around necrotic tissue in the heart. In one embodiment, the composition is injected approximately 2 weeks after the patient has a myocardial infarction. This injection may take place from 1 day to 21 days after infarction. In an embodiment, the injection of the composition occurs between 7 and 14 days following infarction, so as to maximize functional outcome through tissue remodeling while allowing time for the patient to recover from the insult. The composition also may include one or more active agents, such as, without limitation, an antiseptic, an analgesic, an anesthetic and an antibiotic. To facilitate heart repair, or repair of any tissue, or cell growth in general, the composition may comprise, with or without other active agents, one or more of a cytokine, a cell growth or differentiation agent and a metabolite, such as one or both of bFGF and IGF-1.

DETAILED DESCRIPTION

Figure 1:
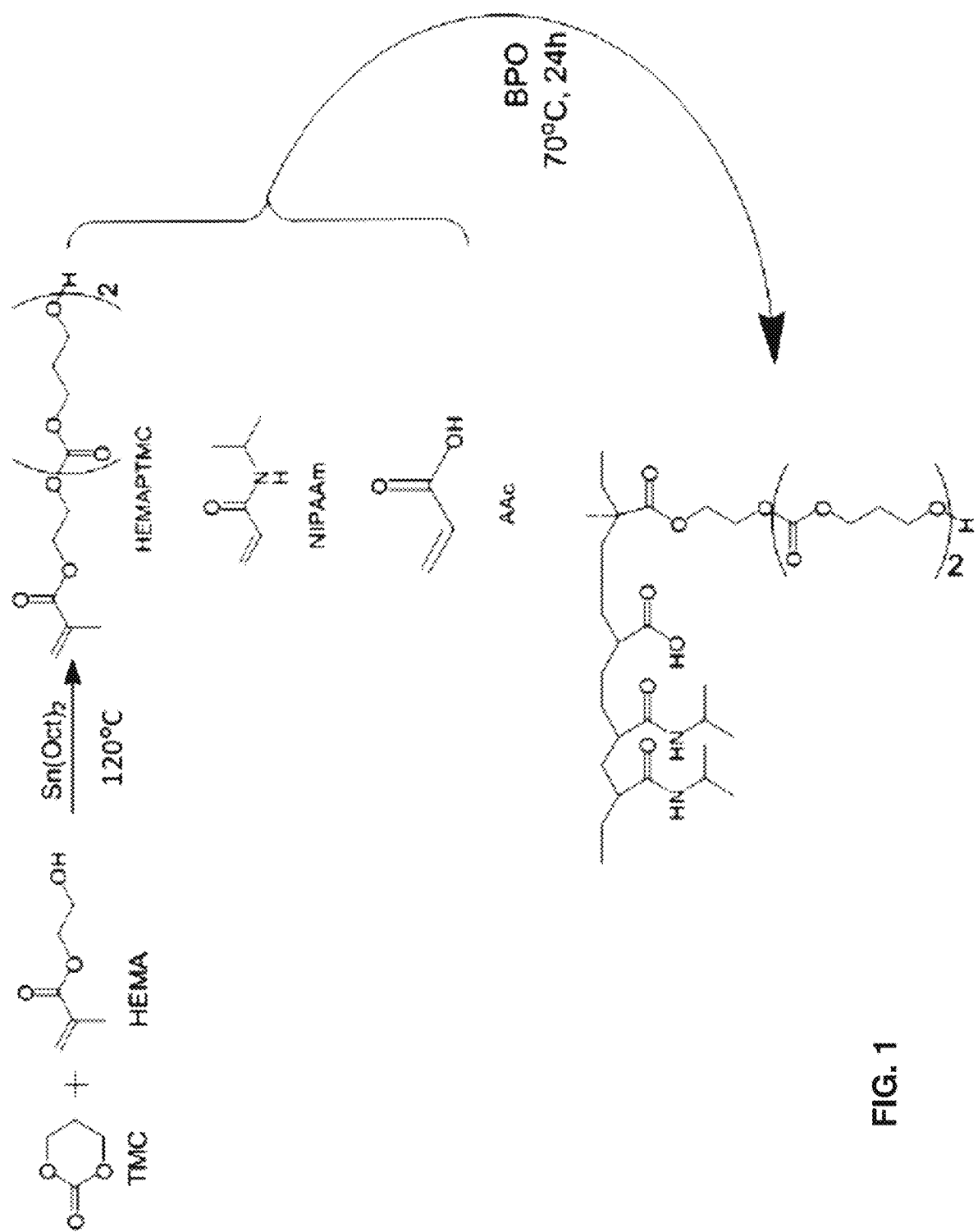
FIG. 1. Synthetic scheme for HEMAPTMC and the copolymer poly(NIPAAm-co-AAc-co-HEMAPTMC)

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts. A "copolymer consisting essentially of" two or more monomers or residues means that the copolymer is produced from the stated two or more monomers or contains the stated two or more monomers and is prepared from no other monomers or contains no other residues in any quantity sufficient to substantially affect the LCST properties, the degradation rate in vivo, and tensile strength of the copolymer. Thus, as an example, addition of insignificant or trace amounts of acrylic acid or other monomers to the feed during polymerization, or inclusion of insignificant amounts of acrylic acid or other residues in the copolymer is considered to be within the scope of a copolymer consisting essentially of an N-alkyl acrylamide residue in which the alkyl is one of methyl, ethyl, propyl, isopropyl and cyclopropyl; hydroxyethylmethacrylate; one or both of a polylactide-methacrylate MAPLA macromer and a HEMA-poly(trimethylene carbonate) macromer), an N-vinylpyrrolidone monomer (VP), a hydroxyethylmethacrylate (HEMA), and/or a methacrylic acid monomer (MAA), so long as the LCST, degradation rate and tensile strength of the resultant copolymer are not significantly different than that of the same copolymer omitting the acrylic acid residues. The significance of each value is determined independently and in relation to the intended use of the copolymer.

According to embodiments of the compounds and compositions described herein, provided herein are injectable hydrogels that are biodegradable, elastomeric and thermoresponsive and which can easily take the shape of a cavity into which they are injected in advance of phase transition to a solid hydrogel. The copolymers are injectable as a liquid at or below body temperature (about 37° C.) or room temperature (about 25° C.), or at a temperature in the range of from 10° C. to 30° C. and are solid at body temperature. These materials are useful for a number of purposes. For example, in treatment of patients, they may be used as an injectable stem cell niche for bone marrow transplants or for other transplantation settings; delivery vehicles for chemotherapy to tissue, such as, for example and without limitation, gut following tumor resections; sealants for pulmonary and neural applications as well as for emergency treatment of wounds. The materials also can find use as bulking agents for cosmetic applications or, even more generally, rheology modifiers. In one embodiment, the compositions are injected in a heart for repair or regeneration of cardiac tissue.

According to certain embodiments, copolymers comprise, are prepared from, or consist essentially of combinations of four types of subunits/residues: 1) N-alkyl acrylamide in which the alkyl is methyl, ethyl, propyl, isopropyl or cyclopropyl, for example N-isopropylacrylamide; 2) HEMA; 3) a methacrylate-polylactide (MAPLA) macromer; and 4) a methacrylic acid (MAA). In non-limiting examples, the MAPLA macromer has a lactide:methacrylate ratio of at least 1:1, or in the range of 2-3:1 (that is, ranging from 2:1 to 3:1). In some embodiments, the feed ratio is 75-85:5-10:3-14.5:0.5-2, wherein (NIPAAm+MAPLA):(HEMA+MAA)=85-95:5-15 (inclusive of values between those provided here). In one example, the feed ratio of HEMA is 10, such that the feed ratio of NIPAAm:HEMA:MAPLA is 75-85:10:5-10, for example and without limitation, in this embodiment, the feed ratio of NIPAAm:HEMA:MAPLA might be one of 84:10:6, 82:10:8 and 80:10:10. In another embodiment, the feed ratios of NIPAAm:HEMA:MAPLA:MAA are between 80:5:10:5 and 80:9.5:10:0.5.

The degradation rate is positively correlated to the amount of MAA included in the composition. Degradation of a copolymer hydrogel formed as described herein may be 200 days and less, depending on MAA content. Those of skill will easily be able to fine-tune the MAA content to match a preferred degradation rate. By degradation it is meant that the copolymer (and/or hydrogel formed from said copolymer) is substantially degraded at the indicated time point, for example and without limitation 80%, 85%, 90%, 95%, 99%, or 99.9% degraded (that is, 20%, 15%, 10%, 5%, 1%, or 0.1% remaining at the indicated time point). In some embodiments, the hydrogel degrades in less than 100 days, less than 90 days, less than 80 days, less than 70 days, less than 60 days, less than 50 days, less than 40 days, less than 30 days, less than 20 days, less than 10 days, or less than 5 days.

According to another embodiment, copolymers comprise, are prepared from, or consist essentially of four types of subunits/residues: 1) N-alkyl acrylamide in which the alkyl is methyl, ethyl, propyl, isopropyl or cyclopropyl, for example N-isopropylacrylamide; 2) acrylic acid (AAc); 3) a hydroxyethyl methacrylate-poly(trimethylene carbonate) (HEMAPTMC) macromer; and 4) an MAA macromer monomer. In non-limiting examples, the HEMA-poly(trimethylene carbonate) macromer has a TMC:HEMA ratio of at least 1:1, or in the range of 2-3:1 (that is, ranging from 2:1 to 3:1). In other non-limiting examples, the feed ratio of NIPAAm:AAc:HEMAPTMC is 85-87:3-5:10, for example, 86-87:3-4:10.

In other non-limiting examples, the feed ratio (the molar ratio of monomers in the polymerization reaction used to prepare the copolymer) of NIPAAm:HEMAPTMC is 75-85:2-14.5 (inclusive of values between those provided here), with a feed ratio of MAA being in the range of 0.5-2. In another embodiment, the feed ratios of NIPAAm:HEMAPTMC:MAA are between 80:10:5 and 80:10:0.5. The degradation rate of the copolymer is directly proportional to the amount of MAA included in the composition. Those of skill will understand that feed ratios of the other constituents of the copolymer may be adjusted to any useful range. Degradation of a copolymer hydrogel formed as described herein may be 200 days and less, depending on MAA content. Those of skill will easily be able to fine-tune the MAA content to match a preferred degradation rate. In some embodiments, the hydrogel degrades in less than 100 days, less than 90 days, less than 80 days, less than 70 days, less than 60 days, less than 50 days, less than 40 days, less than 30 days, less than 20 days, less than 10 days, or less than 5 days.

In another embodiment, copolymers comprise, are prepared from, or consist essentially of combinations of three types of subunits/residues: 1) N-alkyl acrylamide in which the alkyl is methyl, ethyl, propyl, isopropyl or cyclopropyl, for example N-isopropylacrylamide; 2) N-vinylpyrrolidone (VP); and 3) a methacrylate-polylactide (MAPLA) macromer. In non-limiting examples, the MAPLA macromer has a lactide:methacrylate ratio of at least 1:1, or in the range of 2-4:1 (that is, ranging from 2:1 to 4:1). In some embodiments, the feed ratio for NIPAAm:VP:MAPLA is 75-85:5-20:5-10, wherein (NIPAAm+MAPLA):(VP)=85-95:5-15 (inclusive of values between those provided here). In one embodiment, the feed ratio of NIPAAm:VP:MAPLA is in the range of 70-90:5-20:5-20. In one example, the feed ratio of VP is 10, such that the feed ratio of NIPAAm:VP:MAPLA is 75-85:10:5-10, for example and without limitation, in one embodiment, the feed ratio of NIPAAm:VP:MAPLA is be one of 80:10:10 or 85:10:5. In another embodiment, the feed ratio of VP is 15, such that the feed ratio of NIPAAm:VP:MAPLA is 75-85:15:5-10. In one embodiment the feed ratio is 80:15:5.

The degradation rate is positively correlated to the amount of VP included in the composition, that is, less VP leads to decreased degradation. Degradation of a copolymer hydrogel formed as described herein is typically 200 days and less, depending on VP content. Those of skill will easily be able to fine-tune the VP content to match a preferred degradation rate. As described above, by degradation it is meant that the copolymer (and/or hydrogel formed from said copolymer) is substantially degraded at the indicated time point, with percentage degraded (or percentage remaining) being as described above. In some embodiments, the hydrogel degrades in less than 100 days, less than 90 days, less than 80 days, less than 70 days, less than 60 days, less than 50 days, less than 40 days, less than 30 days, less than 20 days, less than 10 days, or less than 5 days.

In addition to characterization by feed ratio, copolymers described herein may be characterized by the ratio of incorporated monomer/macromer residue. For example, and without limitation, copolymers described herein may include NIPAAm:HEMA:MAPLA:MAA, NIPAAm:AAc:HEMAPTMC:MAA, or NIPAAm:VP:MAPLA in ratios similar to those described above regarding feed ratios. Those of ordinary skill in the art will understand that due to polymerization, copolymers may comprise, by molar percentage, as follows:

NIPAAm:HEMA:MAPLA:MAA 71.5-92.5:2.5-16:4.5-11:0.5-2.5, or 72-88:3-15:4.5-11:0.5-2;

NIPAAm:AAc:HEMAPTMC:MAA 71.5-94:2.5-16:4.5-11:0.5-2.5, or 72-88:3-15:4.5-11:0.5-2; and NIPAAm:VP:MAPLA 63-93:4-22:3-22, or 68-92.5:4.5-21:3-21.

In one embodiment, the incorporated molar ratio of monomer and macromer residues for NIPAAm:VP:MAPLA is 85-88:6-12:2-7. Those of skill will understand that final incorporated amounts of residues may vary from the feed ratio that is utilized by up to 10%, inclusive of values within that range, for example 3%

The copolymers, compositions and components thereof are preferably biocompatible. By "biocompatible," it is meant that a polymer composition and its normal in vivo degradation products are cytocompatible and are substantially non-toxic and non-carcinogenic in a patient within useful, practical and/or acceptable tolerances. By "cytocompatible," it is meant that the copolymers or compositions are substantially non-toxic to cells and typically and most desirably can sustain a population of cells and/or the polymer compositions, devices, copolymers, and degradation products thereof are not cytotoxic and/or carcinogenic within useful, practical and/or acceptable tolerances. For example, a copolymer composition when placed in a human epithelial cell culture does not adversely affect the viability, growth, adhesion, and number of cells. In one non-limiting example, the co-polymers, compositions, and/or devices are "biocompatible" to the extent they are acceptable for use in a human or veterinary patient according to applicable regulatory standards in a given legal jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues organs or the organism from the implanted compositions.

As used herein, a "polymer" is a compound formed by the covalent joining of smaller molecules, which are referred to herein as monomers before incorporation into the polymer and residues, or polymer subunits, after incorporated into a polymer. A "copolymer" is a polymer comprising two or more different residues. Non-limiting examples of monomers, in the context of the copolymers described herein, include: acrylic or acrylamide monomers, acrylic N-hydroxysuccinimide ester monomers, N-hydroxysuccinimide methacrylate monomers, acrylate or methacrylate forms of N-acryloxy succinimide (NAS) monomers, hydroxyethyl methacrylate monomers, methacrylate monomers, acrylate or methacrylate forms of lactide monomers, and acrylate or methacrylate forms of trimethylene carbonate (TMC) monomers. A monomer may be a macromer prepared from smaller monomers, such as a hydroxyethyl methacrylate-polylactide (HEMAPLA) macromer, a hydroxyethyl methacrylate-poly(trimethylene carbonate) (HEMAPTMC) macromer, a methacrylate-polylactide (MAPLA) macromer, an N-vinylpyrrolidone (VP) monomer, and/or a methacrylic acid (MAA) monomer as described herein.

Monomers (including as a group macromers) can be introduced into the copolymer by radical polymerization or other polymerization methods, such as living polymerization (e.g., atom transfer radical polymerization), or in any useful manner using any suitable initiator, such as benzoyl peroxide. These polymerization processes are well-known in the polymer chemistry field. Radical polymerization is one of the most widely used methods for preparing high polymer from a wide range of vinyl monomers. Although radical polymerization of vinyl monomers is very effective, it does not allow for the direct control of molecular weight, control of chain end functionalities or for the control of the chain architecture, e.g., linear vs. branched or graft polymers. Living polymerization systems have been developed which allow for the control of molecular weight, end group functionality, and architecture. ATRP is a type of controlled radical polymerization or living radical polymerization. (see, e.g., U.S. Pat. Nos. 5,763,548, 5,807,937, 5,789,487, 6,541,580, and 7,678,869). Controlled radical polymerization methods facilitate production of precise polymer, copolymer and block copolymer structures, such as A-B-A structures.

As used herein, an acrylic monomer has the general structure ($CH_2$=CH—C(O)—OR), and, when polymerized, forms the general polymer structure having an alkylene backbone ( . . . C—C—C—C—C . . . ) and the overall structure: . . . C—(—C(C(O)OR)—C—)$_n$—C(C(O)OR)—C . . . in which each instance of R can be the same, or in the case of a copolymer, independently different:

Polyester polymer backbones are polymer backbones containing two or more ester groups. A polyester linkage has an average of more than one ester units (—C(O)O—), as opposed to an ester linkage that has one ester unit. An example is a methacrylate-polylactide macromer as described herein. Another example is a HEMA-poly(trimethylene carbonate) macromer. Other examples of residues that comprise ester linkages include, without limitation, caprolactones, glycolides and a trimethylene carbonate residues.

Polyester macromers are compounds containing on the average more than one, and preferably two or more ester linkages. In the context of macromer and polymer preparations, unless otherwise indicated, the number of residues indicated as being present in a given polymer or macromer is an average number and is not to be construed as an absolute number. Thus, as a non-limiting example, in the context of HEMAPLA macromers, the numbers 2.1, 3.9 and 7.0 refer to an estimated average number of —C(O)—CH(CH$_3$)—O— residues present in the macromers in the macromer composition, and, when incorporated into a copolymer, the average number of —C(O)—CH(CH$_3$)—O— residues present in the incorporated polyester macromer residues. The average number of residues may be determined by any method, for example and without limitation, by $^1$H-NMR, as in the examples, below.

In describing ratios of respective monomers for any given copolymer, it is convenient to refer to feed ratios of the monomers in respect to the polymerization method used to produce the copolymer, for example and as used herein, in reference to the radical polymerization methods used to prepare the copolymers. This is especially so when considering that the products of the polymerization process are polydisperse and are often random in their composition. The feed ratios typically closely represent the ratios of monomer residues in the copolymer, but typically do not exactly match because certain monomers incorporate more efficiently than others in any given copolymer composition. The actual ratios of monomer residues typically vary less than 10%, and often less than 5% of the feed ratios. As an example, in Table 1, the feed ratio of 86/4/10 results in an actual composition of 88.3/3.3/8.4, a less than 3% difference in composition. As used herein a "feed ratio" refers to a feed ratio in a typical radical polymerization method, such as the methods described in the examples below and the ranges described above.

In another embodiment of the copolymer compositions described herein, the poly(NIPAAm-co-AAc-co-HEMAPTMC-co-MAA), poly(NIPAAm-co-HEMA-co-MAPLA-co-MAA), or poly(NIPAAm-co-VP-co-MAPLA) copolymers, optionally comprise an amine-reactive component or group, or are incorporated into a block copolymer with a hydrophilic polymer, such as a polyether, which is exemplified by polyethylene glycol (PEG). In one example, the block copolymer compositions have the structure A-B-A where A is poly(NIPAAm-co-AAc-co-HEMAPTMC-co-MAA), poly(NIPAAm-co-HEMA-co-MAPLA-co-MAA), or poly(NIPAAm-co-VP-co-MAPLA), and B is a polyethylene glycol block having, for example, an average molecular weight of from between 500 D and 25 kD, for instance between 1 kD and 20 kD. The "A" blocks can be added by any useful method, for instance, they can be synthesized by any method and attached to the B block by any useful chemistry. In one embodiment, the A blocks are polymerized from the B block. The terminal portions of the B block can be modified to act as initiators for a polymerization reaction. As described in the Examples below, the ends of a PEG block can be modified to act as an ATRP initiator, by addition of a suitable halide-containing group, for example by reacting PEG with α-bromoisobutyryl bromide. By using controlled radical polymerization processes, precise block copolymers can be prepared with low polydispersity indices (PDI), such as PDI<2.

Lower critical solution temperature (LCST) refers to the temperature below which the constituents of the hydrogel are soluble in water and above which the constituents are insoluble. When the LCST is reached, the polymer constituents in an aqueous solution will aggregate to form hydrogel (a solid, for purposes herein). The LCST can be determined by measuring the change in transmittance with a UV-Vis spectrometer as a function of temperature. LCST also can be determined by any other useful method—for example and without limitation by Differential Scanning calorimetry (DSC). DSC is used to measure LCST in the examples below.

One unique aspect of the polymers described herein is that the LCST of these polymers is preferably less than 37° C., and may be less than 20° C., for example, between 10° C. and about 37° C., for instance between 10° C. and 25° C., so that the polymer can be distributed through the marketplace, stored and administered to a patient as a liquid at ambient temperatures (or, if necessary, maintained at a cool temperature with an ice-pack, refrigerator or other cooling device), and the polymer gels as it warms past its LCST. Many polymers suitable for administration to patients require mixing of monomers immediately prior to use, which is undesirable for many reasons. For instance, it is impractical to ask doctors, nurses or technicians to mix monomers as they need the polymer. Further, monomers can have varying degrees of toxicity. The copolymers described herein do not require conducting a chemical reaction at the site of use and the copolymers can be washed free of monomer contamination prior to distribution in the marketplace. Lastly, the release of a portion of the aqueous phase during phase transition can facilitate local drug delivery in the excluded aqueous phase.

Another desirable physical quality of the polymers described herein is that, when ester linkages in the composition are hydrolyzed (for instance over time in situ in a living system, such as a human patient), the released copolymer fragments have an LCST above 37° C., so that they are soluble (and as an additional benefit, non-toxic), facilitating safe degradation and clearance of the polymer over time in a living system such as a human body.

In one embodiment, the copolymer comprises an acrylic residue having an amine-reactive group. The copolymer may be reacted with amine-containing compositions, such as compositions or molecules comprising amine groups, for example and without limitation, collagen, fibrin, gelatin and heparin.

In one non-limiting example in which the copolymer comprises a macromer comprising methacrylate and lactide residues, the ratio of methacrylate and lactide residues in the polyester macromer is from 1:1 to 1:10, such as 1:1, 1:2, 1:3, 1:4, 1:5, 1:6, 1:7, 1:8, 1:9, and 1:10 (inclusive of values between those provided here). In another non-limiting embodiment, the ratio of methacrylate to lactide residues in the polyester macromer is from 1:4 to 1:1, such as 1:4, 1:3, 1:2, or 1:1 (inclusive of values between those provided here). In another non-limiting example in which the copolymer comprises a macromer comprising hydroxyethyl methacrylate and trimethylene carbonate residues, the ratio of hydroxyethyl methacrylate to trimethylene carbonate residues in the polyester macromer ranges from 1:1 to 1:10, 1:2 to 1:5 or any increment within those ranges, including 1:1, 1:2, 1:3, 1:4, 1:4.2, 1:5, 1:6, 1:7, 1:8, 1:9, and 1:10 (inclusive of values between those provided here). In one embodiment of the copolymer useful in humans or animals, the copolymer has a lower critical solution temperature below 37° C. For veterinary applications, the LCST can be slightly higher as the core body temperature of certain animals (e.g., cats, dogs, horses, cows, sheep and goats) is in the range of 38° C.-39° C. In another embodiment, the copolymer has a lower critical solution temperature above 37° C. after its backbone ester linkages are hydrolyzed (substantially hydrolyzed, as with treatment of the polymer with NaOH, as described herein).

In medical or veterinary uses, the copolymers and compositions comprising the copolymers may serve, for example, as adhesives or fillers. They may be applied to wounds or into body cavities or used as a tissue packing to apply compression. As such, embodiments of the copolymer solutions described herein may be applied to wounds and, in one embodiment covered, optionally with a warming compress or "heat pack" for example as are available commercially to ensure that the copolymer is maintained at a temperature above its LCST and thus remains gelled when in contact with any cooler areas of the body, typically the skin. As a hydrogel, embodiments of the copolymers disclosed herein may be contained in a composition comprising the copolymer and an aqueous solution that does not interfere substantially with the LCST and polymer structure in its intended use. For instance, the composition may comprise any aqueous solvent, optionally pharmaceutically acceptable, including, without limitation, water, PBS, Saline, etc. As used herein, and "aqueous solvent", is an aqueous solution compatible with the copolymer which can be absorbed into the copolymer matrix. The composition also may comprise an active agent, biological or drug, such as, without limitation: antibiotics, clotting agents (without limitation, an antifibrinolytic, such as desmopressin/DDVAP), analgesics, anesthetics, antiseptics, anti-inflammatory agents, chemotherapeutic agents, metabolites, rheology modifiers, cytokines, chemoattractants, hormones, steroids, proteins (including enzymes), nucleic acids, cells, virus particles, nucleic acids, biomatrices or precursors thereof, or a foaming agent. In one embodiment, the composition comprises stem cells (such as adipose-derived stem cells) or other progenitor cells so that the composition is useful as a biodegradable tissue engineering scaffold. The composition, even without cells, is useful as a cell growth niche or scaffolding into which cells such as native stem/progenitor cells can migrate in situ. In such an embodiment, chemokines, cellular growth agents and cellular differentiation agents can be included within the composition to attract cells into the composition and promote cellular growth and differentiation when placed in situ.

According to one embodiment, in its application to wound treatment, a clotting agent such as desmopressin may be included in a polymer composition. An appropriate, e.g., pharmaceutically acceptable, foaming agent as are well-known in the relevant arts also may be included for the purpose of creating compression in a wound, whether exposed to a body surface in the case of (for example) puncture wounds or bullet wounds, or internal wounds, in which case, the polymer can be injected into or near a site of internal bleeding. As such, the composition can find use in many situations, ranging from home use to stabilization of bleeding or massively bleeding patients in emergency and battlefield situations. The copolymer also can be used during surgical procedures to apply compression and otherwise secure a site of injury, such as a portion of a patient's intestine, nasal passage or sinus cavity where a tumor or polyp has been removed or after other surgeries. The benefits of such a reversibly-gelling copolymer composition is that the composition can be removed simply by cooling, for example and without limitation, by flushing with cool (lower than the copolymer's LCST) flushing solution, such as water, saline or phosphate-buffered saline. Thus, while a wound and bleeding in a patient can be stabilized by application of the polymer, the polymer can be selectively eroded in an emergency room or during surgery simply by flushing with a cool (for example and without limitation, 0° C. to 30° C.) saline solution.

In another embodiment, the composition as substantially described above, comprising as copolymer having a LCST of 37° C., is injected into tissue at the site of an injury or defect to provide support and/or provide a scaffold for infiltration of cells. The composition as injected may optionally include cells, growth factors, drugs, and the like, as provided elsewhere in this disclosure. In certain embodiments, the copolymer may have an LCST of, for example 36° C. or lower, 35° C. or lower, 34° C. or lower, or, in another embodiment between 10° C. and 34° C., including increments and sub-ranges therebetween, and in another embodiment, less than 20° C.

In certain embodiments, the composition is injected into the heart, to treat a heart defect. In some embodiments, the composition is injected into myocardial tissue, at the site of a myocardial defect. In some embodiments, the myocardial defect is necrotic tissue. In some embodiments, the necrotic myocardial tissue is an infarct that is the result of a myocardial infarction. Those of skill in the art will understand and appreciate that the composition described above is suitable for such therapeutic uses because of its characteristics, specifically its flowable, liquid nature at room temperature (or below the temperature of the human body), and gel-like nature at physiological temperatures (such as 37° C.). Thus, a practitioner may deliver the proper amount of the composition with precision, and without the worry of the composition "running" into areas where it is not wanted or needed.

In a further embodiment, the composition serves as a cell growth medium. According to one embodiment, cells are introduced into a composition comprising a copolymer as described herein to produce a cell construct. The cell construct is incubated under conditions suitable for growth of the cells. That is, the cell construct can be placed in an incubator or into a patient so that the cells are maintained under adequate environmental conditions to permit the cells to survive, proliferate, differentiate and/or express certain products. "Cell growth" means that the cells survive and preferably, though not exclusively, divide and multiply. The composition may comprise cell growth media, which typically provides necessary nutrients and environmental conditions for cell growth. The cells may be introduced and incubated under conditions suitable for cell growth by introducing the composition into a patient and allowing native cells, such as stem cells to migrate into the composition. The composition can be administered by injecting the composition into the region requiring cellular growth or remodeling, such as a region of damaged tissue.

In one non-limiting example, the damaged tissue is within the cardiac wall caused by a myocardial infarction and the composition is injected into the cardiac wall. In one variation of that embodiment, cytokines, chemoattractants, nutrients and/or cell differentiation factors, such as one or both of bFGF and IGF-1, are included in the composition. The composition optionally contains one or more of an antiseptic, an analgesic, an anesthetic and an antibiotic (for example, for selection of the cells or to prevent bacterial growth in the composition). To facilitate cell growth, in one non-limiting embodiment, the copolymer is conjugated with collagen, for example between 0% and 10% by weight of the copolymer of collagen.

A current broadly pursued approach to treating ischemic cardiomyopathy is cellular transplantation into the infarct or border zone region to improve regional and global pump function. Cells such as skeletal myoblasts, bone marrow stromal cells, endothelial precursor cells and embryonic stem cells have been injected into injured myocardium. These studies report mixed results, with modest attenuation of progressive loss of ventricular function primarily observed in terms of maintaining or increasing LV wall thickness and fractional shortening. The mechanism behind these beneficial results is controversial, although several have suggested that the transplanted cells led to regeneration of contractile myocardial tissue. Increasingly, however, it is believed that the positive results are derived from cell-associated angiogenic effects or cytokine-mediated reduction in apoptosis rather than myocardial regeneration by the transplanted cells. In 2006, a report by Wall et al. argued that the positive results of these cell therapy studies might simply be attributable to the mechanical effects associated with the injection of fluid volume (cells and delivery vehicle) into the LV wall. The injected volume would change the LV geometry and thus modify the mechanics inside the LV wall, leading to a reduction of elevated local wall stresses in the infarct border zone and preventing the pathological remodeling in the post-infarct heart. This hypothesis was supported with a finite element analysis that modeled the local systolic fiber stress distribution in an infarcted LV wall injected with a mechanically passive material. The simulation showed that injection of a volume 4.5% that of the total LV wall volume and a stiffness (elastic modulus) 20% of the natural LV tissue into the infarct border zone could decrease the fiber stress by 20% compared to a control simulation in which there was no injection. The mechanical simulation also showed that this attenuating effect on LV wall stress increased with the injection volume and modulus of the injected material. This report thus provides the basis for the local treatment of the failing cardiac wall with biomaterial-based injection therapy. The stress reduction potential of the injected material is of great relevance since in a dyskinetic transmural infarct, the elevated stresses in the infarct border zone region are thought to contribute to pathological remodeling in the post-infarct heart. Reducing these stresses may in turn minimize stress-induced apoptosis and border zone expansion, reducing further remodeling and preventing progression to congestive heart failure.

Both naturally derived and synthetic materials, including alginate, fibrin, alginate-fibrin composites, collagen, chitosan, self-assembling peptides, self-assembling polymers, and thermoresponsive dextran-poly(N-isopropylacrylamide) (PNIPAAm) composites, have recently been utilized for cardiac wall injection therapy in animal models with reported benefits in terms of attenuated decrease in wall thickness and infarct expansion in most cases, and in a few cases improved LV functions. Alginate has been shown to have a beneficial effect in terms of attenuating the decrease in wall thickness and infarct expansion, but recent reports injecting adhesion peptide modified alginate demonstrate no clear benefit of such modification. Self-assembling peptides carrying specific growth factors have been reported to have positive effects on the cardiac wall remodeling process and have also been reported as vehicles for the transplantation of cardiomyocytes into the cardiac wall. Regarding thermoresponsive polymers, a recent report showed that injection of a dextran-poly(NIPAAm) composite 4 days following MI in a rabbit model prevented adverse cardiac remodeling and dysfunction 30 days following treatment.

In considering all of the biomaterials that have been utilized in these early investigations of cardiac injection therapy, it is encouraging that some positive benefits have been observed in the animal models studied. However, the materials investigated to date have not been optimal for the cardiac injection application and that most investigators have utilized "off the shelf" materials (alginate, fibrin, collagen, chitosan) or synthetic hydrogels that do not display the degradation or mechanical profile that would be most desirable for this setting. Only short term effects have been reported in the literature, perhaps since the injected materials are rarely detectable in vivo after 6 wk. Although mechanical properties of the injection material have been shown to be important in mechanical modeling, these properties have notably not been characterized and discussed in the early reports where cardiac injection therapy has been investigated. In terms of the animal models that have been evaluated, in most reports LV injections were made within 1 wk of infarction, in the acute, necrotic phase. Waiting longer, even to the point of 2 wk post-MI would have greater relevance, since this time would more closely correspond to the beginning of the fibrotic phase of remodeling, after the necrotic phase. Such a time lag may better represent infarcts that would be encountered in patients with sub-acute MI, where the patient may not present clinically until substantial wall remodeling has already occurred.

In the example of infarcted myocardium, in addition to the mechanical benefits associated with injections of the copolymer compositions described herein into the infarcted myocardium, the inclusion of bioactive growth factors in the delivered material for controlled temporal release offers another mechanism by which injection therapy might lead to more functional LV remodeling. Many growth factors such as basic fibroblast growth factor (bFGF), platelet derived growth factor (PDGF), hepatocyte growth factor (HGF), vascular endothelial growth factor (VEGF) and others have been injected into the myocardium following infarction and have elicited improvements in cardiac angiogenesis, ejection fraction, and cellular activity in the form of mitogenesis and motogenesis. Injection of fluid concentrated with growth factors has been shown to have the same capacity to significantly improve cardiac function as injection of stem cells. Delivering multiple growth factors has also been shown to have advantages over the presentation of a single factor. For example, cardiac injection of an alginate material designed to release VEGF followed by PDGF showed increased alpha smooth muscle cell vessel density than the delivery of either growth factor alone. Bimodal delivery systems may seek to mimic the native kinetics of growth factor delivery wherein the stimulation and development of one system prior to another may be beneficial—in the example mentioned the development first of a primary vascular network from endothelial cells provided a foundation for recruiting smooth muscle cells to mature and stabilize that network.

Two particularly important growth factors studied in the context of cardiac remodeling have been bFGF and insulin-like growth factor-1 (IGF-1). IGF-1 has been shown to have significant cardioprotective, inotropic, and regenerative capabilities and to be a potent recruiting factor for stem cells. IGF-1 also leads to increased Akt signaling in cells which can lead to production of other growth factors including VEGF and angiopoietin-2. Local IGF-1 delivery to injured myocardium has been linked to decreased apoptosis, increased cell growth, and improved systolic function. As such, controlled IGF-1 delivery may be useful to improve heart function simultaneously with injected material. A growth factor with effects complementing IGF-1 is bFGF. This potent angiogenic factor strongly increases both endothelial and smooth muscle cell proliferation, and has been linked to increased cardiomyocyte mitotic activity. Increased regional blood flow in the infarcted heart has been shown as long as 6 months after a single intramyocardial injection of bFGF. Importantly, from a functional standpoint, left ventricular ejection fraction has been increased in infarcted hearts supplied with bFGF. Due to the short half-life of bFGF in vivo, controlled release from biomaterial carriers has been shown to be an appropriate delivery method to increase cardiac regeneration. Using a bimodal delivery system of bFGF followed by IGF-1 may provide a vascular network to which stem cells can be recruited followed by increased proliferation with an improved local vascular network.

In addition to the above description of cardiac uses of the copolymers described herein, there are numerous other uses for supplementing and/or enhancing repair of other muscle tissues. Those of ordinary skill in the art will appreciate that the presently disclosed copolymers will be suitable for numerous applications where biocompatible gels may be useful.

Compositions comprising a copolymer described herein can be distributed for use in any suitable vessel. In one instance, the composition is packaged in a sealed container, from which the composition can be poured, squeezed or otherwise decanted, for example and without limitation, by use of a syringe. The vessel can be a bag, such as an IV bag. In another embodiment, the composition can be distributed in a syringe for immediate dispensation into a wound or body cavity/location. A syringe can be fitted with any type of needle, tip, tube, balloon device or other useful fitting for facilitating accurate placement of the solution in or around a desired delivery site, for example and without limitation, for delivery into the large intestine of a patient after removal of a tumor. In another embodiment, the composition and a pharmaceutically acceptable solvent is stored within a syringe at or below 4° C. and the syringe is fitted with a needle gauge sufficient to allow for injection without increased pressure but also prohibit back flow of the solution into the syringe after injection, such as, without limitation, a 16G through 23G (gauge) needle, and in certain embodiments an 18G or 20G needle. As described below and in the Examples, a robotic injection device can be used to deliver any of the compositions described herein to the heart or other organs or tissue. Thus, methods of use embodying the above-described uses for a copolymer described herein and compositions comprising the copolymer are contemplated and embraced as part of the present invention.

In the context of myocardial infarction, although myocardial injection therapy is currently dominated by trans-catheter endocardial approaches, direct epicardial injection offers potential advantages such as easy detection of target myocardial infarct lesions, decreased likelihood of cerebrovascular complications, and superior site specific efficacy. Particularly with gel materials, the risk of backflow and embolization from an endocardial injection site is a serious concern. To date, a major limitation of direct epicardial injection is the lack of dedicated minimally invasive access technology, generally causing it to be performed only in conjunction with other procedures using sternotomy or thoracotomy, both of which have high associated morbidity. In addition, the instrumentation used in most reported applications does not readily accommodate the motion of the beating heart, and therefore does not facilitate precise placement and depth of injections. A dedicated technology for precise interaction with the heart from within the intrapericardial space that balances treatment efficacy and minimal invasiveness is likely to provide a future clinical benefit for the hydrogel injection therapy proposed here and for myocardial injection-based therapies in general. To address this need, we have developed a novel miniature robotic device (HeartLander, see, e.g., US Patent Publication No. 20050154376, incorporated herein by reference in its entirety) that navigates over the epicardial surface to per-form minimally invasive myocardial injections on the beating heart through a subxiphoid approach. Such injections have been achieved in vivo in a porcine model, demonstrating positioning accuracy of 1.7±1.0 mm in applying multi-target injection patterns.

In another use, a composition described herein can be used for cosmetic purposes, such as for a rheology modifier. Ingredients, including without limitation colorants, fragrances, flavors, and other ingredients listed herein, including active agents, may be included in the composition.

The following examples are provided for illustration purposes and are not intended to limit the scope of the present invention. Reference is made to International Patent Publications: WO 2008/045904 and WO 2010/127254, for the disclosure of the general process of making, and characteristics of, various copolymers. The disclosures of WO 2008/045904 and WO 2010/127254 are incorporated herein by reference in their entirety.

EXAMPLES

A hydrogel possessing thermoresponsive behavior coupled with robust mechanical properties suitable for soft tissue engineering is of great interest. Such a thermoresponsive scaffold could readily encapsulate and deliver cells for subsequent mechanical training in vivo or in vitro. Described herein and in the examples below is a family of injectable and flexible hydrogel composites based on thermosensitive copolymers, optionally conjugated with collagen. The compositions find use in, for example cardiac remodeling after myocardial infarction. These novel thermosensitive, biodegradable and flexible hydrogels have properties attractive for future application in soft tissue engineering.

Example 1: A Thermally Responsive Injectable Hydrogel Incorporating Acrylic Acid—Poly(Trimethylene Carbonate) for Hydrolytic Lability Thermally responsive injectable and bioabsorbable hydrogel by copolymerization of N-isopropylacrylamide (NIPAAm), acrylic acid (AAc), and biodegradable monomer hydroxyethyl methacrylate-poly(trimethylene carbonate) (HEMAPTMC) is synthesized and evaluated. The study sought to investigate and tune the molecular design by altering the relative amount of AAc so that a thermoresponsive hydrogel would be achieved with an LCST below body temperature prior to hydrolysis of the poly(trimethylene carbonate) (PTMC) branches, but with an LCST that rose above body temperature with PTMC cleavage. The HEMAPTMC component was selected and synthesized for use since the carbonate bond in PTMC should have a hydrolysis rate that would allow retention of the gel over the several week period that are hypothesized as being necessary for the cardiac application in vivo. After characterizing and optimizing the copolymer structure, the optimized hydrogel was evaluated by injection into chronic rat myocardial infarctions two weeks following coronary ligation, and the resulting cardiac performance and ventricular remodeling were assessed over an 8 week period. The hypothesis was that injection of the designed thermoreponsive hydrogel would alter the progression of ventricular remodeling, preserving ventricular wall thickness and maintaining contractile function.

Chemicals were purchased from Sigma-Aldrich unless otherwise stated. NIPAAm was purified by recrystallization from hexane and vacuum dried. NIPPAm (50 g) was dissolved into 150 mL hexane at 80° C. and then recrystallized at room temperature. AAc and 2-hydroxyethyl methacrylate (HEMA) were purified by vacuum distillation at 70° C. and 100° C., respectively. Benzoyl peroxide (BPO), stannous 2-ethylhexanoate [$Sn(OCt)_2$], trimethylene carbonate (TMC, Boehringer Ingelheim Chemicals Inc.) were used as received.

Synthesis of HEMA-polyTMC (HEMAPTMC)

HEMAPTMC was synthesized by ring-opening polymerization of TMC initiated by HEMA with $Sn(OCt)_2$ as a catalyst (FIG. 1). Stoichiometric amounts of HEMA and TMC (molar ratio 1:2) were mixed in a flask to which was added anhydrous toluene of equal mass to the TMC/HEMA mixture. $Sn(OCt)_2$ (1 mol % with respect to HEMA) in 1 mL toluene was subsequently added. The reaction was conducted at 120° C. for 1.5 h. The mixture was then dissolved in THF and precipitated in water. This precipitation process was repeated twice and the liquid precipitate was then isolated by centrifugation, dissolved in THF, and dried over anhydrous MgSO4. THF was removed by rotary evaporation.

Synthesis of Poly(NIPAAm-co-AAc-co-HEMAPTMC)

Poly(NIPAAm-co-AAc-co-HEMAPTMC) copolymers were synthesized by free radical polymerization (FIG. 1). Monomers (NIPAAm, AAc, HEMAPTMC) were dissolved in 1,4-dioxane to form a 5 wt % solution containing BPO ($7.2 \times 10^{-3}$ mol/mol monomer). The polymerization was carried out at 70° C. for 24 h under argon atmosphere. The copolymer was precipitated in hexane and further purified by precipitation from THF into diethyl ether. The purified copolymer was vacuum dried.

Results

Synthesis of HEMAPTMC and Copolymer

The synthesis of HEMAPTMC was confirmed by the 1H-NMR spectrum of the product (data not shown) and the $^{13}$C-NMR spectrum (data not shown) containing proton peaks and carbon peaks in agreement with the molecular structure of HEMAPTMC. In the $^1$H-NMR spectrum, HEMA alone would be expected to have two characteristic triple peaks centered at 4.4 ppm and 3.9 ppm for d protons, while for HEMAPTMC the combination of the two d peaks into a single peak at 4.4 ppm provides confirmation of the formation of HEMAPTMC. The chemical structure of HEMAPTMC was further confirmed by the mass spectrum (API-ES positive). Peaks at 254.8 (HEMAPTMC1+Na$^+$), 357.0 (HEMAPTMC2+Na$^+$), 459.0 (HEMAPTMC3+Na$^+$), 561.0 (HEMAPTMC4+Na$^+$) and 663.0 (HEMAPTMC5+Na$^+$) were observed, indicating that the product was a mixture of molecules containing different PTMC lengths (data not shown). The number average length of PTMC units per monomer was determined from $^1$H-NMR spectrum as 2 by calculation from the ratio of the integrals of hydrogen peaks from PTMC and the double bond hydrogen (CH$_2$=) peak. This PTMC unit number for HEMAPTMC was in agreement with the molar feed ratio of HEMA to TMC (1:2) in the synthesis of HEMAPTMC.

Copolymers with different monomer ratios were prepared by free radical polymerization (FIG. 1). Table 1 (below) summarizes poly(NIPAAm-co-AAc-co-HEMAPTMC) copolymers synthesized with different AAc feed ratios. All of the copolymers have molecular weights between 20 k and 30 k, and a polydispersity index of 1.5~2.0. The existence of AAc (—COOH) units in the copolymer was verified and quantified by titration of the polymer solution with NaOH solution (0.1 M) (data not shown). The AAc content obtained by the titration method and the integration ratios of characteristic proton peaks in the $^1$H-NMR spectra were used to determine copolymer compositions (Table 1 below). The monomer compositions in the copolymers were found to be close to the feed ratios, with a consistent slight reduction in the measured AAc content from that expected based on the feed ratio.

tion therapy where increased mechanical strength and relatively slow resorption rates would be attractive.

Materials and Methods

All chemicals were purchased from Sigma-Aldrich unless otherwise stated. NIPAAm was purified by recrystallization from hexane and vacuum dried. 2-hydroxyethyl methacry-

TABLE 1

Properties of poly(NIPAAm-co-AAc-co-HEMAPTMC) copolymers with different feed ratios of AAc.

| Feed ratio NIPAAm/AAc/ HEMAPTMC | Yield | Mn g/mol | Mw/Mn | —COOH content, $10^{-4}$ mol/g | Polymer composition, NIPAAm/AAc/ HEMAPTMC | 37° C., 16.7 wt % in PBS, pH 7 | LCST 16.7 wt % in PBS, pH 7, ° C. |
|---|---|---|---|---|---|---|---|
| 87/3/10 | 86% | 27,000 | 1.8 | 1.6 | 88.5/2.1/9.4 | solid gel | 29.1 ± 0.37* |
| 86/4/10 | 87% | 23,000 | 1.9 | 2.6 | 88.3/3.3/8.4 | solid gel | 33.1 ± 0.43* |
| 85/5/10 | 84% | 34,000 | 1.5 | 2.8 | 87.0/3.6/9.4 | cloudy, weak gel | 36.2 ± 0.38* |
| 84/6/10 | 93% | 21,000 | 2.0 | 3.8 | 86.2/4.8/8.9 | clear solution | 44.5 ± 0.10* | p < 0.001 versus each of other copolymers

Gelation Properties, the LCST and Optimization of Monomer Feed Ratio

The qualitative gelation properties of the poly(NIPAAm-co-AAc-co-HEMAPTMC) copolymers are summarized in Table 1 (above). When the AAc feed ratio was 3% and 4%, a solid gel could be formed at 37° C. When the AAc feed ratio was increased to 5%, a fluid-like hydrogel with negligible strength was formed. When the AAc feed ratio was as high as 6%, the copolymer solution remained a clear solution at 37° C., indicating an LCST above 37° C. The calculated LCSTs were determined from the optical data (not shown). The temperature at which optical absorption rapidly transitions (the LCST) is seen to increase as the AAc feed ratio of the copolymer is increased. While copolymers with AAc feed ratios of 3, 4 and 5% had LCSTs below 37° C., the copolymer with an AAc feed ratio of 6% had an LCST of 45° C.

Example 2: A Thermally Responsive Injectable Hydrogel Incorporating Methacrylate-Polylactide for Hydrolytic Lability Methacrylate-polylactide (MAPLA), with an average 2.8 lactic acid units, was synthesized and copolymerized with n-isopropylacrylamide (NIPAAm) and 2-hydroxyethyl methacrylate (HEMA) to obtain bioabsorbable thermally responsive hydrogels. Poly(NIPAAm-co-HEMA-co-MAPLA) with three monomer feed ratios (84/10/6, 82/10/8 and 80/10/10) was synthesized and characterized with NMR, FTIR and GPC. The copolymers were soluble in saline at reduced temperature (<10° C.), forming clear solutions that increased in viscosity with the MAPLA feed ratio. The copolymers underwent sol-gel transition at lower critical solution temperatures of 12.4, 14.0 and 16.2° C. respectively and solidified immediately upon being placed in a 37° C. water bath. The warmed hydrogels gradually excluded water to reach final water contents of ~45%. The hydrogels as formed were mechanically strong, with tensile strengths as high as 100 kPa and shear moduli of 60 kPa. All three hydrogels were completely degraded (solubilized) in PBS over a 6-8 month period at 37° C., with a higher MAPLA feed ratio resulting in a faster degradation period. Culture of primary vascular smooth muscle cells with degradation solutions demonstrated a lack of cytotoxicity. The synthesized hydrogels provide new options for biomaterial injeclate (HEMA) was purified by vacuum distillation. Lactide was purified by recrystallization from ethyl acetate. Benzoyl peroxide (BPO), sodium methoxide (NaOCH$_3$) and methacryloyl chloride were used as received.

Synthesis of Methacrylate Polylactide (MAPLA)

Figure 2:
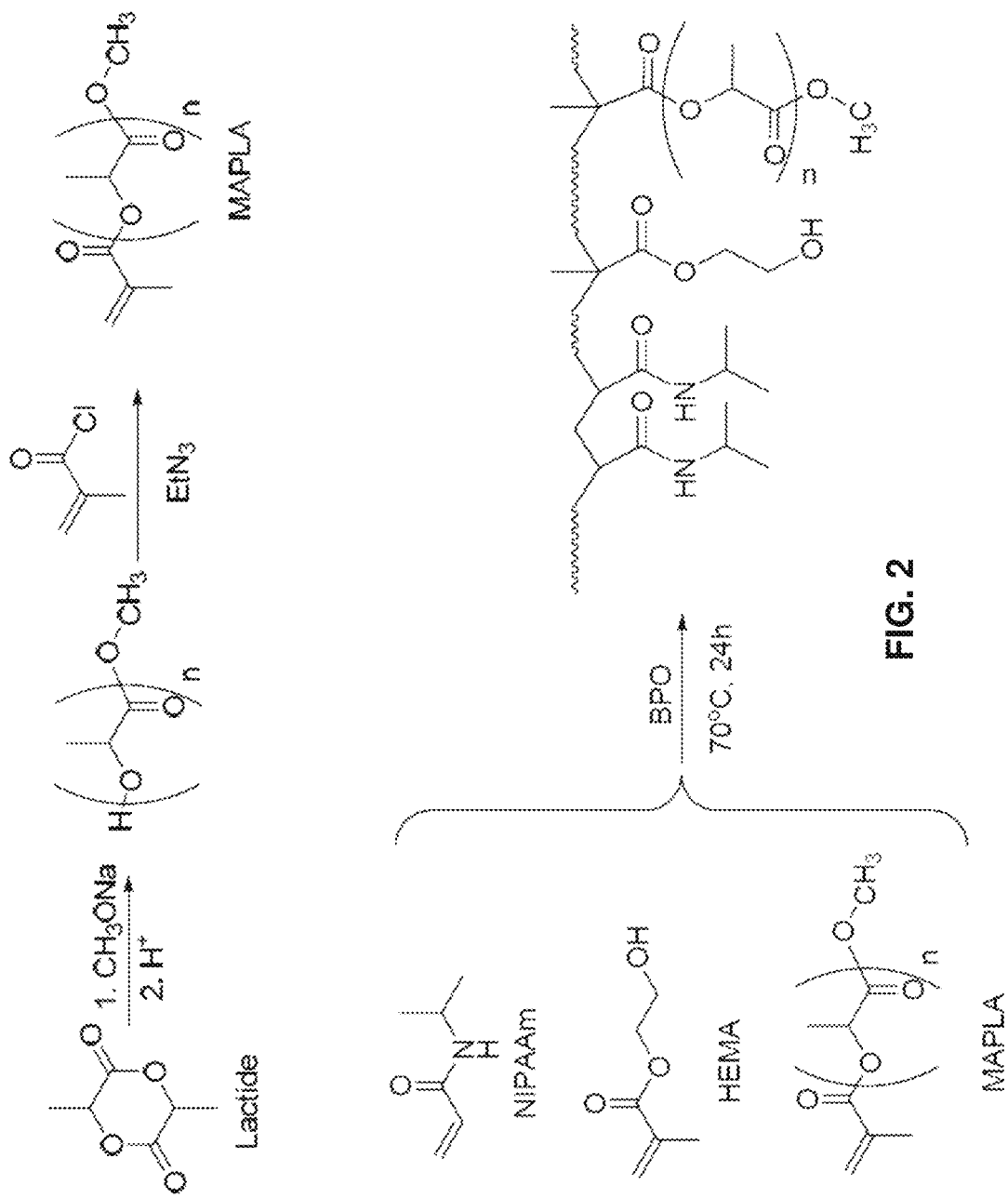
FIG. 2. Synthetic scheme for MAPLA and poly(NIPAAm-co-HEMA-co-MAPLA).

As shown in FIG. 2, polylactide (HO-PLA-OCH$_3$) was synthesized by NaOCH$_3$ initiated ring opening polymerization of lactide. In a lactide solution in dichloromethane a solution of NaOCH$_3$ in methanol (10% wt/v) was added with a molar ratio of (NaOCH$_3$+HOCH$_3$) to lactide of 1:1, under vigorous stirring. The reaction proceeded for 2 h at 0° C. before the solution was rinsed with 0.1M HCl and deionized (DI) water. The organic phase was isolated by centrifugation and dried over anhydrous MgSO$_4$. The solvent (dichloromethane) was removed by rotary evaporation at 60° C. to obtain HO-PLA-OCH$_3$. Biodegradable monomer MAPLA was synthesized by dropping equimolar amounts of methacryloyl chloride into the HO-PLA-OCH$_3$ solution in dichloromethane in the presence of equimolar amounts of triethylamine. After reacting at 0° C. overnight, the solution was filtered to remove precipitants, and was then rinsed sequentially with 0.2M Na$_2$CO$_3$, 0.1M HCl and DI water. The organic phase was isolated by centrifugation and dried over anhydrous MgSO$_4$. The solvent (dichloromethane) was removed by rotary evaporation at 40° C. to get the raw product of MAPLA, which was finally purified by flash chromatography.

Synthesis of Poly(NIPAAm-co-HEMA-co-MAPLA)

Poly(NIPAAm-co-HEMA-co-MAPLA) copolymers were synthesized by free radical polymerization (FIG. 2). Monomers (NIPAAm, HEMA, MAPLA) were dissolved in 1,4-dioxane to form a 5 wt % solution containing BPO ($7.2 \times 10^{-3}$ mol/mol monomer). The polymerization was carried out at 70° C. for 24 h under argon atmosphere. The copolymer was precipitated in hexane and further purified by precipitation from THF into diethyl ether and vacuum dried.

Figure 3:
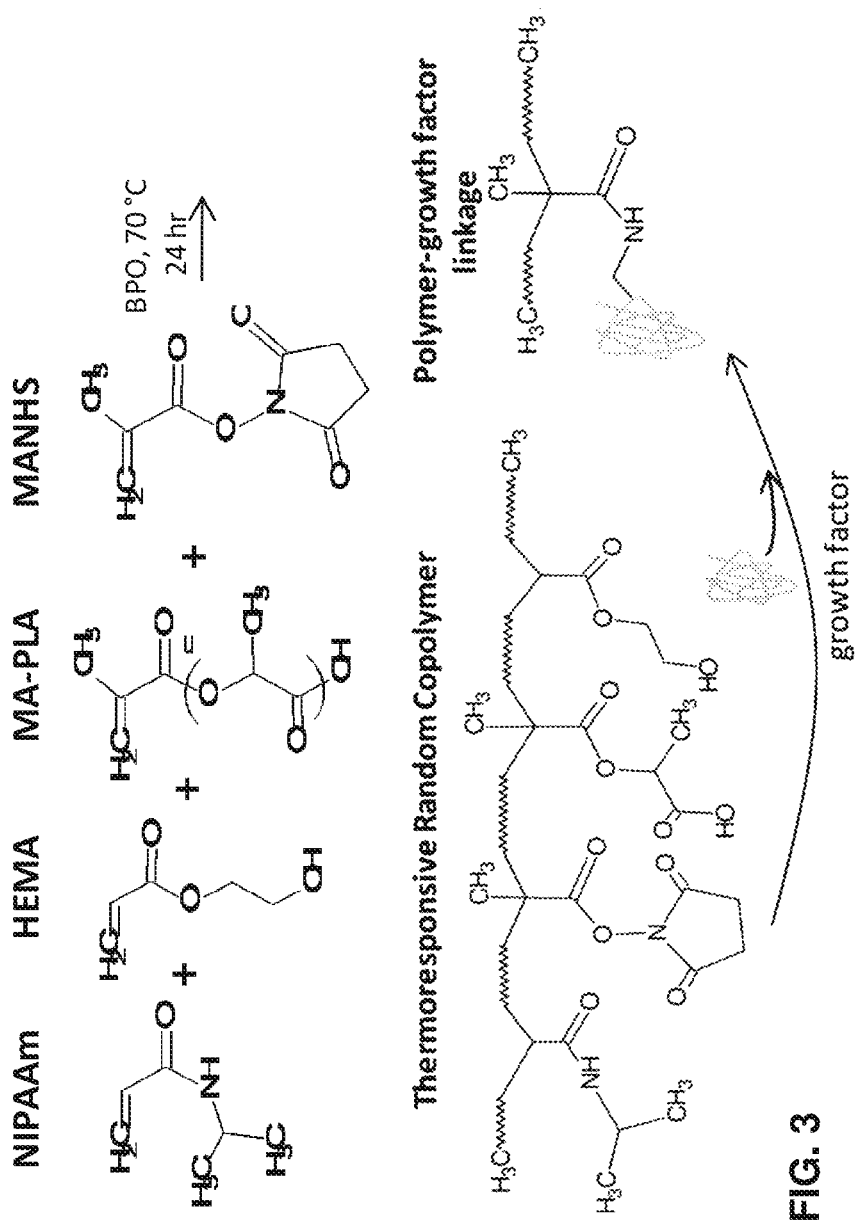
FIG. 3. Synthesis of poly(NIPAAm-co-HEMA-co-MANHS-co-MAPLA) and subsequent reaction of the MANHS mer with growth factor.

Example 3: Design Rationale and Characterization of Poly(NIPAAm-co-HEMA-co-MANHS-co-MAPLA)+/−Growth Factors In order to provide the capacity for controlled release of bioactive factors from the injected hydrogels, the design of poly(NIPAAm-co-HEMA-co-MAPLA was modified to create poly(NIPAAm-co-HEMA-co-MANHS-co-MAPLA by incorporating the monomer N-hydroxysuccinimide methacrylate (MANHS) (FIG. 3). This monomer has the ability to readily react with primary amine groups (e.g. surface lysines in proteins) forming a stable amide bond and provides a means for covalent growth factor attachment to the copolymer in an aqueous environment. The covalent link reduces the burst release often encountered with hydrogel systems. This attachment technique was applied previously, where poly(NIPAAm-co-AAc-co-HEMAPTMC) was used but with the addition of N-acryloxy succinimide (NAS) to bind IGF-1. The results showed IGF-1 was successfully bound to the hydrogel and remained bioactive upon release. As discussed, however, poly(NIPAAm-co-AAc-co-HEMAPTMC) does not have the mechanical strength and decreased degradation rate advantages of poly(NIPAAm-co-HEMA-co-MAPLA). MANHS may be desirable over NAS for this application since the succinimide ester reactivity with water is slower for MANHS, ultimately favoring amine reaction and higher loading efficiency. In preliminary studies 1 mol % MANHS has been incorporated in the polymer feed to make poly(NIPAAm-co-HEMA-co-MANHS-co-MAPLA) (Mw 25 kD, Mw/Mn~1.5) that was subsequently loaded with protein at a loading efficiency of 46%. The majority of protein was delivered in vitro from poly(NIPAAm-co-HEMA-co-MANHS-co-MAPLA) in the first week followed by near zero-order release extending for 3 months related to polymer degradation. Because we ultimately seek a hydrogel system with bi-modal release, with bFGF delivery occurring before IGF-1, we will take advantage of the higher early release rates and use this covalent attachment system with bFGF.

Several design parameters of poly(NIPAAm-co-HEMA-co-MANHS-co-MAPLA) can be altered to influence protein release kinetics. In one example, the relative amount of MANHS incorporated into the copolymer, which determines protein binding capacity, is varied between 1-5 mol %. Increasing MANHS content not only has the potential to increase protein binding but can also be used to speed polymer degradation and thus protein delivery rate. In addition to this parameter the amount of bFGF loaded can be varied. Both parameters will influence the release profile of the protein. While studies to date have not specifically investigated the influence that burst release has on the angiogenic effects of delivered bFGF, some conclusions can be made based on direct injection studies. It has been shown that when a solution of free bFGF is injected directly into the myocardium only 16% remains after one hour. While some cardiac improvements have been shown from this delivery method, additional benefits of bFGF delivery with a carrier have been demonstrated. Delivery of bFGF from microspheres and gel systems over a range of 1-6 wk resulted in substantial vascular and functional improvements. The amount of bFGF remaining at the injection site 72 h after injection was roughly 30% when the factor was incorporated into gelatin microspheres—a 15× increase compared to free bFGF injection. As an example, the design of poly(NIPAAm-co-HEMA-co-MANHS-co-MAPLA) is manipulated with the objective of >70% release over the first 2 wk, with continued delivery for at least 6 wk.

Studies have also shown that improvements to cardiac function and blood flow in rats can be elicited when between 10 and 100 µg of bFGF is delivered, providing an exemplary range of bFGF loading concentrations that can be characterized in vitro. While there is concern that excessive bFGF delivery might lead to hemangioma formation, bFGF administration in this range has not been associated with this complication in animal studies.

In another example microparticle carriers, which offer an extended release profile, are employed as a protein delivery mechanism. Combining a suspension of growth factor-loaded (or other active agent-loaded) microparticles in solution with the protein-conjugated poly(NIPAAm-co-HEMA-co-MANHS-co-MAPLA) permits delivery of a second growth factor, where each delivery system—covalent hydrogel attachment or microparticulate—has distinct design parameters to influence release kinetics which are largely independent of the other. Microparticles of many common biomaterials such as gelatin, collagen, alginate, and poly(lactic-co-glycolic) acid (PLGA) have been synthesized and used for drug delivery with positive results. With poly(NIPAAm-co-HEMA-co-MANHS-co-MAPLA). In an example, relatively hydrophobic PLGA microparticles are utilized since they will interact with the hydrophobic NIPAAm groups in the collapsed hydrogel, thus precluding their exclusion from the gel network during phase transition. As an example, a double emulsion system is used to form these microparticles with IGF-1 loading in a manner to protect against protein denaturation, as previously described. It has been shown that appropriately designed microparticles can deliver growth factor at a slower rate with a smaller burst than the covalent system above. PLGA (75:25, 100 kDa) microparticles (49 um diam) encapsulating BSA have been synthesized and protein release rates measured after particle mixing with poly(NIPAAm-co-HEMA-co-MAPLA). Inclusion of protein-loaded PLGA microparticles in a hydrogel system has previously been shown to nearly eliminate burst release leading to delayed protein delivery. The results agree, showing only 4% burst release of total protein during gel formation, and only 15% released by 2 wk. This release rate is about one-third of that from the same microparticles not within a hydrogel. Later-stage protein release follows the degradation of the PLGA microparticles which increases after 4 wk in saline. A biphasic system is thus achievable wherein the majority of bFGF is released early from the hydrogel carrier followed by IGF-1 release later as the PLGA microparticles within the gel degrade. As has been shown previously, the burst and duration of protein release from PLGA microparticles can fall within a wide range depending on controllable factors such as polymer weight fraction in the microparticles, particle size, degradation time, and weight fraction of growth factor. One exemplary design objective for microparticles is <20% release in the first 2 wk, with an additional 60% over the 4 wk following. Since a dose range from 25 ng to 100 µg of IGF-1 has shown functional cardiac improvements in rats, a moderate total dose between 1-10 µg is used.

Hydrogel chemical structure is characterized with NMR, FTIR, and mass spectra. Molecular weight is determined by gel permeation chromatography. The LCST of the hydrogel solutions is determined by DSC, UV-optical absorption with temperature scanning and rheological testing with temperature scanning. Hydrogel solution viscosity below the LCST is measured with rheometry and gelation speed at 37° C. is quantified by plotting water content over time. Tensile and rheological testing provides hydrogel mechanical properties. Polymer degradation product cytotoxicity is assessed by the metabolic viability of cells cultured with medium supplemented with degradation products. Cells also are observed under fluorescence microscopy after live/dead staining when cultured atop the hydrogels. For controlled release from poly(NIPAAm-co-HEMA-co-MANHS-co-MAPLA), the attachment of bFGF to the polymer is investigated with matrix assisted laser desorption ionization (MALDI) mass spectrometry. Release kinetics of each growth factor from its polymer carrier is analyzed by enzyme-linked immunosorbant assay for the specified protein. To quantify bioactivity of the released bFGF and IGF-1 cell proliferation assays with L929 fibroblasts and MG-63 cells are used, respectively with calibration to known growth factor concentrations. Failure to meet the stated design objectives for poly (NIPAAm-co-HEMA-co-MAPLA) and poly(NIPAAm-co-HEMA-co-MANHS-co-MAPLA) results in iterative material design refinement and characterization using the controllable parameters discussed above.

Example 4—Tailoring the Degradation Rates of Thermally Responsive Hydrogels Designed for Soft Tissue Injection by Varying the Autocatalytic Potential Appropriate biomaterial degradation behavior is essential for obtaining desired therapeutic outcomes in a variety of tissue engineering and regenerative medicine applications. Biomaterial degradation theoretically should be aligned with the pace of cell infiltration and neo-tissue formation to allow the structural and functional integration of host tissue with tissue developed in the region of the implanted biomaterial. For example, rapid degradation of dermal grafts may favor a fibrotic response over a more constructive regeneration outcome. Uncoordinated absorption of bone substitutes can cause mechanical mismatch and ultimately contribute to failure in load bearing. In biodegradable arterial stent development, there is interest in assuring that the stent remains long enough to remodel the vascular wall in a stable fashion, but not much longer to avoid complications associated with a permanent foreign body in the vascular wall.

Thermally responsive hydrogels have been widely studied for their amenability to minimally invasive delivery in the realms of drug delivery, embolization therapy, cell delivery vehicles, tissue fillers and wound dressings. More recently, intramyocardial injection therapy has been pursued using mechanically strong thermally responsive hydrogels to inhibit pathological ventricular dilatation after myocardial infarction, a major contributor to morbidity and mortality in ischemic cardiomyopathy. As with other biomaterial applications where temporary mechanical support is the objective, the degradation behavior of thermally responsive hydrogels becomes a critical design consideration.

In seeking to control the degradation rate for a thermally responsive hydrogel that would be used in soft tissue injection, several other design criteria must be considered. Basic requirements are acceptably low levels of cytotoxicity of the polymer and degradation products and adequate thermal response to allow needle-based injection and stiffening in situ. In the role of cell carrier, one would want to maintain encapsulated cell viability. When tuning the degradation rate, one would ideally not impair the thermal sensitivity of the system or substantially alter the mechanical properties in the fluid or hydrogel state. Polyesters, widely used as biodegradable polymers in general, have been utilized as a hydrophobic component in thermally responsive hydrogels to trigger dissolution and absorption of the hydrogels upon ester cleavage. Polyester materials degrade faster under low pH conditions due to catalyzed hydrolysis. The accumulation of acidic degradation products can lead to an autocatalytic effect, accelerating the hydrolysis of ester bonds. It was anticipated that the autocatalysis effect could be employed to tune degradation rates across wide ranges. Thus, in this study the amount of acid in a thermally responsive copolymer backbone was varied to modulate the degradation rate of a poly(N-isopropylacrylamide) based hydrogel, poly(NI-PAAm-co-HEMA-co-MAPLA) (pNHM, copolymerized with N-isopropylacrylamide (NIPAAm), 2-hydroxyethyl methacrylate (HEMA) and methacrylate-polylactide (MA-PLA)). The pendant hydrophobic MAPLA sidechains become acidic units upon hydrolysis, resulting in a higher transition temperature and eventual solubility of the copolymer, without backbone cleavage. Different molar ratios of methacrylic acid (MAA) were incorporated into the copolymer to obtain poly(NIPAAm-co-HEMA-co-MAPLA-co-MAA) (pNHMMj). The effect of MAA on hydrogel degradation was studied as well as its effect on thermal and mechanical behavior. The cytotoxicity of pNHMMj hydrogels and their degradation products were evaluated and an in vivo degradation study of pNHMMj hydrogels was performed in a rat hindlimb injection model.

Materials and Methods

All chemicals were purchased from Sigma-Aldrich unless otherwise stated. N-isopropylacrylamide (NIPAAm) was purified by recrystallization from hexane and vacuum-dried. 2-Hydroxyethyl methacrylate (HEMA) was purified by vacuum distillation. Lactide, benzoyl peroxide (BPO), sodium methoxide (NaOCH$_3$), methacryloyl chloride, methacrylic acid (MAA) and other solvents were used as received.

The synthesis of methacrylate polylactide was performed as previously described (Ma et al. Thermally responsive injectable hydrogel incorporating methacrylate-polylactide for hydrolytic lability. Biomacromolecules 2010; 11: 1873-81). Briefly, NaOCH$_3$/methanol was added to a lactide/dichloromethane solution to synthesize polylactide (HO-PLA-OCH$_3$) through ring-opening polymerization. MAPLA was synthesized by dropping methacryloyl chloride into a HO-PLAOCH3/dichloromethane solution containing triethylamine. Dichloromethane was removed by rotary evaporation and the product was purified by flash chromatography to obtain MAPLA with yields of ~60%.

Figure 4:
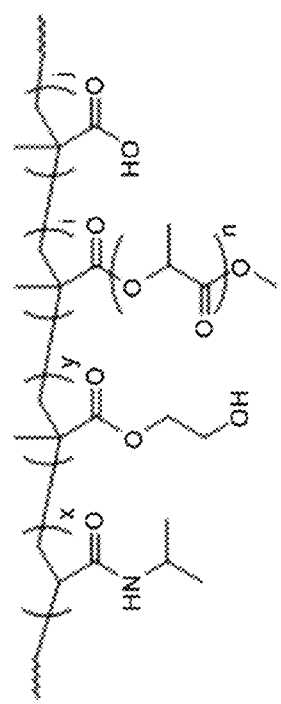
FIG. 4. Synthesis of poly(NIPAAm-co-HEMA-co-MAPLA-co-MAA) (pNHMMj)
Figure 4:
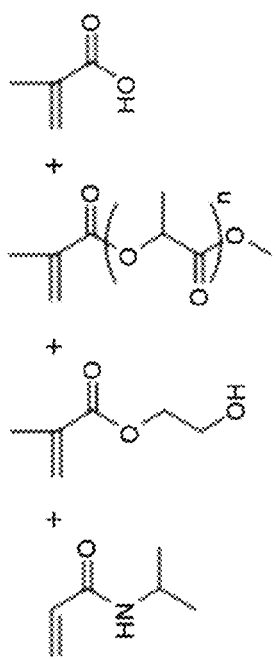
Figure 5:
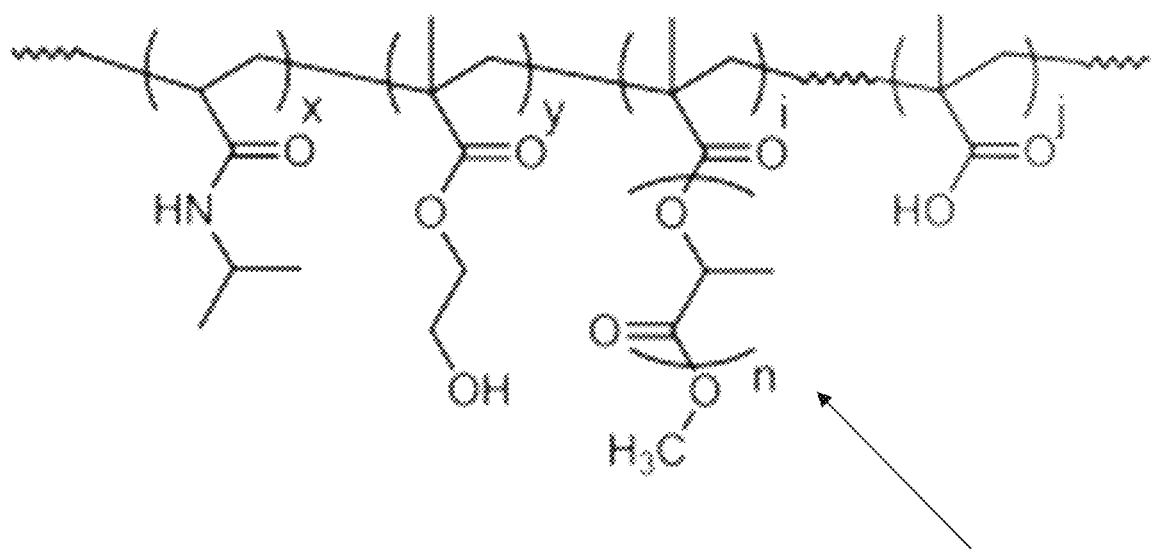
FIG. 5. Chemical structure of poly(NIPAAm-co-HEMA-co-MAPLA-co-MAA) (pNHMMj). The arrow shows the position of a hydrophobic to hydrophilic alteration upon side-chain hydrolysis.

Poly(NIPAAm-co-HEMA-co-MAPLA-co-MAA) (pNHMMj) copolymers (FIGS. 4 and 5) were synthesized from NIPAAm, HEMA, MAPLA and MAA by free radical polymerization. The feed ratios of NIPAAm, HEMA, MAPLA and MAA were 80/(10-j)/10/j, where j=0, 0.5, 1, 2, 5, 10 (FIG. 4). Table 2, showing the parameters for production illustrated in FIG. 4, is shown below.

TABLE 2

Feed ratio for various poly(NIPAAm-co-HEMA-co-MAPLA-co-MAA) (pNHMMj) copolymers

| MAA feed ratio (%) | Feed ratio (%) | | | |
|---|---|---|---|---|
| | NIPAAm | HEMA | MAPLA | MAA |
| 0 | 80 | 10 | 10 | 0 |
| 0.5 | 80 | 9.5 | 10 | 0.5 |
| 1 | 80 | 9 | 10 | 1 |
| 2 | 80 | 8 | 10 | 2 |
| 5 | 80 | 5 | 10 | 5 |
| 10 | 80 | 0 | 10 | 10 |

Monomers (0.066 mol) were dissolved in 180 mL of 1,4-dioxane containing 0.23 g BPO. The polymerization was carried out at 75° C. for 20 h under argon protection. The copolymer was precipitated in hexane and further purified by precipitation from THF into diethyl ether and vacuum-dried, with yields of ~80%. Fluorescently labeled copolymers were synthesized using the same reaction conditions with fluorescein 0-methacrylate added at a feed ratio of an additional 2%, with all of the other monomer molar ratios remaining constant and j=0. Fluorescently labeled hydrogels used in the in vivo study were prepared by dissolving 14.25 wt % unlabeled copolymer with 0.75 wt % labeled copolymer in PBS.

$^1$H NMR spectra of pNHMMj were recorded with a 600 MHz Bruker spectrometer using CD3Cl or DMSO-d6 as a solvent. Molecular weight of the copolymers was determined by gel permeation chromatography (GPC, Waters Breeze System, Waters 1515 HPLC Pump, Waters 2414 differential refractometer). The copolymers were dissolved in THF at a concentration of 1 mg/mL and the GPC analysis was performed at 35° C. A poly(methyl methacrylate) standard kit (Fluka, ReadyCal Set Mp 500-2700000) was used for molecular weight-elution volume calibration.

Rheology studies were conducted on a TA Instruments rheometer (AR2000) to observe viscosity changes in the hydrogels during the temperature induced solegel transition. The polymer solutions (15 wt % in PBS) were placed between two parallel plates. With a temperature sweep from 5 to 35° C. and a heating rate of 5° C./min, the shear storage modulus G0 and the loss modulus G00 were collected as a function of temperature at a fixed strain of 2% and a frequency of 1 Hz.

To measure the mechanical properties of the hydrogels, samples were incubated in a 37° C. water bath for 24 h to reach a stable water content, and then the solid hydrogels were cut into rectangular strips 1 mm thick, 4 mm wide, and 25 mm long and then loaded in a water bath equilibrated to 37° C. An ElectroForce 3200 Series II (Bose, Minn., US) equipped with a 2.5 N load cell was utilized to record the tensile stress-strain curve immediately after the samples were taken out of the water bath.

Hydrogel degradation was quantified by mass loss measurements. Hydrogels with known initial dry masses (~60 mg) were immersed into 6 mL of PBS at 37° C. At predefined time points over a 28 week period the hydrogels (n=3 each) were lyophilized and the relative mass loss was recorded. The pH of the supernatant during degradation was measured with an Accumet pH meter (Fisher Scientific, Waltham, Mass.). To compare the relative pH inside pNHMMj hydrogels, polymers were dissolved in PBS containing 2.5 mM LysoSensor Yellow/Blue DND-160 pH sensitive dye (Life Technologies, Grand Island, N.Y., US). After gelation, the excess fluid was removed and replaced with PBS. The hydrogels were allowed to stabilize for 1 d before being placed in a plate reader with excitation at 360 nm and emission intensities at 440 nm and 540 nm measured for the hydrogel surface and cross sections (cut and exposed). The cross sections were used to semi-quantitatively determine whether there was detectably lower pH in the hydrogel interior.

The cytotoxicity of the pNHMMj degradation products was assessed by measuring the relative metabolic activity of rat vascular smooth muscle cells (rSMCs) cultured in Dulbecco's modified Eagle medium (DMEM) (Gibco, Life technologies) with 10% fetal bovine serum (FBS), 1% penicillin/streptomycin, and supplemented at 10% with hydrogel degradation solution. The hydrogel degradation solution was prepared from incubation of the hydrogel in PBS. Culture medium with PBS added at 10% was used as a negative control rSMCs were seeded at an initial density of 30,000/cm2 and their metabolic activity was measured (n=each) using an MTS assay kit (Promega CellTiter 96 Cell Proliferation Assay). To qualitatively verify the results of the above test, cells were also observed under fluorescence microscopy after live/dead staining with a Promokine Live/Dead Cell Staining Kit.

rSMCs labeled with the live cell marker CellTracker Red CMTPX (Life Technologies, Grand Island, N.Y.) were suspended in PBS at a density of 2×107/mL. A total of 0.25 mL of this cell suspension was then added into 1 mL of the hydrogel solutions at 4° C. The mixture was thoroughly mixed before being transferred into a 37° C. water bath for gelation. The supernatant was removed and replaced with culture medium (DMEM supplemented with 10% FBS, and 1% penicillin/streptomycin). The medium was changed every 3 d. After 1 and 7 d of culture, samples were taken out and cut into 100 mm thick sections and observed directly under fluorescence microscopy (Eclipse Ti-U, Nikon Instruments). At 7 d another set of samples were cooled at 4° C. to release the encapsulated cells and these released rSMCs were then cultured on TCPS for an additional 7 d to qualitatively assess their ability to proliferate. In a separate set of experiments, unstained rSMCs were encapsulated as described above and upon recovery from the hydrogels by cooling at 1 and 4 d were stained with trypan blue solution and the percentages of live cells were calculated by manual counting of multiple microscopic fields for 3 independent samples for each hydrogel type.

Adult female Lewis rats weighing 160-210 g were utilized in a protocol that followed the National Institutes of Health guidelines for animal care and that was approved by the University of Pittsburgh's Institutional Animal Care and Use Committee. Anesthesia was induced with 3.0% isoflurane inhalation with 100% oxygen followed by 1.5e2% isoflurane with 100% oxygen during procedure. Dermatotomy was performed to expose the inner thigh muscles on both legs. Single injections of 200-250 mL of hydrogel (fluorescently labeled or unlabeled) were made approximately 3 mm deep in the muscle bed. For each hydrogel, 6 injections in 6 legs were made (4 labeled, 2 unlabeled). Inner thigh muscles from 2 legs of the labeled groups were excised 3 min after injection. The muscles were incised to expose the hydrogels, and images were taken with a Dino-Lite (AM4113T-GFBW, AnMo Electronics, New Taipei City, Taiwan) under bright field and fluorescence mode. After 21 d, rats were sacrificed and the inner thigh muscles encompassing the hydrogels were excised, images taken and the tissue was fixed in 10% formaldehyde for 3 d before embedding. H&E staining (for unlabeled hydrogels) and immunohistochemical staining (with labeled hydrogels) with monoclonal antibodies against CD68 (1:100, Abcam) was performed. Nuclei were stained with 400,6-diamidino-2-phenylindole (DAPI; 1:10000, Sigma). Microscopic images were taken under fluorescence microscopy and assessed with ImageJ.

Figure 7:
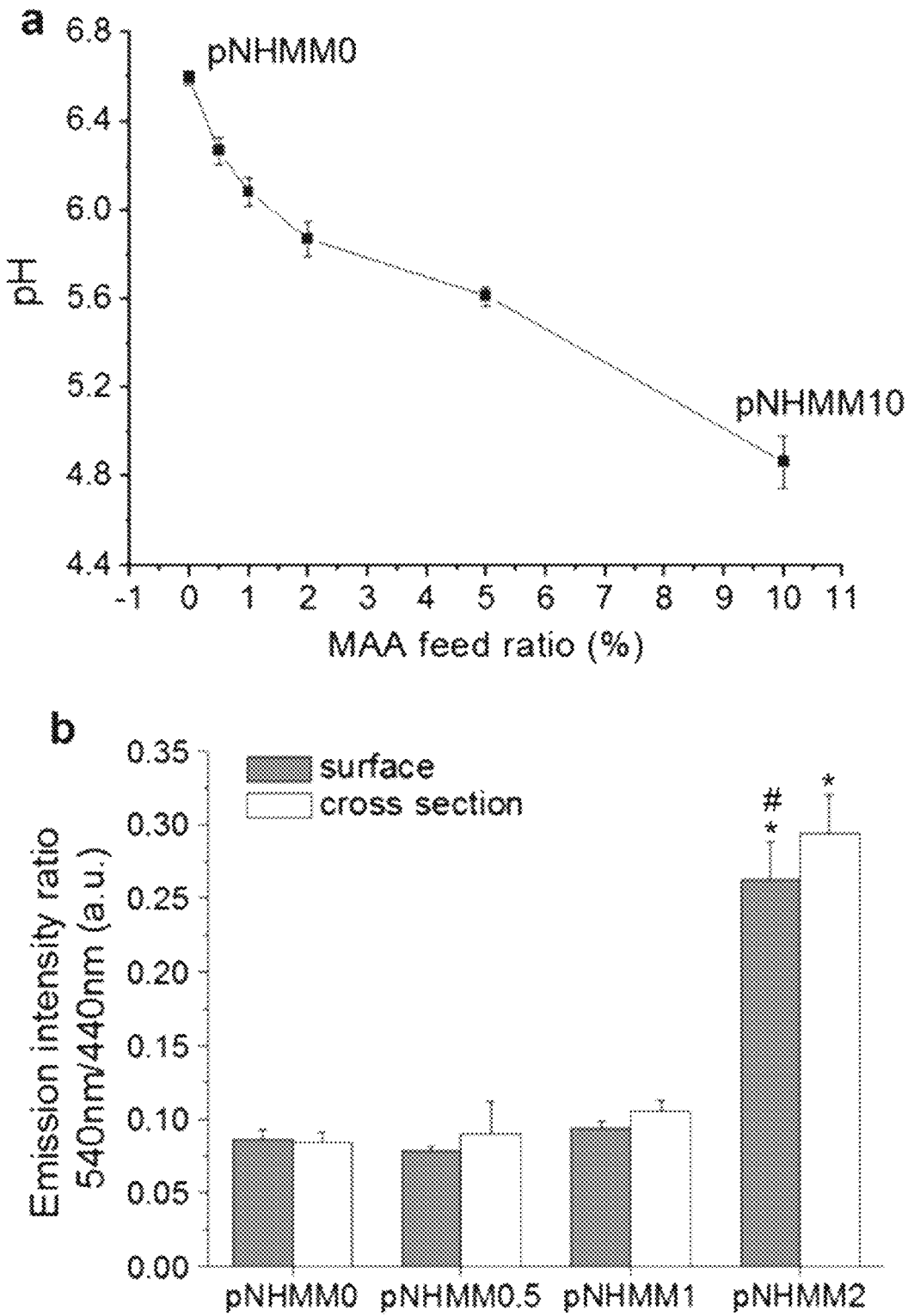
FIG. 7. pH of supernatants of pNHMMj hydrogels after gelation (a); Fluorescent emission intensity ratio between 540 nm and 440 nm of pNHMMj hydrogels mixed with LysoSensor pH-sensitive dye, excited at 360 nm (b). A higher ratio reflects a lower pH. Data of pNHMM5 and pNHMM10 were not available due to fast degradation. * and # indicate significant differences between and within groups, respectively.

For the paired comparisons of FIG. 7, a paired t-test was employed. Where three or more groups were being compared, one-way ANOVA was employed with Tukey's test applied for specific comparisons. Results are presented as the mean with standard deviation. Statistical significance was defined as $p<0.05$.

Results

Figure 6A:
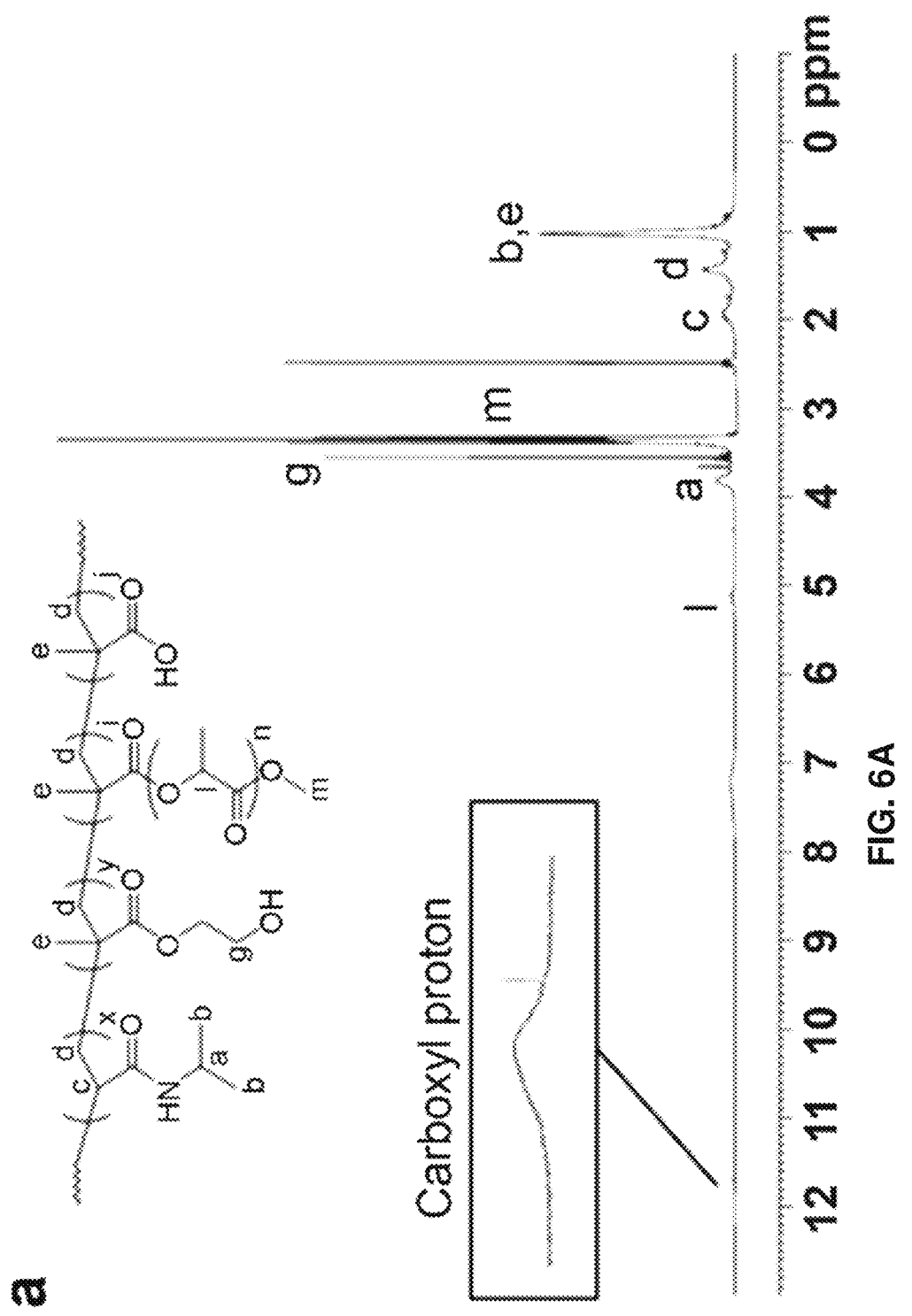
FIG. 6A-6B. NMR spectra of poly(NIPAAm-co-HEMA-co-MAPLA-co-MAA) (pNHMMj) showing the MAA peak (12 ppm) present in the composition according to the present invention (FIG. 6A); MAA weight percentages in copolymers as determined by NMR and acid titration at feed ratios of 0.5%, 1%, 2%, 5%, and 10% (FIG. 6B).
Figure 6B:
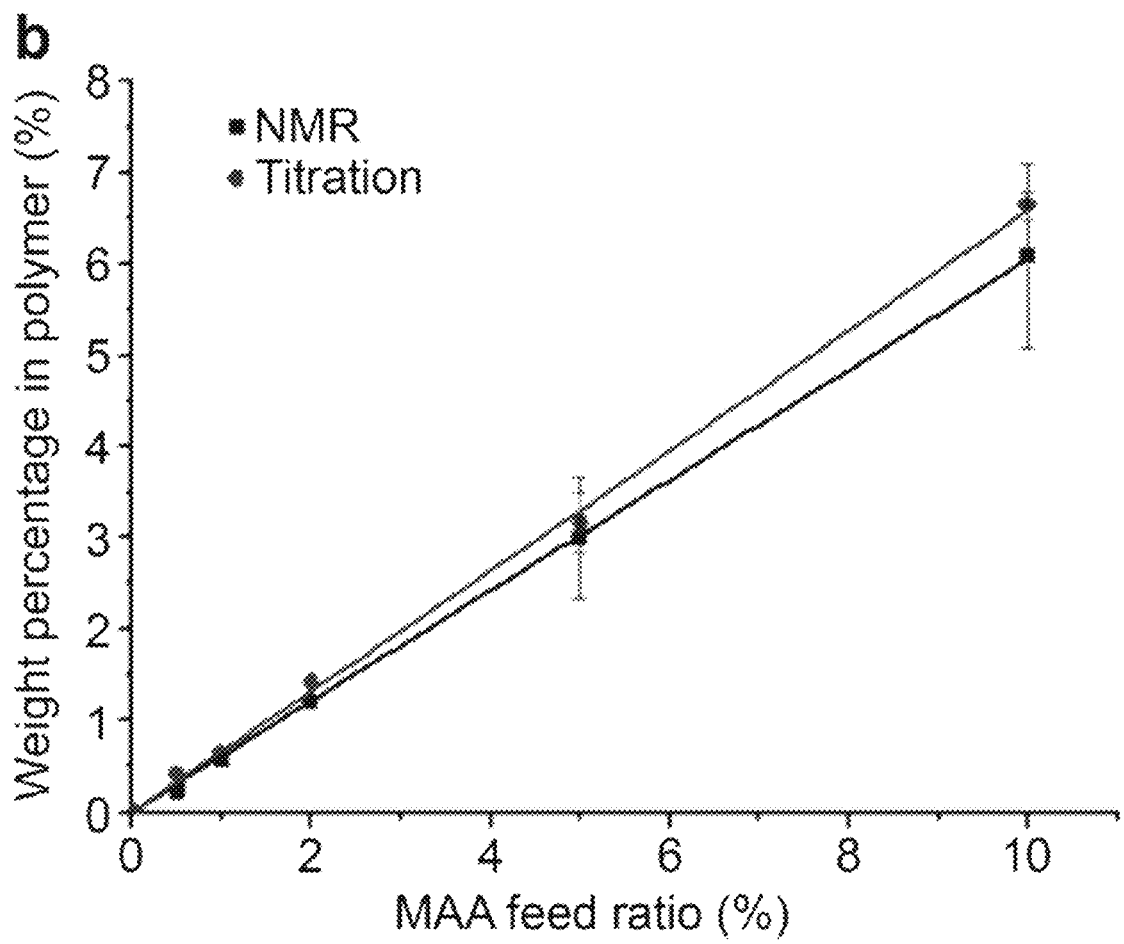

The incorporation of MAA into the hydrogels was confirmed by NMR as the eCOOH peak appeared at ~12 ppm on the $^1$H spectrum, as shown in FIG. 6A. The content of MAA in the copolymer calculated with peak areas shows a linear increase with the MAA feed ratio, (FIG. 6B) although this content is ~40% lower than the MAA feed ratio in the reaction system. This result was also confirmed with minor discrepancies from the NMR results by titrating the eCOOH groups in the copolymer with HCl/NaOH for protonation/deprotonation (FIG. 6B). GPC results showed that the molecular weights Mw of the pNHMMj copolymers were all between 22000 and 26000 g/mol.

Figure 8:
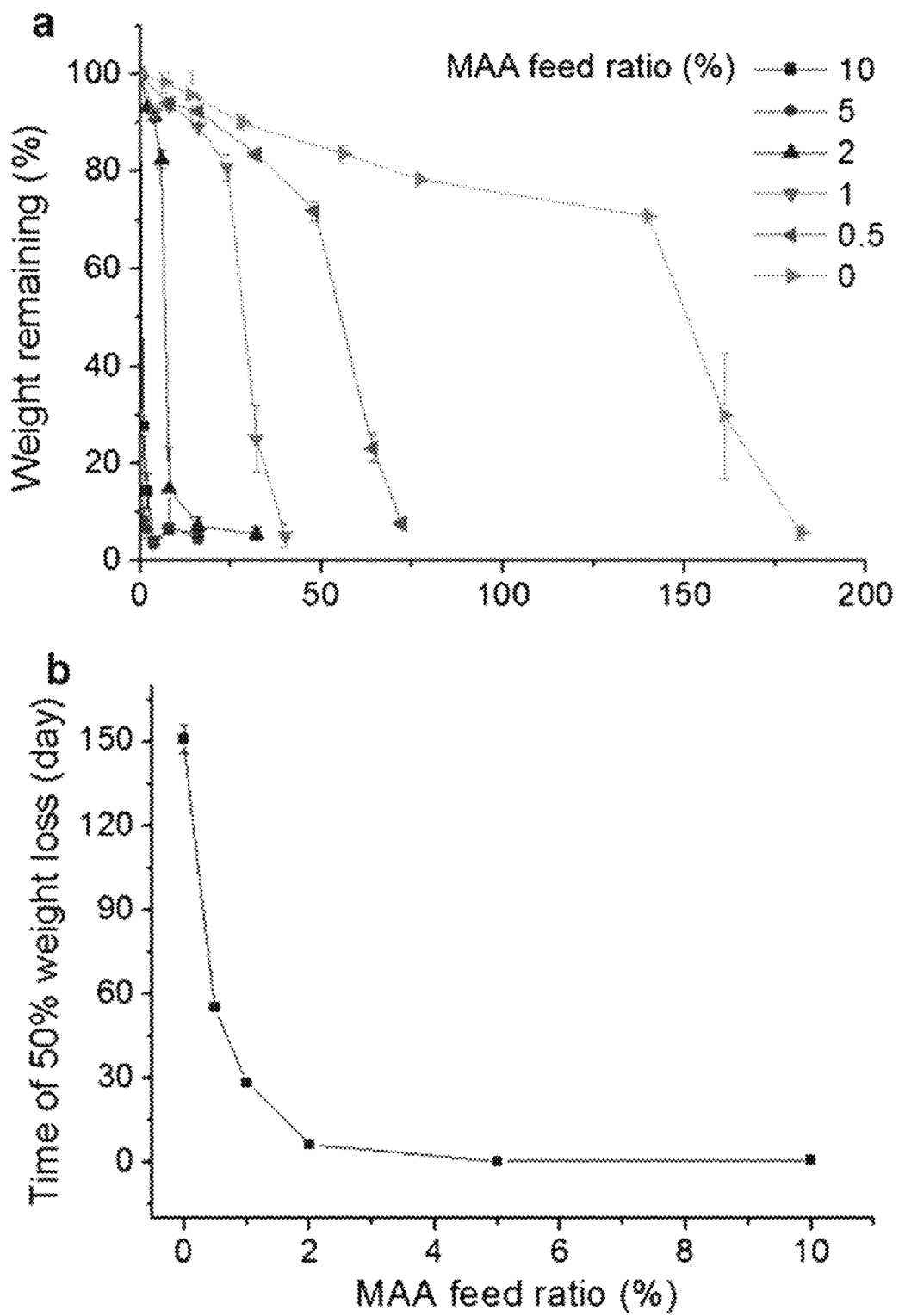
FIG. 8. Degradation curves of poly(NIPAAm-co-HEMA-co-MAPLA-co-MAA) (pNHMMj) hydrogels with graded MAA content (a); Time for 50% weight loss derived from data in the previous panel (b).
Figure 25:
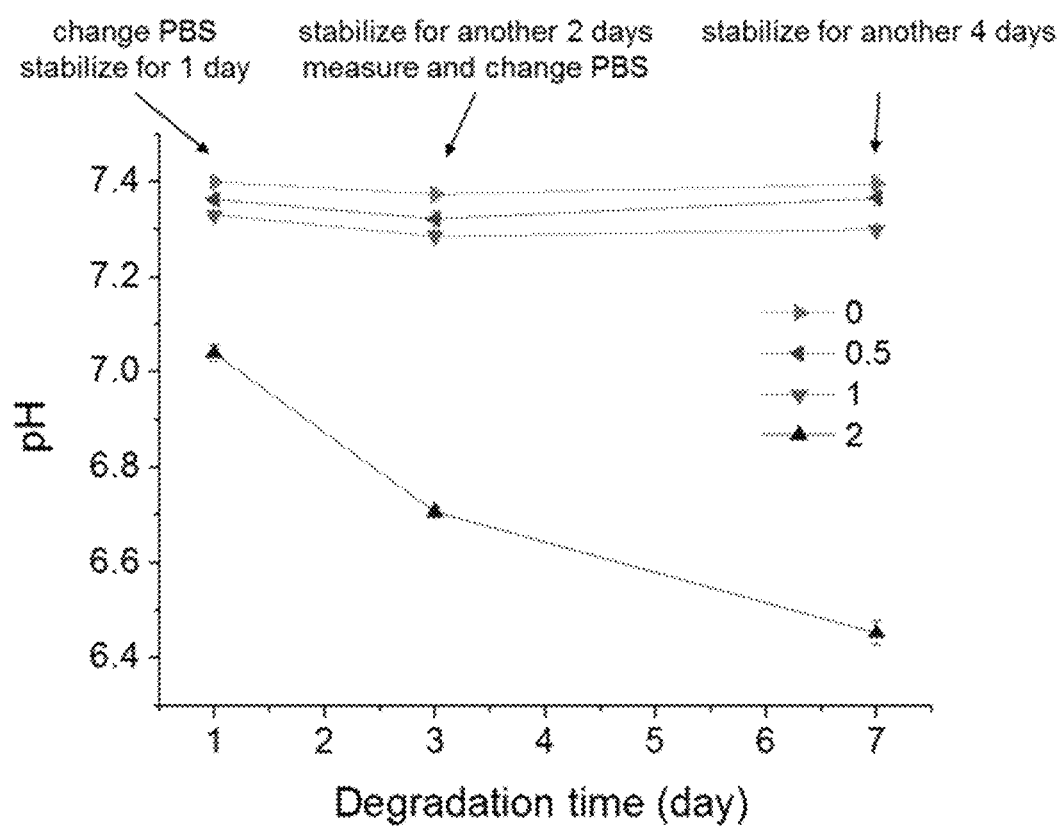
FIG. 25. Change of supernatant pH during degradation of pNHMMj hydrogels in PBS.
Figure 26:
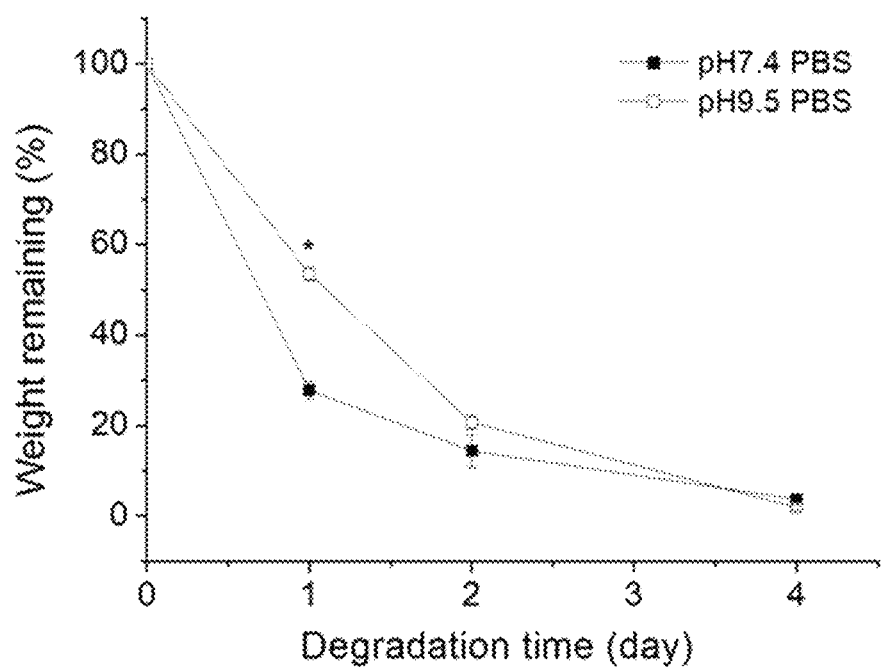
FIG. 26. Weight loss of pNHMM10 incubated in regular PBS (pH 7.4) and basic PBS (pH 9.5, mediated by NaOH).

The pH of the supernatant solution after gelation of the pNHMMj polymers in PBS buffer (15 wt % of copolymers) showed that with increased MAA content in the copolymer, the more acidic the initial degradation environment was for PLA sidechains in this limited volume system, FIG. 7. Measured immediately after changing PBS, the supernatant pH for all pNHMMj increased, and showed no significant difference compared to the pH of PBS. After stabilization for 24 h to allow diffusion, the supernatant pH of pNHMM0, pNHMM0.5 and pNHMM1 remained above 7.3, whereas the pH for pNHMM2 dropped below 7.1 (FIG. 25, pNHMM5 and pNHM10 degraded too quickly for this measurement). After another cycle of PBS change and measurement after another 4 d, the pNHMM2 continued to be able to reduce the pH versus the other hydrogels. On the other hand, after gelation and placement in fresh PBS, followed by 24 h stabilization, the pH was lower in and on the surface of pNHMM2 hydrogel compared to pNHMM0, pNHMM0.5 and pNHMM1, as indicated by a pH-sensitive dye (LysoSensor, whose emission intensity ratio between 540 nm and 440 nm increases as pH decreases). In addition, the pH of the interior of the pNHMM2 hydrogel was lower than the pH on the surface. No significant differences were found among the other 3 polymer types (data not available for pNHMM5 and pNHMM10 due to rapid degradation). The degradation rate increased significantly as MAA was added in increasing proportion into the polymer backbone, as shown by the weight loss profile of the hydrogels in PBS, FIG. 8, top panel. Without MAA, pNHMM0 needed over 5 mo to lose 50% weight in PBS, and the same loss required about 2 mo, 1 mo, 1 wk and 1 d for MAA containing copolymers with the MAA feed ratio at 0.5% (pNHMM0.5), 1% (pNHMM1), 2% (pNHMM2), 5% (pNHMM5) and 10% (pNHMM10), as shown in FIG. 3*b*. The temporal weight loss profiles of the pNHMMj hydrogels share a similar shape, which begins with a slow weight loss stage, followed by an abrupt decrease in remaining weight. Furthermore, when incubated in PBS solution at pH 9.5, the abrupt weight loss for MAA10 was postponed for 1 d (FIG. 26). Since pNHMM5 and pNHMM10 hydrogels were considered to degrade too quickly for potential in vivo applications, hydrogels with less MAA were selected as candidates for further evaluation.

Figure 9:
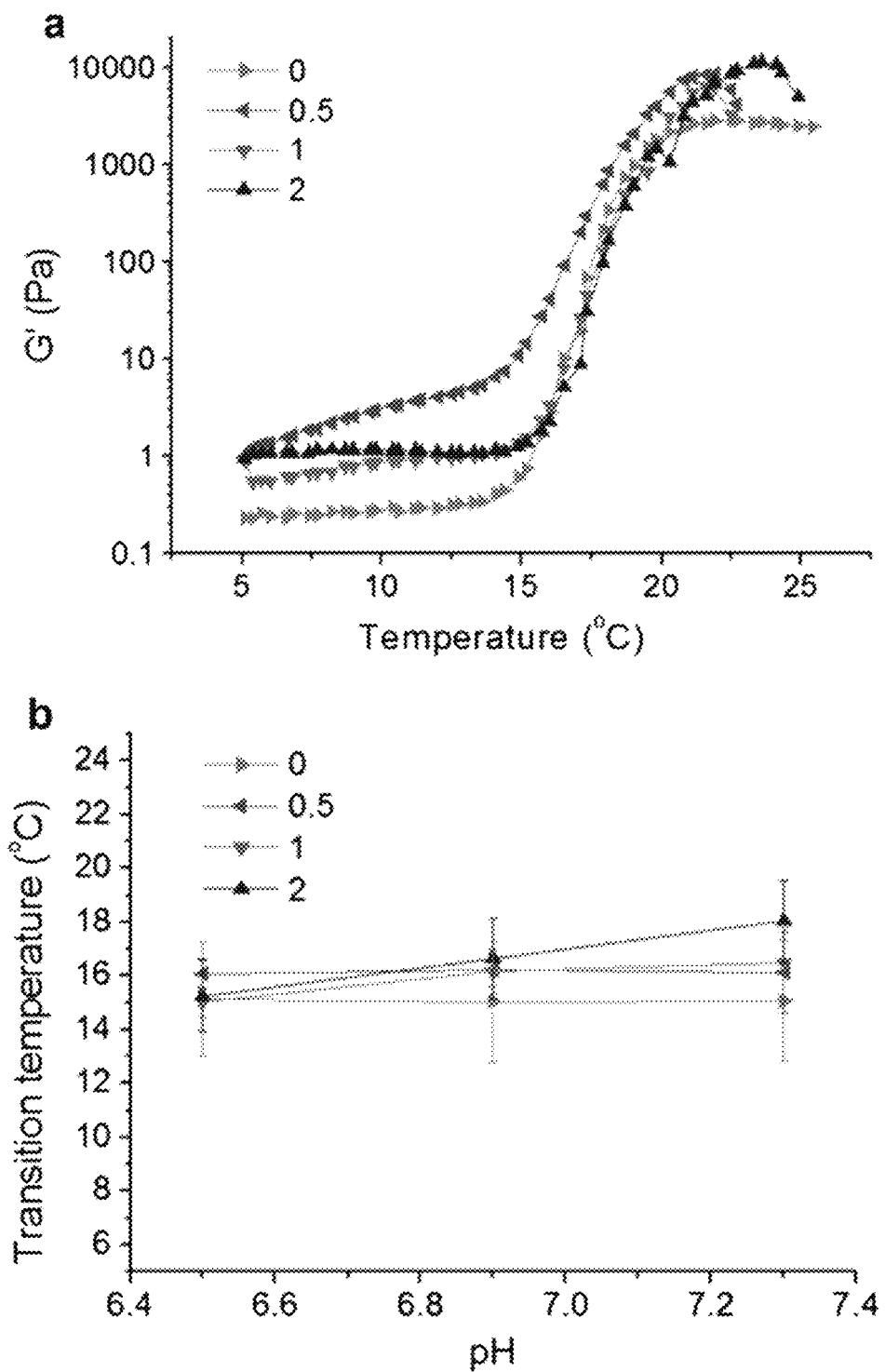
FIG. 9. Transition temperature of pNHMMj hydrogels. Temperature sweep of shear modulus (G') of pNHMMj hydrogels (a); Transition temperature dependence on pH (b).
Figure 10:
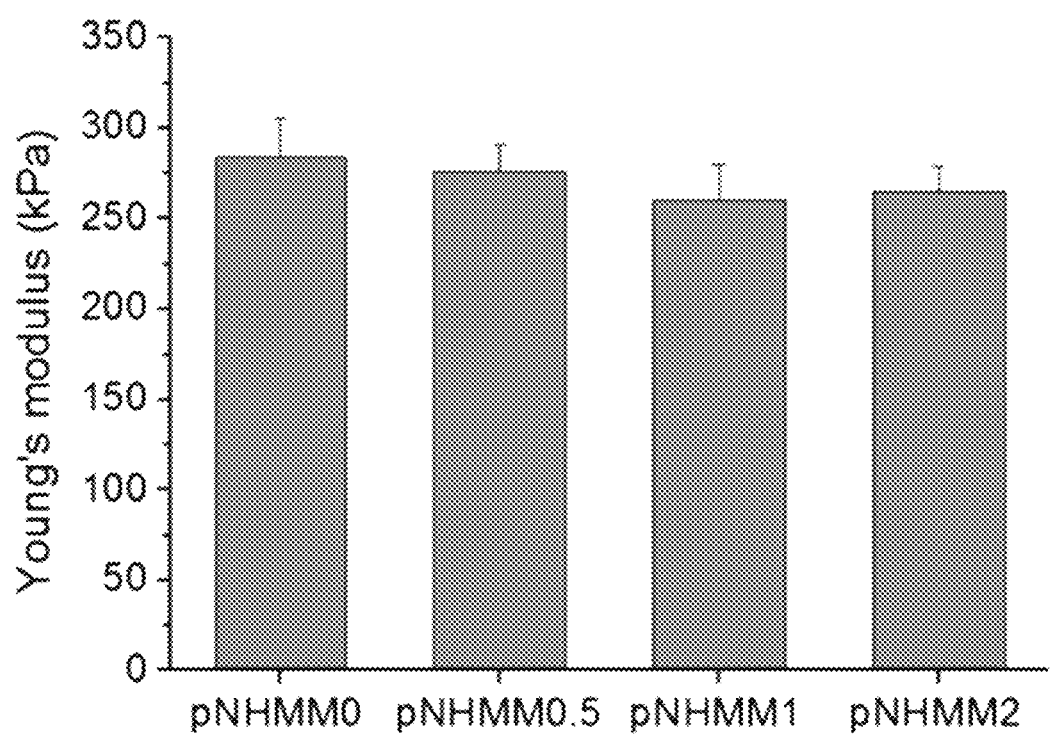
FIG. 10. Mechanical properties (Young's modulus) for hydrogels formed from copolymer compositions according to embodiments of the present invention.

The transition temperature of MAA hydrogels in PBS did not shift significantly as the MAA content in the polymer backbone was increased. As shown in FIG. 9, top panel, the rapid increase in shear modulus G0 of pNHMM0, pNHMM0.5, pNHMM1 and pNHMM2 occurred within 17.5±2.5° C., which represents the sol-gel transition as temperature rises. Accompanying this mechanical transition the copolymers were observed to become optically opaque and form white gels. The abrupt increase in shear modulus or viscosity required only a few sec at 37° C., hence when pNHMMj hydrogels were injected into PBS at 37° C., the response was rapid. As shown in FIG. 9, bottom panel, solution pH did not significantly affect the transition temperature of pNHMMj hydrogels, especially in the weak acidic range. The Young's modulus of pNHMMj hydrogels were all above 200 kPa and did not vary significantly with increasing MAA content (FIG. 10), indicating that the degradation or absorption rate for the hydrogels was decoupled from their initial mechanical stiffness in tension when the MAA content was low.

Figure 11:
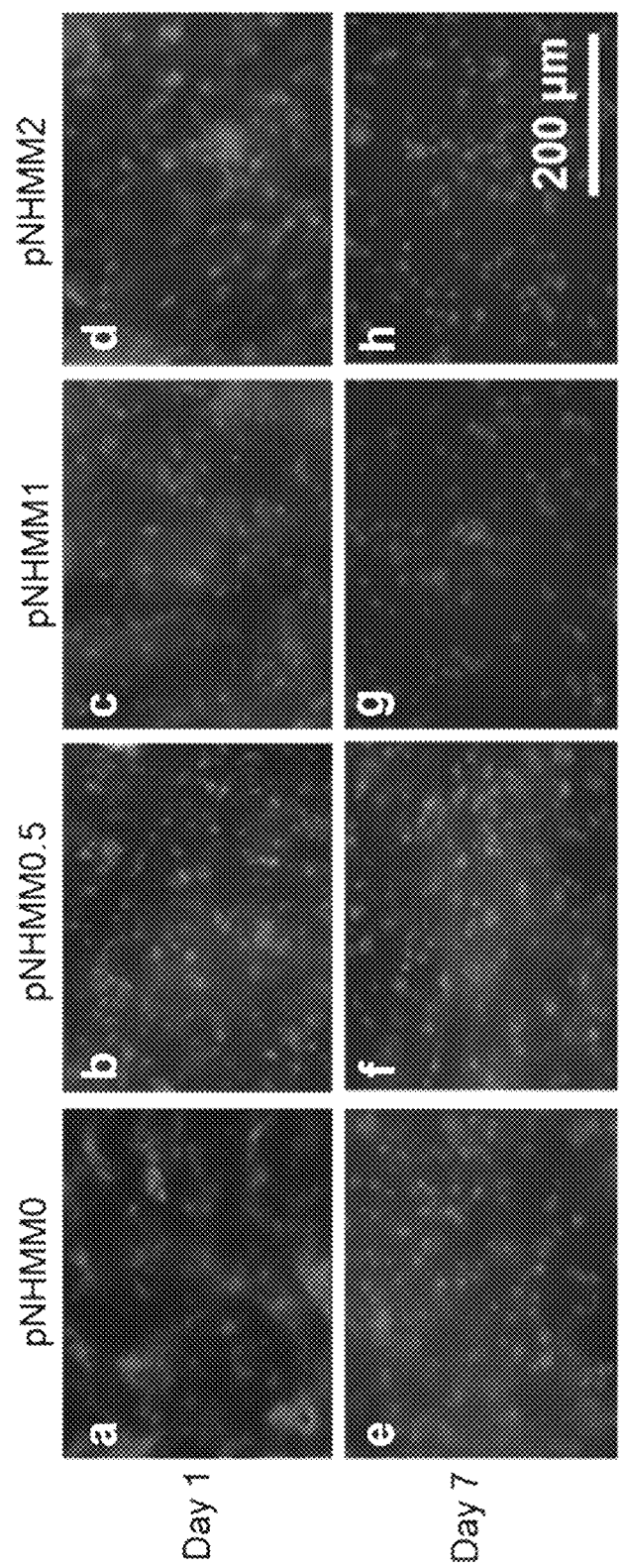
FIG. 11. Viability of rSMCs encapsulated in pNHMMj hydrogels. (a-h) Live rSMCs (red) stained with CellTracker in pNHMMj hydrogels 1 d and 7 d after encapsulation. Green: Fluorescein labeled hydrogels.
Figure 12:
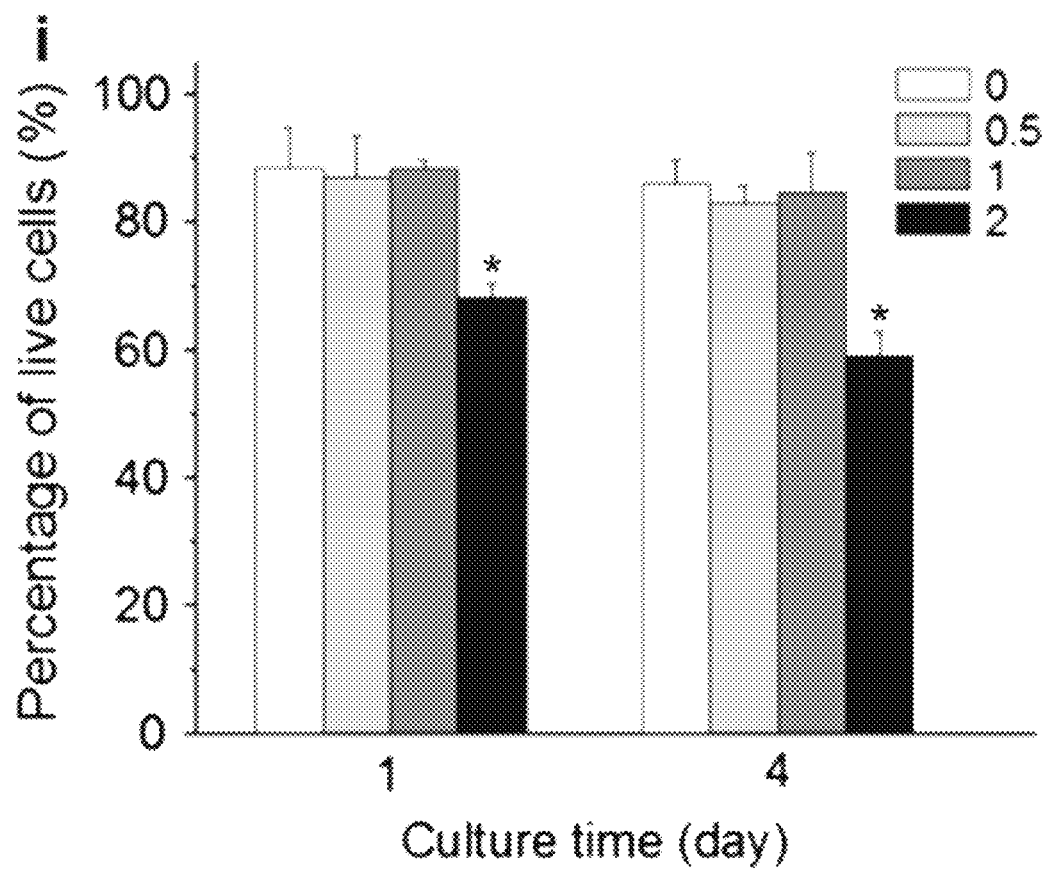
FIG. 12. Percentage of live rSMCs after 1 d and 4 d encapsulation in pNHMMj hydrogels, determined by trypan blue staining.
Figure 13A:
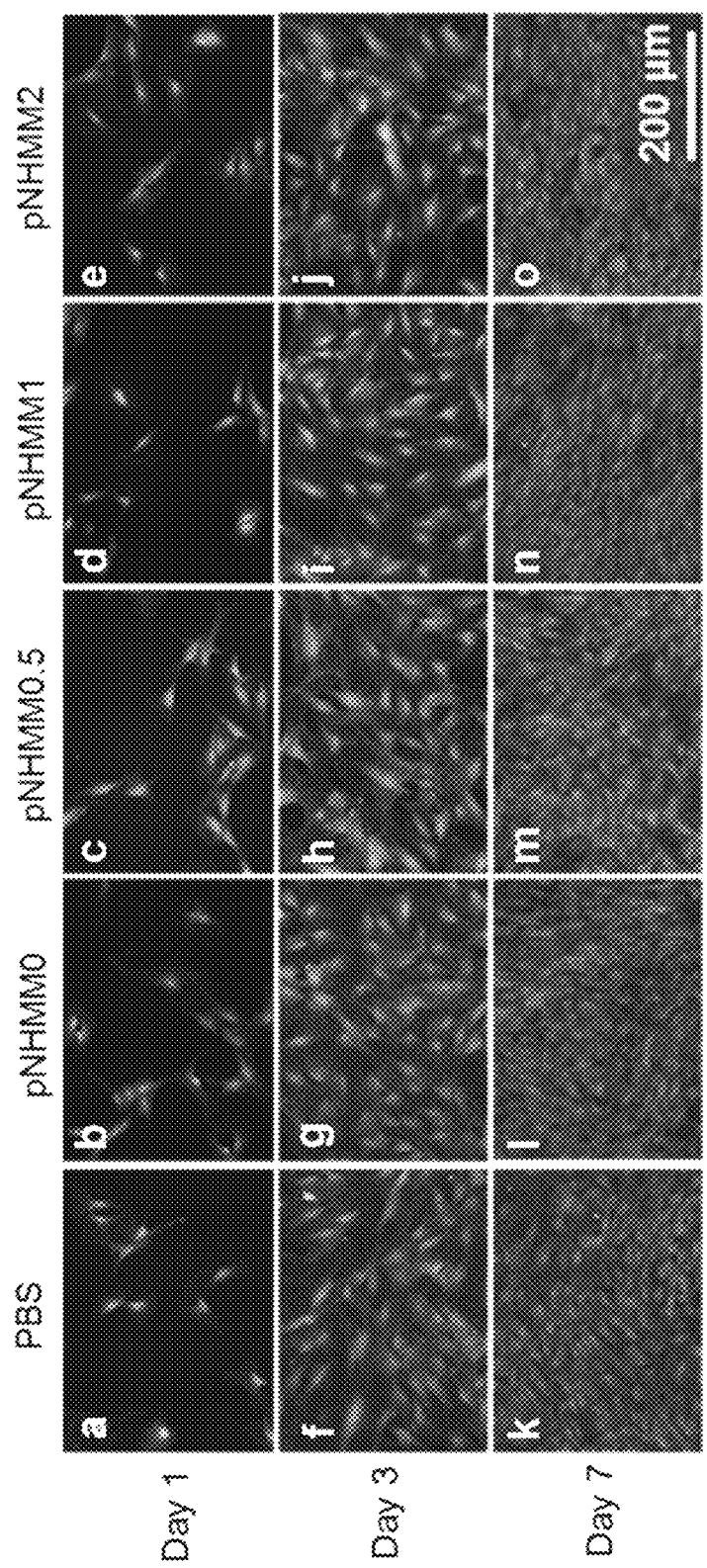
FIG. 13A-13B. Cytotoxicity of degradation products of pNHMMj hydrogels. rSMCs proliferation 1 d (a-e), 3 d (f-j), 7 d (k-o) after seeding determined by live/dead staining; (p) MTS assay of the rSMCs.
Figure 13B:
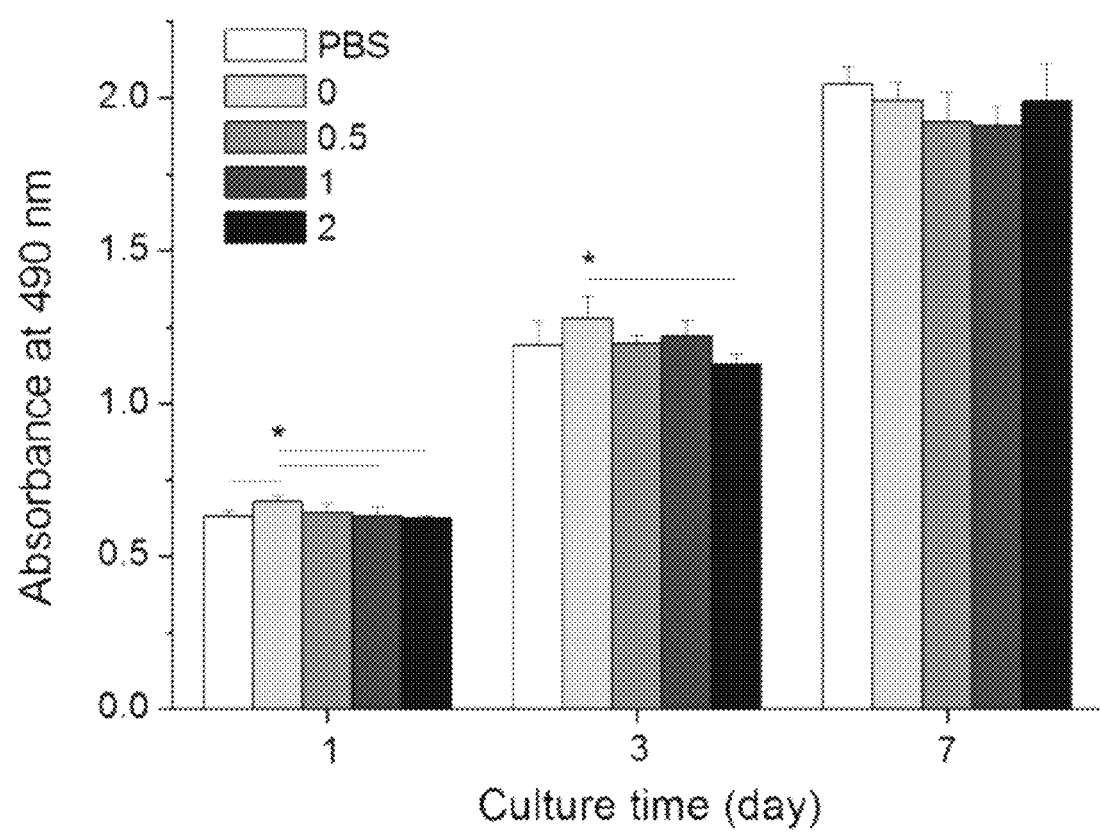
Figure 27:
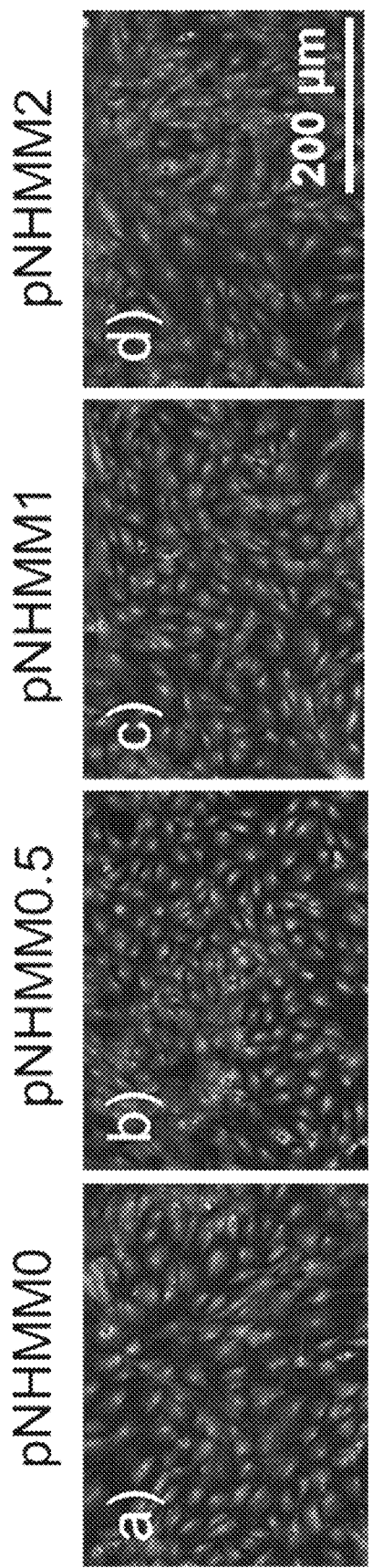
FIG. 27. SMCs cultured for another 7 d after retrieving from inside pNHMMj hydrogels and seeding on TCPS.

As shown in FIG. 12, panel round single cells were evenly distributed when rSMCs were encapsulated within the hydrogels. Using trypan blue to quantify viability, one day after encapsulation, over 85% cells were alive in pNHMM0, pNHMM0.5, pNHMM1 gels, while less than 70% cells survived inpNHMM2 (FIG. 12). Viability was ~85% in pNHMM0, pNHMM0.5, pNHMM1 gels 4 d after encapsulation, while viability was less than 60% in pNHMM2 (FIG. 11). Qualitatively assessing cells stained with a viability marker at the time of encapsulation showed that after 1 and 7 d culture, viable cells remained spread throughout the hydrogels (FIG. 11). Cells isolated at 7 d and cultured on TCPS for 7 d qualitatively showed an ability to proliferate (FIG. 27). The cytotoxicity of the degradation products of pNHMMj hydrogels were also tested. Live/dead staining showed that rSMC proliferation was not impeded by any of the copolymer degradation products: overall metabolic activity of the cultures during the 7 d increased, suggesting cell proliferation, and few dead cells were observed after recovery and culture on TCPS (FIG. 13A). Slightly different from the findings from the encapsulation experiment, degradation products of the pNHMM2 hydrogel did not show higher cytotoxicity compared to its counterpart pNHMMj hydrogels (FIG. 13B).

Figure 14:
FIG. 14. Rat heart injected with MAPLA gel labeled with a small amount of fluorescent monomer (A and B).
Figure 14:
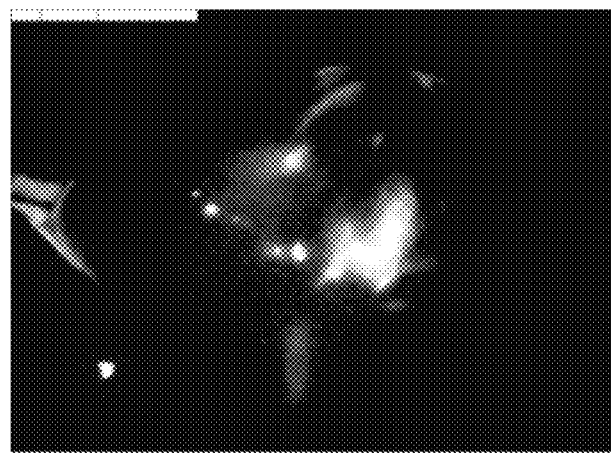

In addition, smooth muscle cell proliferation was not significantly affected by the hydrogel degradation products. FIG. 14 shows the gross appearance of a rat heart injected with MAPLA Gel, which was similar to those injected with hydrogels with different MAA content.

Figure 15:
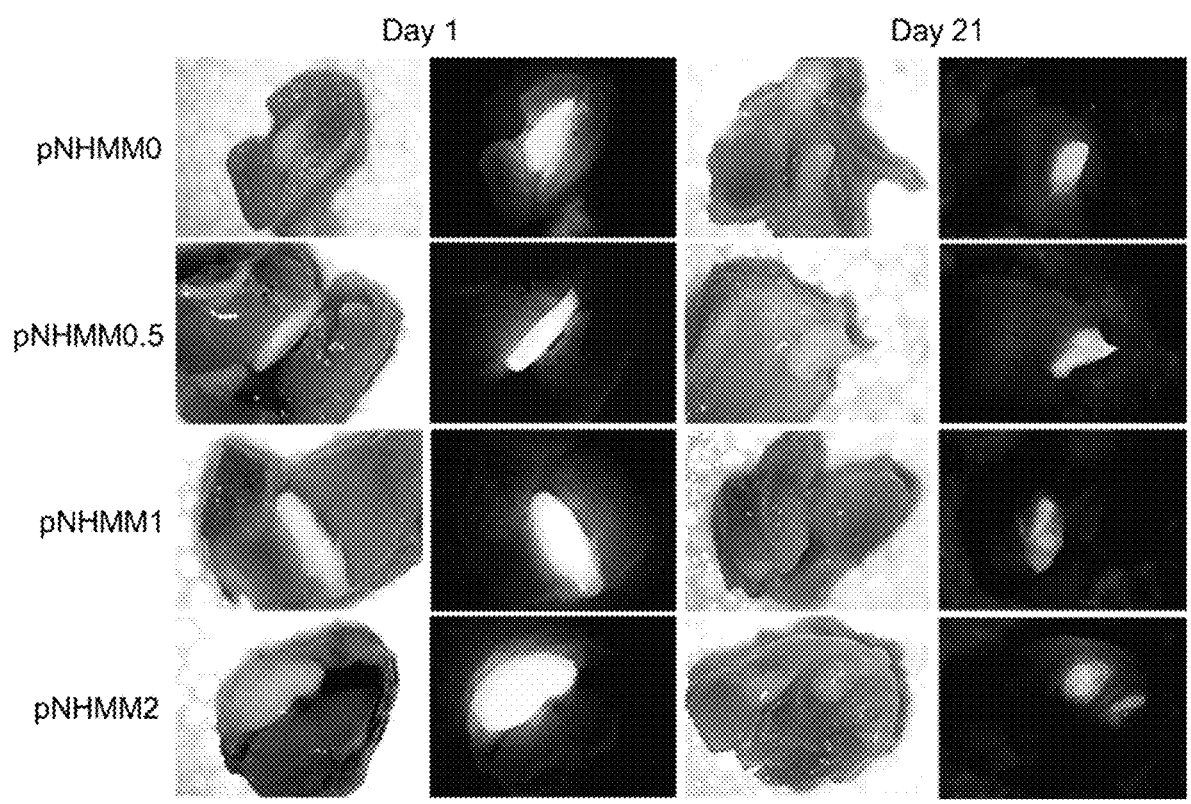
FIG. 15. Bright field and fluorescent images of excised rat leg muscles injected with pNHMMj hydrogels. Left column: excised on the same day of injection. Right column: excised 21 d after injection. The white mass and green fluorescence indicate the hydrogel.
Figure 16:
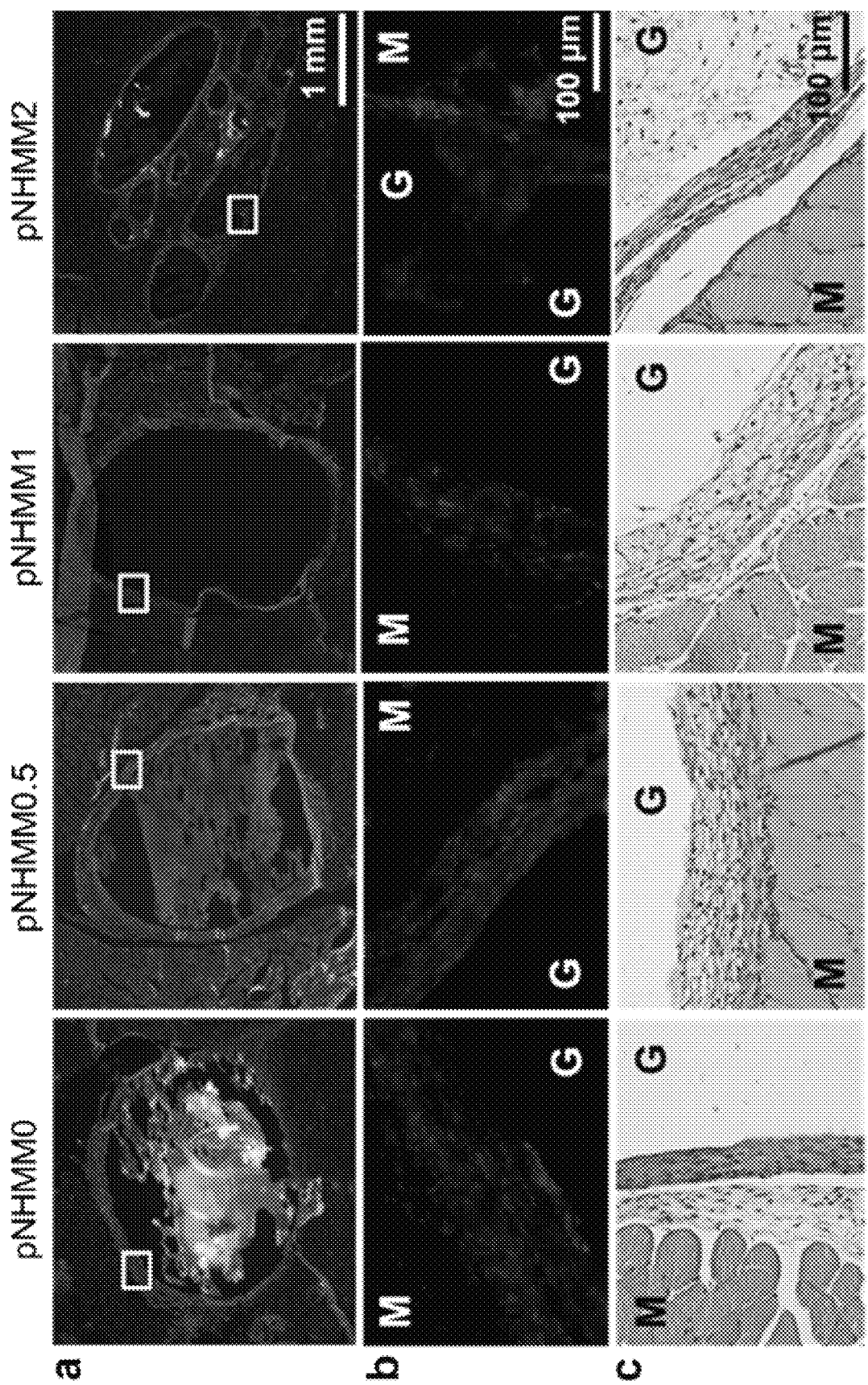
FIG. 16. Immunohistochemical (row (a,b)) and H&E (row (c)) staining of rat hindlimb muscle injected with pNHMMj hydrogels 21 d after injection. In row (a) and row (b): Blue: DAPI for nucleus, Green: hydrogels, Red: CD68 for macrophages. Images in row (b) are enlarged from corresponding areas in row (a), as indicated by yellow rectangles (may be rotated). M indicates muscle and G indicates hydrogel.

In vivo degradation and absorption of hydrogels was tested in rat hindlimb muscles. Hydrogels solidified immediately upon being injected into the muscles and formed distinct volumes, displacing the muscle tissue, as shown in the left columns of FIG. 15. Fluorescent imaging revealed that the hydrogels formed well-defined regions, with minimal diffusion into the tissue. This effect was also demonstrated on immunohistochemical staining sections obtained from tissue immediately after injection (data not shown). After 21 d, the boundaries between injected hydrogels and the leg muscles were more diffuse compared to the time right after injection, particularly for pNHMM1 and pNHMM2, as shown in the right columns of FIG. 15. Fluorescent signals could still be observed, showing that the hydrogels were not completely absorbed. However, the fluorescence intensities were weaker in all four groups compared to the initial status. Unabsorbed hydrogels could be identified in immunohistochemical sections in all four groups as irregularly shaped regions encompassed by dense cell populations (FIG. 16, panel a). For most of the polymers these regions of injection had minimal or no fluorescence, while for the pNHMM0 group this region was seen to have higher green fluorescence in large, continuous areas. The dense cell populations surrounding the polymers were CD68 positive and identified as macrophages (FIG. 16, panels a and b). For pNHMM0, pNHMM0.5 and pNHMM1 hydrogels, macrophages encompassed the materials, however, did not appear to infiltrate into the polymer. For the pNHMM2 group, macrophages infiltrated into the injection site, separating the remaining hydrogel volumes. Similar observation could be made on H&E stained sections. Macrophages gathered and formed capsules around injected hydrogels as shown in FIG. 16, panel c. Macrophages can be found in some regions of unabsorbed pNHMM2 hydrogel, migrating from the border zone. This was not observed with the other 3 polymer types.

Discussion

Different strategies have been reported to modulate the degradation of thermally responsive hydrogels. For poly (ethylene glycol)-poly(ε-caprolactone)-poly(ethylene glycol) (PEG-PCL-PEG), poly(ethylene glycol)-poly(lactide-co-glycolide)-poly(ethylene glycol) (PEG-PLGA-PEG) and similar block copolymer systems, changing the molecular weight of individual blocks and the molecular weight ratio between hydrophobic and hydrophilic blocks results in changes in degradation rate. For thermally responsive systems that employ crosslinking, adjusting the crosslinking density is effective. In poly(N-isopropylacrylamide) based hydrogels, the content of hydrolytic pendant groups has been shown to have a significant influence on both hydrogel degradation rate and thermal transition behaviors. In other cases, introducing enzyme sensitive cleavage sites has proven an effective mechanism.

In this study, pNHMMj hydrogels were synthesized and displayed tunable degradation behavior in vitro and in vivo, supporting the design hypothesis that the addition of MAA as an autocatalyst for MAPLA hydrolysis would provide a method to accelerate the hydrogel dissolution. Manipulation of MAA content over a relatively small range resulted in widely varying degradation behavior, with 50% solubilization occurring in time frames from days to months, wider than what has been previously reported in the literature. The lower pH of the supernatant immediately after gelation and after a series of PBS/medium changes and stabilization steps indicated that the proton concentrations were higher in the environment for pNHMMj hydrogels with higher MAA content, as expected. This result also corresponds with the pH being lower inside and on the surface of pNHMM2 compared to other pNHMMj hydrogels having less MAA content, since greater MAA content would be the source of extra protons which decreased the supernatant pH. In addition, the pH appeared to be lower inside pNHMM2 compared to the surface of the hydrogel, suggesting diffusion-driven depletion of protons towards the surface of the hydrogel. The four pNHMMj hydrogels studied all experienced an abrupt mass loss at different times, indicating a rapid increase in hydrolysis rate and polymer hydrophilicity. This can be explained with the hindered diffusion of protons. As the proton concentration slowly builds up in the hydrogels, the autocatalytic effect would become stronger, leading to faster accumulation of cleaved lactic acid molecules and MAA residues, which in turn would contribute to a higher proton concentration. The fact that degradation of pNHMM10 (with highest MAA content among pNHMMj hydrogels) was slowed in weak basic buffer supports the proposed autocatalytic mechanism.

Hydrogel degradation was largely decoupled from both stiffness and thermal transition behavior (FIG. 9, bottom panel), probably because the MAA content was too low to affect the dominance of NIPAAm and highly hydrophobic MAPLA effects on thermal transition, and increases in electrostatic repulsion between MAA residues was not consequential. Theoretically, the ionizable MAA residues should increase pNHMMj copolymer hydrophilicity and pH sensitivity. Peppas et al. systematically studied the thermal sensitivity and pH sensitivity of poly(NIPAAm-co-MAA) hydrogels. They found that the thermal transition temperature increased from 32° C. to 34.5° C. as MAA in the poly(NIPAAm-co-MAA) hydrogels increased from 0 to 12 mol %; on the other hand, the swelling ratio of the poly(NIPAAm-co-MAA) hydrogels increased significantly between pH 5.3 and pH 5.7. The pH sensitivity was also observed in a poly(NIPAAm-co-MAA) interpenetrating polymeric network. In the current study, the examined pH range (6.4-7.4) was narrow, corresponding to infracted cardiac muscle as a potential application area. The pH range studied fell above the pKa of poly(methacrylic acid) as its effect on thermal transition behavior was studied for pNHMMj hydrogels containing small amounts of MAA. The pH sensitivity was not significant in the examined range and phase change and mechanical behavior that were attractive for minimally invasive delivery could be maintained, while the degradation rate could independently be optimized for a given application.

As expected, the pNHMM2 hydrogel showed faster in vivo degradation and disappearance from the site of injection compared to the other three hydrogels studied. However, the in vivo degradation and absorption of hydrogels qualitatively appeared to be substantially slower than in vitro. Day 21 was chosen as an endpoint for the in vivo studies based on the in vitro weight loss curve, expecting that almost all of the pNHMM2 hydrogel and about 50% of the mass of the pNHMM1 hydrogel would have been lost. Furthermore, hydrogel mass loss was expected to potentially be faster in vivo if local enzymatic activity contributed to the degradation process. The explanation for the apparently slower hydrogel loss in vivo could be that the catalyzing effect of MAA content was somewhat weakened in vivo as the tissue served as a more effective buffering system relative to the PBS in vitro.

Figure 28:
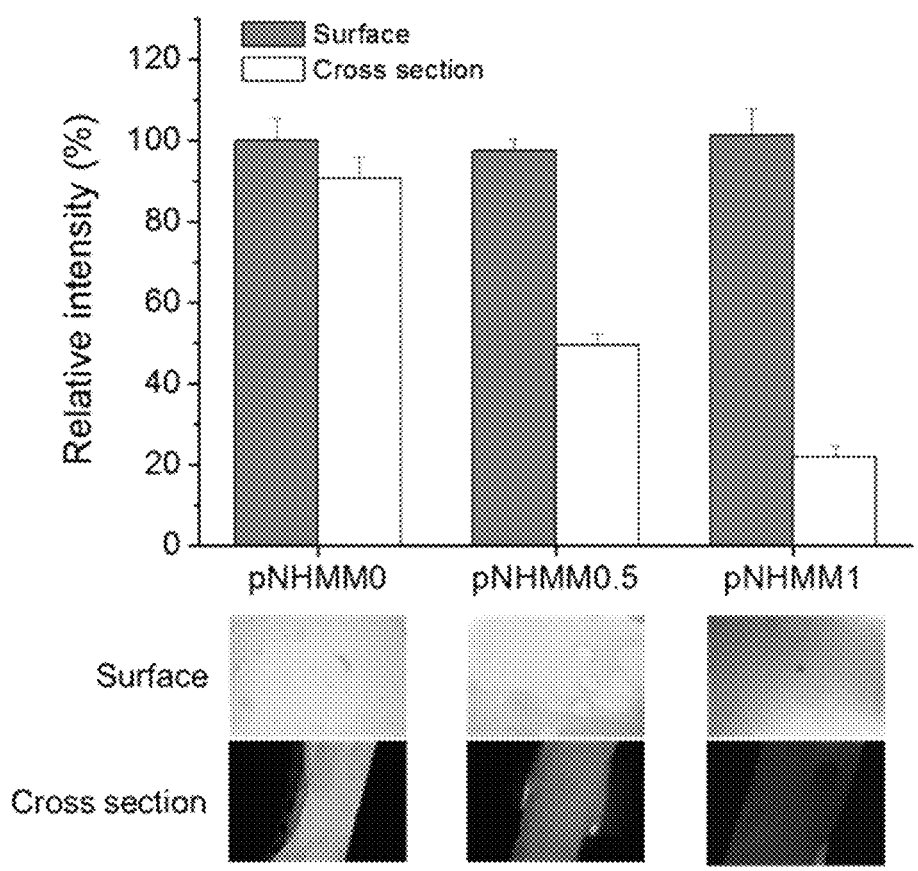
FIG. 28. Surface and cross section fluorescent intensities of fluorescein-labeled pNHMMj hydrogels after 21 d in PBS (with PBS exchange) shown as percentages of the initial intensities immediately after gelation. Data for pNHMM2 were not available due to fast degradation. Photos taken by Dino-Lite, intensities measured with ImageJ from images. Scale bar=2 mm.

The fluorescence of the remaining injected hydrogels was diminished for the faster degrading hydrogels with higher MAA content (FIG. 16). This result was in accordance with what was observed in vitro. It is known that fluorescein changes from a lactone form to neutral and cation forms under low pH, and its emission intensity and quantum yield drop significantly at ~490 nm. After 21 d in PBS, the fluorescence intensity of the labeled hydrogel interior dropped significantly for pNHMM0.5 and pNHMM1 versus that measured immediately after gelation, whereas the fluorescence intensity of pNHMM0 remained unchanged (FIG. 28). This result would explain the relatively strong green fluorescence only being observed for the pNHMM0 hydrogel after 21 d in vivo (FIG. 16), suggesting that the hydrogel interiors were more acidic for the other three studied hydrogels.

The foreign body response induced by the pNHMMj hydrogels 21 d post injection was characterized by local macrophage recruitment, as is typical of the foreign body response. The macrophages mainly distributed around the hydrogel mass, forming an encompassing cell layer. Few foreign body giant cells could be observed. For the slow degrading pNHMM0, pNHMM0.5 and pNHMM1 hydrogels, the macrophages did not infiltrate or separate the hydrogel mass, as opposed to the findings with pNHMM2, where the hydrogel was fragmented and the pieces surrounded by macrophages. This suggested that the in vivo absorption of pNHMMj hydrogels is not simply characterized by surface mass loss, but that degradation and solubilization occurs across the hydrogel with fragmentation. This fragmentation was observed in all cases in vitro, with fragmentation not occurring until the rapid phase of mass loss began.

The principle of manipulating acid autocatalysis may apply for controlling degradation rates for other thermally responsive hydrogels, and more broadly, biomaterials whose degradation is based on polyester hydrolysis. Ara et al. blended calcium compounds with different acidity with PLGA and found that the most basic calcium carbonate was most effective in delaying the degradation, while the most acidic calcium dihydrogenphosphate was least effective. Similar buffering effects on autocatalysis were also found by Zhang et al., where basic magnesium carbonate and magnesium hydroxide significantly decreased the degradation rate of PLGA films while neutral sodium chloride and zinc sulfate did not show comparable influence. Wu et al. have shown experimental results suggesting that pore morphology affects the diffusion of acidic degradation products from PLGA scaffolds, thus directly impacting the extent of acid catalyzed hydrolysis and degradation rate. For pNHMM hydrogels, the mass loss curves were characterized by rapid degradation following early periods of slower change, similar to the behavior of several other polyester materials. The autocatalytic mechanism might readily be applied to the design and synthesis for current material systems to introduce a tunable means of increasing degradation. For example, it is reasonable to assume that adding a small portion of pendant carboxyl groups onto PEG-PCL-PEG, PCL-PEG-PCL, or PEG-PLGA-PEG hydrogels could accelerate degradation, although such a design might also be dependent upon the overall hydrophilicity of the modified polymer system. Of note, a synthetic route to fabricate PCL-PEG-PCL copolymer bearing pendant carboxyl groups on the PCL blocks has been reported by Lavasanifar et al. The degradation rate of thermally responsive hydrogels has been studied and utilized to control the release of pharmaceutical agents and proteins. The potential of thermally responsive hydrogels as cell carriers has been demonstrated as well. Given that hydrogel degradability significantly influences cell proliferation, migration and differentiation, along with the therapeutic outcomes of injection therapies, adding acid to tune the degradability of thermally sensitive hydrogels is attractive.

One key advantage of the strategy employed here is that relatively small amounts of catalyst (acid) did not significantly influence the material properties of interest. However, there are potential limitations and drawbacks of this strategy. First, for the acid to play its role, a certain level of diffusion and access of protons to the ester bonds is needed, which in turn is dependent on the water content in the hydrogel. The accelerating effect may not be as readily achieved for more hydrophobic materials, particularly in the early stages of degradation. Also, for injectable hydrogels, the catalyzing effect may vary across injection sites under the influence of buffering capacity. Second, an acidic microenvironment would be generated for faster degradation to take place, which would also lower the pH for the cells and corresponding physiological events in the vicinity of the implant. This was not explicitly studied in this report, but the histological results did not suggest an obvious effect for the healthy skeletal muscle bed examined.

Conclusion

A series of NIPAAm based thermally responsive polymers (pNHMMj) were synthesized, which contained varying MAA content. By releasing protons that catalyzed ester hydrolysis, MAA accelerated the degradation and adsorption of the hydrogels both in vitro and in vivo, and this effect was positively correlated to MAA content in the copolymer. The thermal transition behavior and mechanical strength did not significantly vary among the pNHMMj hydrogels. On the other hand, the pNHMMj hydrogels showed low cytotoxicity and appeared to induce a mild foreign body response. The introduced autocatalysis strategy of tuning the degradation of thermally responsive hydrogels where degradation or solubilization is determined by their polyester components might be applied to other tissue engineering and regenerative medicine applications where appropriate biomaterial degradation behavior is needed.

Example 6—Synthesis of Poly(NIPAAm-co-VP-co-MAPLA) Hydrogels

Figure 17:
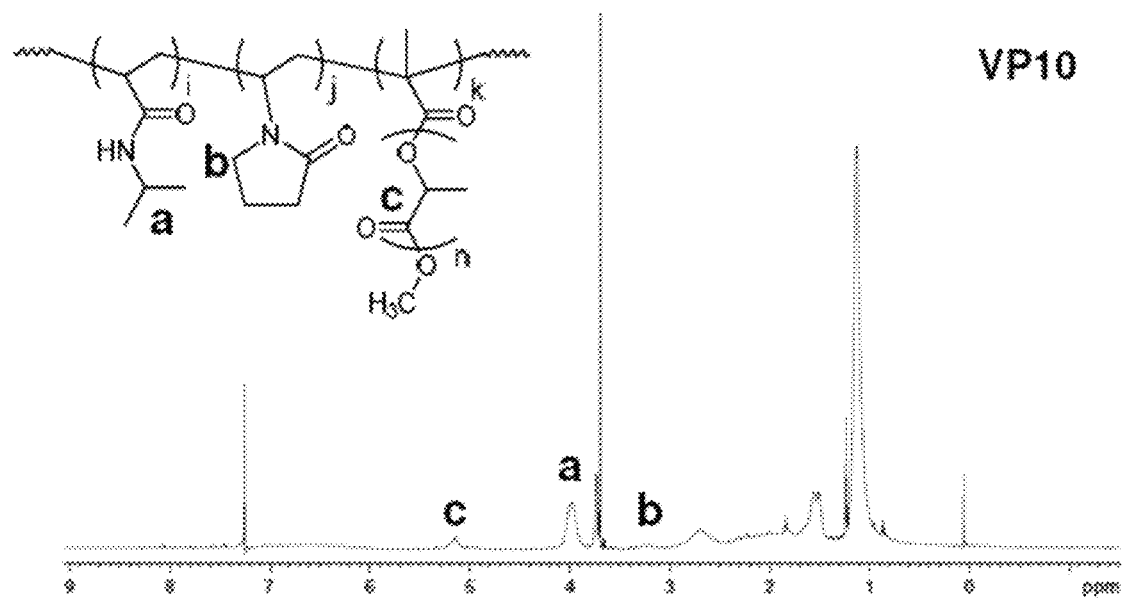
FIG. 17. Poly(NIPAAm-co-VP-co-MAPLA) copolymers synthesized from NIPAAm, VP, and MAPLA by free radical polymerization.

Poly(NIPAAm-co-VP-co-MAPLA) copolymers were synthesized from NIPAAm, VP and MAPLA by free radical polymerization. The feed ratios of NIPAAm, VP and MAPLA were 80/j/(20-j), where j=10, 15 (FIG. 17). Monomers (0.066 mol) were dissolved in 180 mL of 1,4-dioxane containing 0.23 g BPO. The polymerization was carried out at 70° C. for 24 h under an argon atmosphere. The copolymer was precipitated in hexane and further purified by precipitation from THF into diethyl ether and vacuum-dried, with yields of ~80%.

$^1$H spectra of poly(NIPAAm-co-VP-co-MAPLA) copolymers were recorded with a 600 MHz BRUKER spectrometer using $CD3C_1$ as solvent (FIG. 17). Molecular weight of the copolymers was determined by gel permeation chromatography (GPC, Waters Breeze System, Waters 1515 HPLC PumpWaters 2414 differential refractometer). The copolymers were dissolved in THF at a concentration of 1 mg/mL and the GPC analysis were performed at 35° C. A poly (methyl methacrylate) standard kit (Fluka, ReadyCal Set Mp 500-2700000) was used for molecular weight-elution volume calibration.

Results: Poly(NIPAAm-co-VP-co-MAPLA) copolymers with different composition were successfully synthesized. The actual compositions were slightly different from the feed ratio (FIG. 17).

Rheology studies were conducted on a TA Instrument rheometer (AR2000) to observe the mechanical property change of the hydrogels during the temperature induced sol-gel transition. The polymer solutions (15 wt % in PBS) were placed between two parallel plates. The heating rate was 5° C./min, the shear storage modulus G' were collected as a function of temperature at a fixed strain of 2% and a frequency of 1 Hz.

To measure the transition time of hydrogels in 37° C. air, 150 uL of each type of hydrogel was added to pre-cooled a 96-well plate and placed in a plate reader which was pre-warmed to and set at 37° C. Absorbance at 490 nm was recorded for 15 min.

Figure 18:
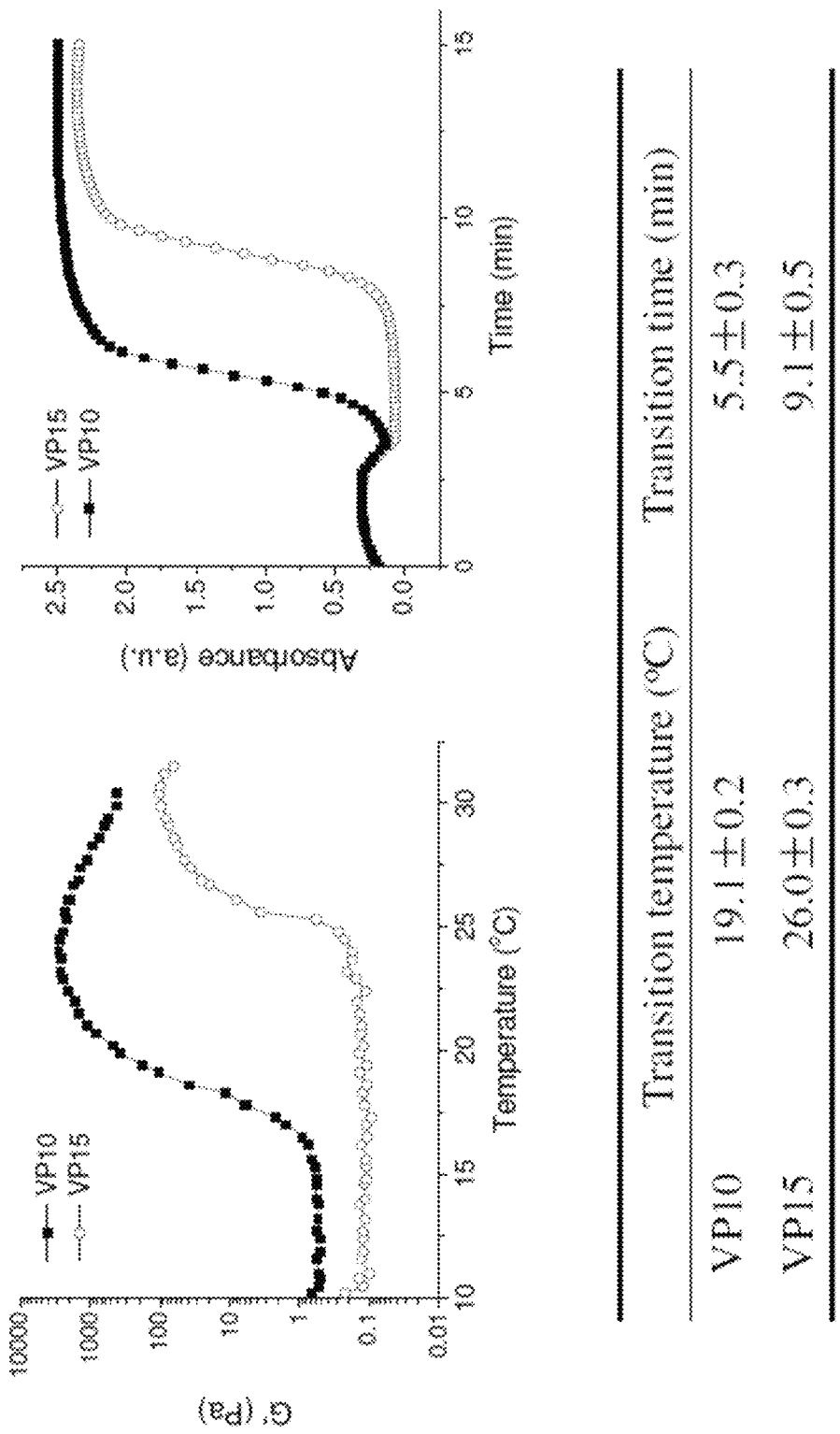
FIG. 18. Transition time of poly(NIPAAm-co-VP-co-MAPLA) copolymer hydrogels in 37° C. air.

Results: VP10 and VP15 have transition temperature of 19° C. and 26° C., respectively (FIG. 18). VP15 has higher hydrophilicity as evidenced by higher transition temperature and longer transition time.

Relevance: It shows our capability to modulate hydrogel hydrophilicity by changing polymer composition under the described design and synthesis route.

Hydrogel degradation was quantified by mass loss measurements. Hydrogels with known initial dry masses (~60 mg) were immersed into 6 mL of PBS (replaced weekly to maintain a constant pH value of 7) at 37° C. At predefined time points over a 10 weeks period the hydrogel (n=3 each) were lyophilized and the relative mass loss was recorded.

Hydrogel discs after 24 h equilibrium in 37° C. PBS were weighed (water on gel surface removed) and thoroughly dried in oven. Water absorption was calculated as (wet weight-dry weight)/wet weight×100%.

Figure 19:
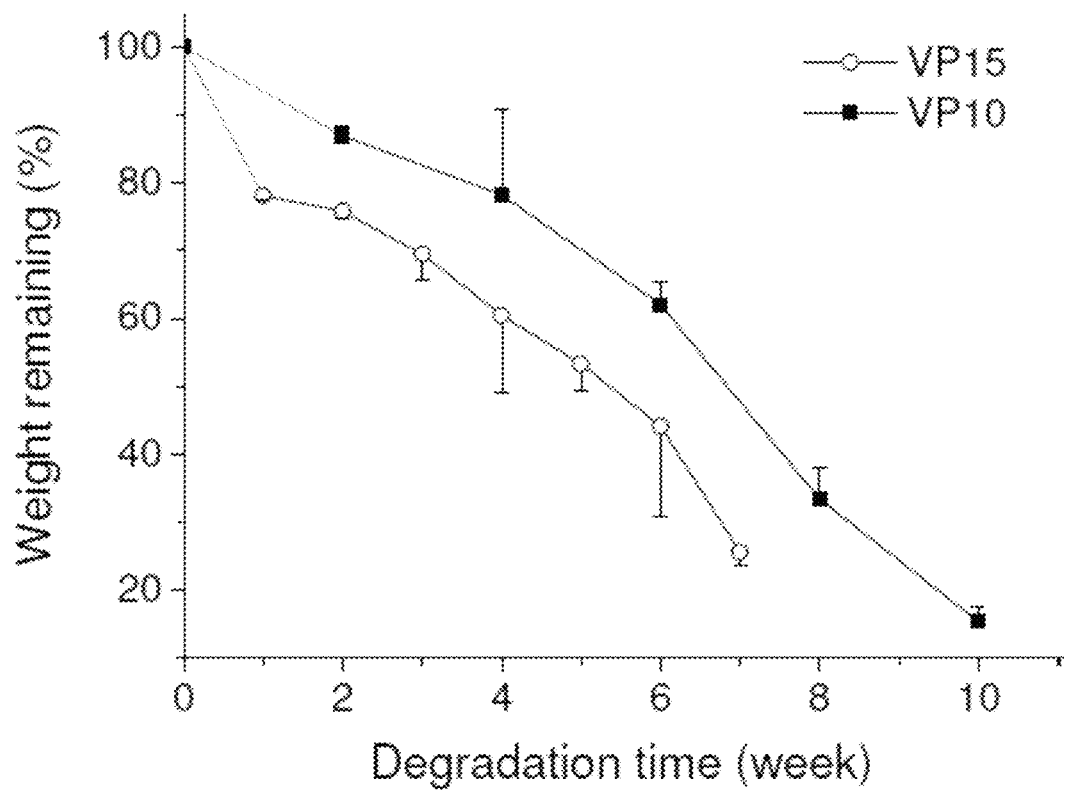
FIG. 19. Poly(NIPAAm-co-VP-co-MAPLA) copolymer hydrogel degradation.

Results: Being more hydrophilic, VP15 absorbs more water and degrades faster in PBS than VP10 (FIG. 19). 50% weight loss in PBS takes 5 weeks and 7 weeks for VP15 and VP10, respectively.

Relevance: Similar with other hydrogels disclosed, poly (NIPAAm-co-VP-co-MAPLA) hydrogels can provide mechanical support on injection sites for a relatively long time.

To measure the mechanical properties of the hydrogels, samples were incubated in a 37° C. water bath for 24 h to reach a stable water content, and then the solid hydrogels were cut into round discs with 3 mm diameter and 3 mm thickness, and then loaded in a water bath equilibrated to 37° C. An ElectroForce 3200 Series II (Bose, Minn., US)

equipped with a 2.5 N load cell was utilized to record the compressive stress-strain curve immediately after the samples were taken out of the water bath.

Figure 20:
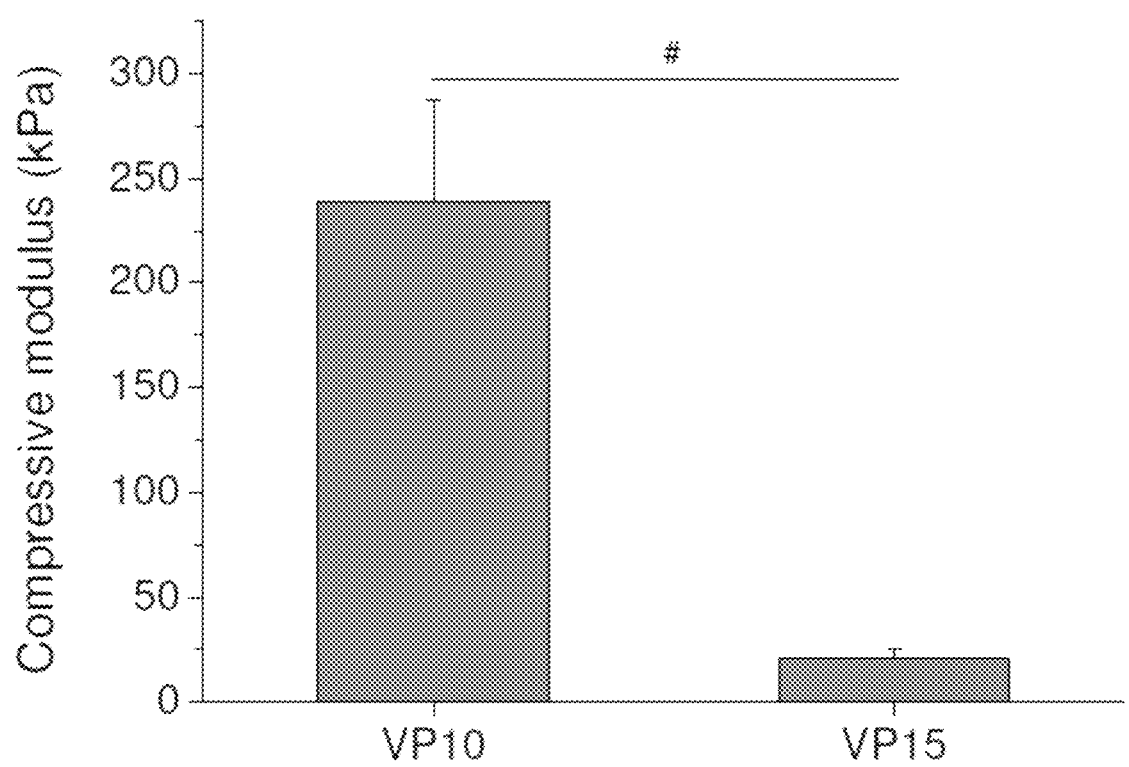
FIG. 20. Mechanical properties of poly(NIPAAm-co-VP-co-MAPLA) copolymer hydrogels.

Results: Being more hydrophilic, VP15 has a weaker mechanical strength than VP10 (FIG. 20).

Relevance: The compressive modulus of VP15 is within the range of soft tissue modulus, meaning it is strong enough as a bulking agent. VP10 should work better in terms of mechanical strength.

The cytotoxicity of the degradation products of VP15 and VP10 hydrogels was assessed by measuring the relative metabolic activity of rat myoblasts (H9C2 cells) cultured in Dulbecco's modified Eagle medium (DMEM) (Gibco, Life technologies) with 10% fetal bovine serum (FBS), 1% penicillin/streptomycin, and supplemented at 10% with hydrogel degradation solution. The hydrogel degradation solution was prepared from incubation of the hydrogel in PBS. Culture medium with PBS added at 10% was used as a negative control. H9C2 cells were seeded at an initial density of 30,000/cm2 and their metabolic activity was measured (n=6 each) using an MTS assay kit (Promega CellTiter 96 Cell Proliferation Assay). To qualitatively verify the results of the above test, cells were also observed under fluorescence microscopy after live/dead staining with a Promokine Live/Dead Cell Staining Kit.

Figure 21:
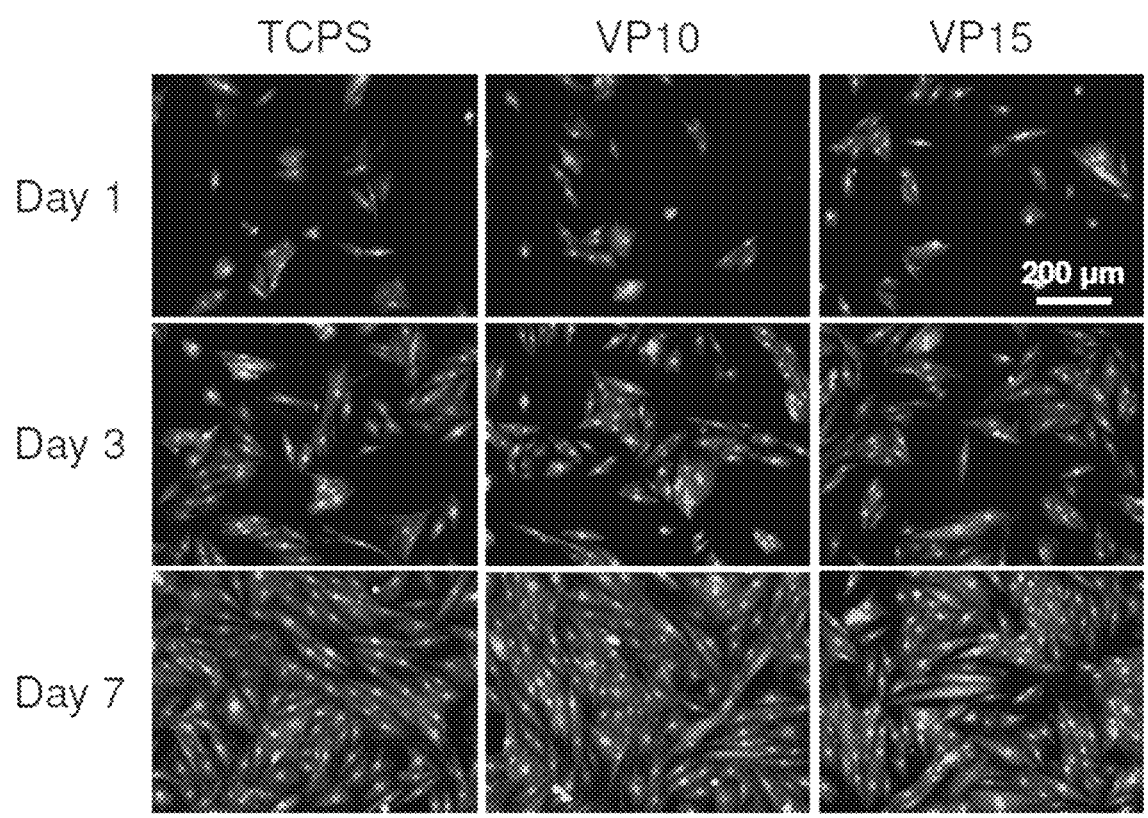
FIG. 21. Cytotoxicity of degradation products of poly (NIPAAm-co-VP-co-MAPLA) copolymer hydrogels evaluated by live/dead staining.
Figure 22:
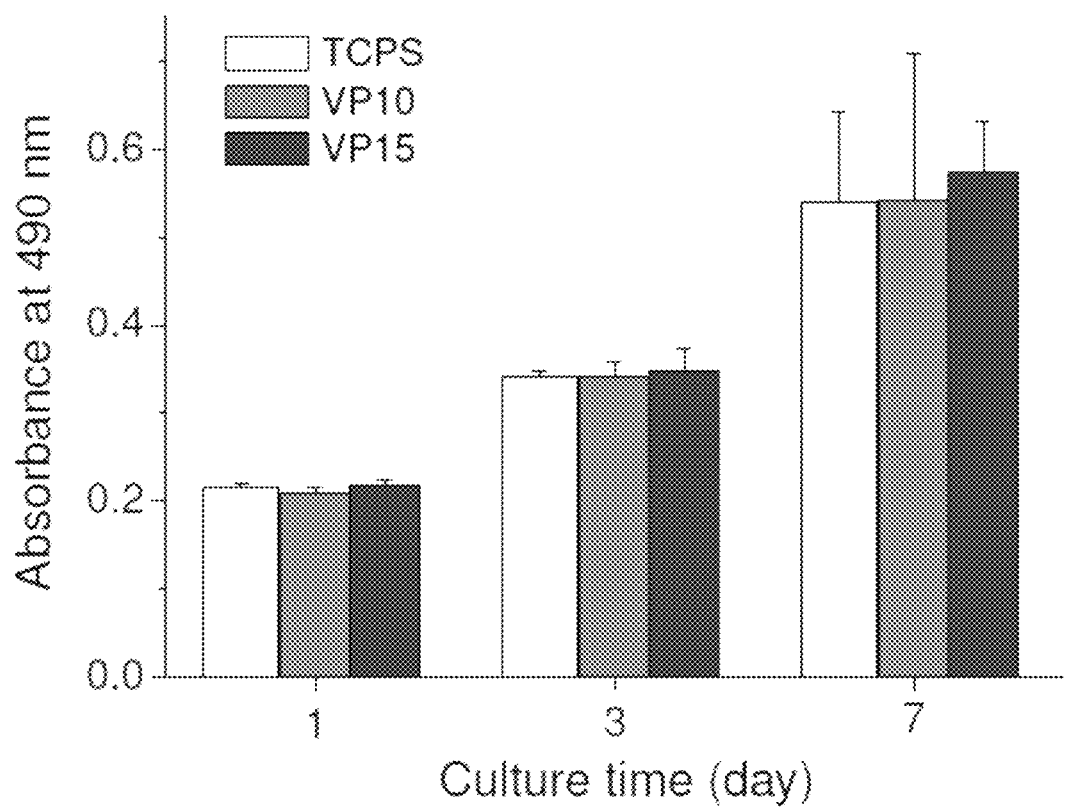
FIG. 22. Cytotoxicity of degradation products of poly (NIPAAm-co-VP-co-MAPLA) copolymer hydrogels evaluated by MTS assay.

Results: H9C2 cells stayed alive and proliferate normally under the influence of hydrogel degradation products (FIGS. 21 and 22).

Relevance: The degradation products of VP15 and VP10 have negligible cytotoxicity, showing their safety and biomedical materials.

Figure 23:
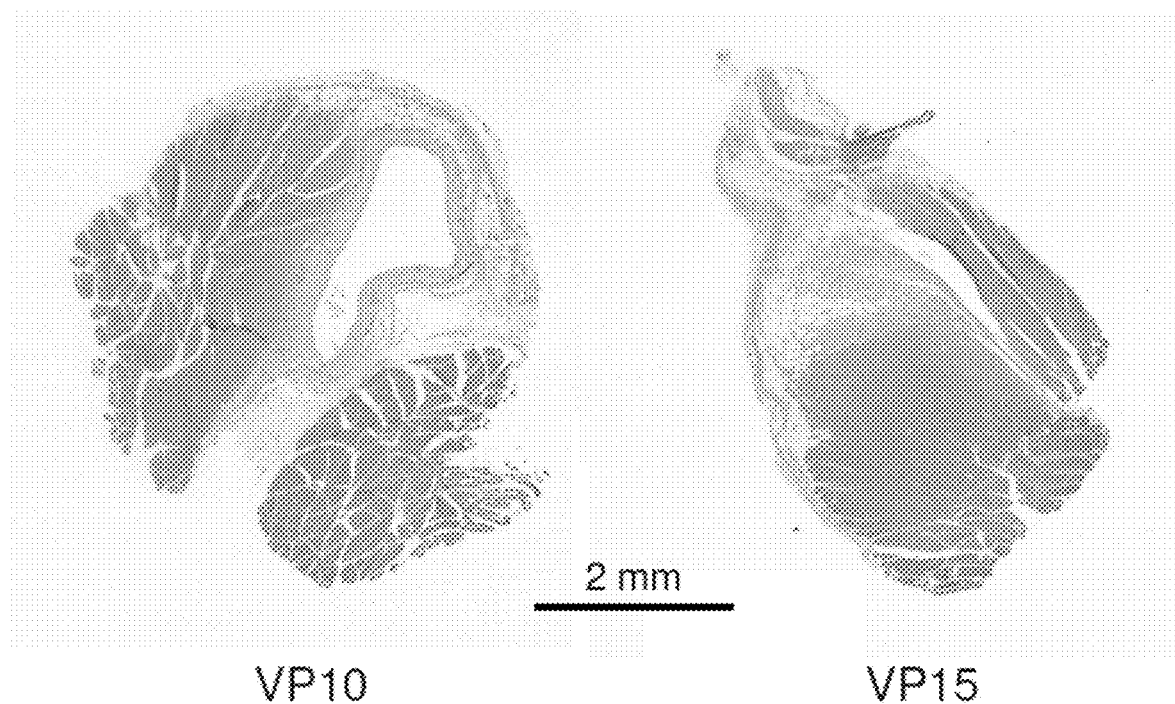
FIG. 23. H&E staining of tissue following injection of poly(NIPAAm-co-VP-co-MAPLA) copolymer hydrogels.

Adult female Lewis rats weighing 160-210 g were utilized in a protocol that followed the National Institutes of Health guidelines for animal care and that was approved by the University of Pittsburgh's Institutional Animal Care and Use Committee. Anesthesia was induced with 3.0% isoflurane inhalation with 100% oxygen followed by 1.5-2% isoflurane with 100% oxygen during procedure. Dermatotomy was performed to expose the inner thigh muscles on both legs. Single injections of 200-250 μL of VP15 or VP10 hydrogel were made approximately 3 mm deep in the muscle bed. After 28 d, rats were sacrificed and the inner thigh muscles were excised and fixed in 10% formaldehyde for 3 d before embedding. H&E staining was performed (FIG. 23).

Results: Typical foreign body response was observed featuring recruited macrophages. However, the morphology of VP10 and VP15 28 days after injection is different. VP10 formed a solid mass in tissue while VP15 diffused better and integrated with the muscle (FIG. 23).

Relevance: This difference shows VP10 and VP15 may have different releasing effects while carrying bioactive agents.

40 or 10 μL of adeno-associated virus (AAV) with packed GFP was mixed with VP15 hydrogel before gelation at 37° C. Hydrogel was then immersed in 37° C. DMEM. Media with released AAV particles were collected at different time points and new media was added to allow further release. The media with released AAV particles was used to infect pre-seeded HEK293 cells for 48 h. Cells were observed with a fluorescent microscope.

Figure 24:
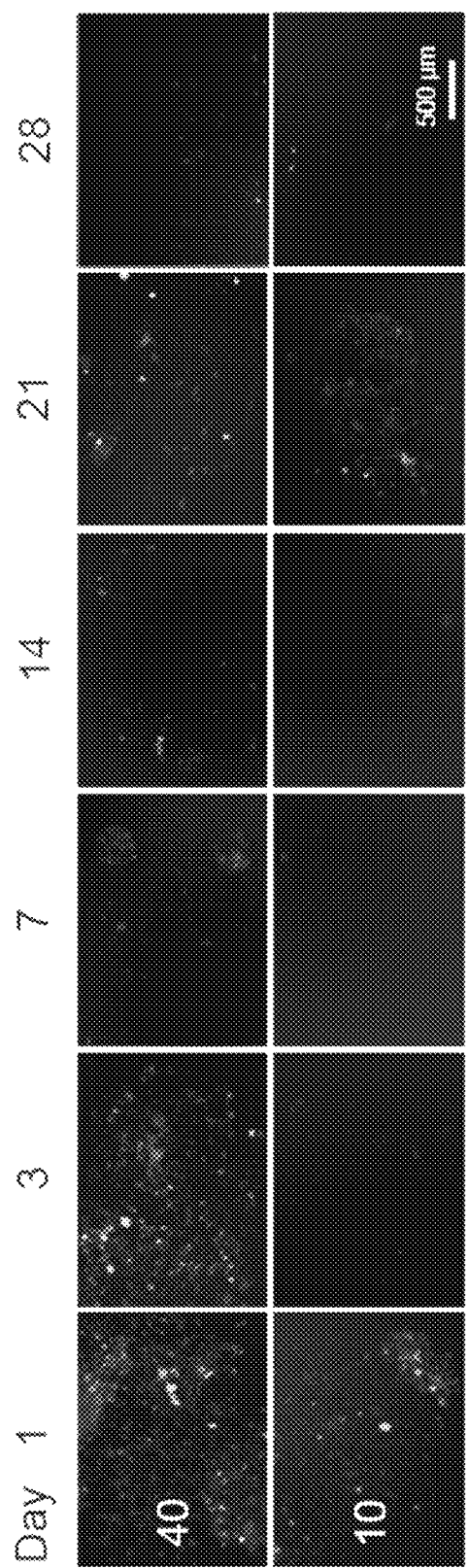
FIG. 24. Adeno-associated virus release from poly(NIPAAm-co-VP-co-MAPLA) copolymer hydrogels.

Results: HEK293 cells were infected with AAV particles released from hydrogel. The AAV particles released 14 days after gelation still has some level of activity (FIG. 24).

Relevance: It is proved that slow release of bioactive agents can be achieved with poly(NIPAAm-co-VP-co-MA-PLA) hydrogels while maintaining some level of activity, which shows the potential of poly(NIPAAm-co-VP-co-MA-PLA) hydrogels as mechanical support+carrier for bioactive agents.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

We claim:

1. A composition, comprising a copolymer having a lower critical solution temperature (LCST) of less than 37° C., consisting essentially of N-isopropyl acrylamide (NIPAAm) residues; acrylic acid (AAc) residues; a hydroxyethylmethacrylate-poly(trimethylene carbonate) (HEMAPTMC) macromer residues; and methacrylic acid (MAA) monomer residues, wherein the copolymer is prepared by radical polymerization with a molar feed ratio of NIPAAm:AAc:HEMAPTMC:MAA in a range of 71.5-94:2.5-16:4.5-11:0.5-2.5, and has a degradation rate of less than 200 days in vivo.

2. The composition of claim 1, wherein the copolymer is prepared by radical polymerization with a molar feed ratio of NIPAAm:AAc:HEMAPTMC:MAA in the range of 85-87:3-5:10:0.5-2.

3. The composition of claim 1, wherein the copolymer is prepared by radical polymerization with a molar feed ratio of NIPAAm:AAc:HEMAPTMC:MAA in the range of 86-87:3-4:10:0.5-2.

4. The composition of claim 1, wherein the copolymer is prepared by radical polymerization with a molar feed ratio of NIPAAm:AAc:HEMAPTMC:MAA in the range of 72-88:3-15:4.5-11:0.5-2.

5. The composition of claim 1, wherein the LCST is less than 35° C.

6. The composition of claim 1, wherein the LCST is less than 34° C.

* * * * *